(12) United States Patent
Yoon et al.

(10) Patent No.: US 11,426,729 B2
(45) Date of Patent: Aug. 30, 2022

(54) SYSTEMS AND METHODS FOR WHOLE CELL ANALYSIS

(71) Applicant: THE REGENTS OF THE UNIVERSITY OF MICHIGAN, Ann Arbor, MI (US)

(72) Inventors: Euisik Yoon, Ann Arbor, MI (US); Yu-Heng Cheng, Ann Arbor, MI (US); Yu-Chih Chen, Ann Arbor, MI (US); Riley Brien, Ann Arbor, MI (US); Max S. Wicha, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 236 days.

(21) Appl. No.: 16/480,396

(22) PCT Filed: Jan. 19, 2018

(86) PCT No.: PCT/US2018/014353
§ 371 (c)(1),
(2) Date: Jul. 24, 2019

(87) PCT Pub. No.: WO2018/140302
PCT Pub. Date: Aug. 2, 2018

(65) Prior Publication Data
US 2019/0344270 A1     Nov. 14, 2019

Related U.S. Application Data

(60) Provisional application No. 62/449,867, filed on Jan. 24, 2017.

(51) Int. Cl.
*B01L 3/00* (2006.01)
(52) U.S. Cl.
CPC ... *B01L 3/502738* (2013.01); *B01L 3/502761* (2013.01); *B01L 2200/0668* (2013.01); (Continued)
(58) Field of Classification Search
CPC .......... B01L 3/50273; B01L 3/502715; B01L 3/502769; B01L 7/00; B01L 2200/0684; B01L 2300/047; B01L 2300/06; B01L 2300/0819; B01L 2300/12; B01L 2300/1827; B01L 2400/0406;
(Continued)

(56) References Cited

U.S. PATENT DOCUMENTS

2007/0248971 A1 * 10/2007 Maerkl ............ B01L 3/502707
435/6.19
2013/0078163 A1    3/2013 Chung et al.
(Continued)

OTHER PUBLICATIONS

Altschuler, et al. Cellular heterogeneity: do differences make a difference? Cell. May 14, 2010;141(4):559-63.
(Continued)

*Primary Examiner* — Jennifer Wecker
*Assistant Examiner* — Oyeleye Alexander Alabi
(74) *Attorney, Agent, or Firm* — Casimir Jones, S.C.; Tanya A. Arenson

(57) ABSTRACT

The present disclosure relates to systems and methods for whole cell analysis. In particular, the present disclosure relates to single cell genomic analysis (e.g., gene expression analysis.

20 Claims, 48 Drawing Sheets

(52) U.S. Cl.
CPC ............ B01L 2300/0816 (2013.01); B01L 2300/0864 (2013.01); B01L 2300/0883 (2013.01); B01L 2300/0893 (2013.01); B01L 2400/086 (2013.01)

(58) Field of Classification Search
CPC ..... B01L 2400/0442; B01L 2400/0688; B01L 2400/086; G01N 35/00069; G01N 2035/00158; G01N 2035/00237; G01N 2035/1034; G01N 15/1484
See application file for complete search history.

(56) References Cited

U.S. PATENT DOCUMENTS

| | | | | |
|---|---|---|---|---|
| 2013/0190212 | A1* | 7/2013 | Handique | G01N 1/28 506/37 |
| 2015/0018226 | A1* | 1/2015 | Hansen | G01N 33/569 506/9 |
| 2016/0067711 | A1 | 3/2016 | Yoon et al. | |

OTHER PUBLICATIONS

Bild, et al., Oncogenic pathway signatures in human cancers as a guide to targeted therapies. Nature. Jan. 19, 2006;439(7074):353-7.
Bose, et al., Scalable microfluidics for single-cell RNA printing and sequencing. Genome Biology vol. 16, Article No. 120 (2015).
Bozovic-Spasojevic, I. et al. The Prognostic Role of Androgen Receptor in Patients with Early-Stage Breast Cancer: A Meta-analysis of Clinical and Gene Expression Data. Clin Cancer Res. Jun. 1, 2017;23(11):2702-2712.
Brabletz, EMT and MET in metastasis: where are the cancer stem cells? Cancer Cell. Dec. 11, 2012;22(6):699-701.
Chen, Y.-C., et al., Single Cell Proteolytic Assays to Investigate Cancer Clonal Heterogeneity and Cell Dynamics Using an Efficient Cell Loading Scheme. Sci Rep. Jun. 10, 2016;6:27154.
Cheng, Y.-H., et al., Scaling and automation of a high-throughput single-cell-derived tumor sphere assay chip. Lab Chip. Oct. 7, 2016;16(19):3708-17.
Dalerba, et al., Single-cell dissection of transcriptional heterogeneity in human colon tumors. Nat Biotechnol. Nov. 13, 2011;29(12):1120-7.
Fan, et al., Expression profiling. Combinatorial labeling of single cells for gene expression cytometry. Science. Feb. 6, 2015;347(6222):1258367.
Ferreira, et al., Circulating tumor cell technologies. Mol Oncol. Mar. 2016;10(3):374-94.
Gierahn, T.M. et al. Seq-Well: portable, low-cost RNA sequencing of single cells at high throughput. Nat Methods. Apr. 2017;14(4):395-398.
Jakabova, A. et al. Molecular characterization and heterogeneity of circulating tumor cells in breast cancer. Breast Cancer Res Treat. Dec. 2017;166(3):695-700.
Klein, A.M. et al. Droplet barcoding for single-cell transcriptomics applied to embryonic stem cells. Cell. May 21, 2015;161(5):1187-1201.
Liao, et al., Enrichment of a population of mammary gland cells that form mammospheres and have in vivo repopulating activity. Cancer Res. Sep. 1, 2007;67(17):8131-8.
Lin, E. et al. High-Throughput Microfluidic Labyrinth for the Label-free Isolation of Circulating Tumor Cells. Cell Syst. Sep. 27, 2017;5(3):295-304.e4.
Liu, et al., Breast cancer stem cells transition between epithelial and mesenchymal states reflective of their normal counterparts. Stem Cell Reports. Dec. 27, 2013;2(1):78-91.
Livak et a., Analysis of relative gene expression data using real-time quantitative PCR and the 2(-Delta Delta C(T)) Method. *Methods*. Dec. 2001;25(4):402-8.
Lohr, J.G. et al. Whole-exome sequencing of circulating tumor cells provides a window into metastatic prostate cancer. Nat Biotechnol. May 2014;32(5):479-84.
Macosko, E.Z. et al. Highly Parallel Genome-wide Expression Profiling of Individual Cells Using Nanoliter Droplets. Cell. May 21, 2015;161(5):1202-1214.
Macosko, et al., Highly Parallel Genome-wide Expression Profiling of Individual Cells Using Nanoliter Droplets. Cell. May 21, 2015;161(5):1202-1214.
Magee, et al., Cancer stem cells: impact, heterogeneity, and uncertainty. Cancer Cell. Mar. 20, 2012;21(3):283-96.
Ramskold, et al., Full-length mRNA-Seq from single-cell levels of RNA and individual circulating tumor cells. Nat Biotechnol. Aug. 2012;30(8):777-82.
Schena, et al., Quantitative monitoring of gene expression patterns with a complementary DNA microarray. Science. Oct. 20, 1995;270(5235):467-70.
Semenza, Targeting HIF-1 for cancer therapy. Nat Rev Cancer. Oct. 2003;3(10):721-32.
Shapiro, et al., Single-cell sequencing-based technologies will revolutionize whole-organism science. Nat Rev Genet. Sep. 2013;14(9):618-30.
Shin, et al., Intratumoral phenotypic heterogeneity as an encourager of cancer invasion. Integr Biol (Camb). Jul. 24, 2014;6(7):654-61.
Streets, et al., Microfluidic single-cell whole-transcriptome sequencing. Proc. Natl. Acad. Sci. U. S. A., 2014, 111, 7048-53.
Tang, et al., mRNA-Seq whole-transcriptome analysis of a single cell. Nature Methods vol. 6, pp. 377-382 (2009).
Tsai, J.H. & Yang, J. Epithelial-mesenchymal plasticity in carcinoma metastasis. Genes Dev. Oct. 15, 2013;27(20):2192-206.
Van't Veer, et al., Gene expression profiling predicts clinical outcome of breast cancer. Nature. Jan. 31, 2002;415(6871):530-6.
Vishnoi, M. et al. The isolation and characterization of CTC subsets related to breast cancer dormancy. Scientific Reports vol. 5, Article No. 17533 (2015).
Vogel, et al., Efficacy and safety of trastuzumab as a single agent in first-line treatment of HER2-overexpressing metastatic breast cancer. J Clin Oncol. Feb. 1, 2002;20(3):719-26.
Wang, et al., RNA-Seq: a revolutionary tool for transcriptomics. Nat Rev Genet. Jan. 2009;10(1):57-63.
White, et al., High-throughput microfluidic single-cell RT-qPCR. Proc Natl Acad Sci U S A. Aug. 23, 2011;108(34):13999-4004.

* cited by examiner

G

SYSTEMS AND METHODS FOR WHOLE CELL ANALYSIS

CROSS REFERENCE TO RELATED APPLICATIONS

This application is a 371 U.S. National Phase Entry of pending International Application No. PCT/US2018/014353, filed Jan. 19, 2018, which claims the benefit of U.S. Provisional Application No. 62/449,867, filed Jan. 24, 2017, which are incorporated herein by reference in their entireties.

STATEMENT REGARDING FEDERALLY SPONSORED RESEARCH OR DEVELOPMENT

This invention was made with government support under awards W911NF-08-2-0004 and W911NF-06-R-0006 awarded by the U.S. Army Research Lab, DARPA. The government has certain rights in the invention.

FIELD OF THE DISCLOSURE

The present disclosure relates to systems and methods for whole cell analysis. In particular, the present disclosure relates to single cell genomic analysis (e.g., gene expression analysis).

BACKGROUND OF THE DISCLOSURE

The understanding of cell gene expression not only can foster the fundamental research in cancer but also provide great potential for precision medicine by designing target medicine to specific gene expression patterns (van't Veer, et al., Nature, 2002, 415, 530-536; Semenza, Nat Rev Cancer, 2003, 3, 721-732; Bild, et al., Nature, 2006, 439, 353-357). For instance, to better understand the metastasis process in cancer, gene expression analysis can be used to understand the mesenchymal-epithelial transit ion (MET) and epithelial-mesenchymal transition (MET) of the primary tumor cells, the invading tumor cells, and the metastasized secondary tumor cells (Brabletz, Cancer Cell, 2016, 22, 699-701; Liu, et al., Stem Cell Reports, 2014, 2, 78-91). For clinical applications, there are tremendous developments in target therapy and precision medicine to target specific gene expressed in certain patient populations. For example, trastuzumab has been shown to be effective in treating breast cancer with HER2 over expressions (Vogel, et al., J. Clin. Oncol., 2002, 20, 719-726). As a result, the development of transcriptome analysis tools is critical to facilitate fundamental research and provide reliable clinical results as companion diagnostic tools.

Although there are different conventional approaches available to profile cell gene expressions, such as DNA microarray, quantitative polymerase chain reaction (PCR) and transcriptome sequencing, those methods usually only provide population-average results, masking the heterogeneity of sample populations (Livak and Schmittgen, Methods, 2001, 25, 402-408; Schena, et al., Science (80)., 1995, 270, 467 LP-470; Wang, et al., Nat Rev Genet, 2009, 10, 57-63). As cancer is known for its heterogeneity and people have identified that some rare cell sub-populations play key roles in cancer development, it is critical to develop methods enabling gene expression analysis at single cell resolution (Magee, et al., Cancer Cell, 2012, 21, 283-296; Shin, et al., Integr. Biol. (Camb)., 2014, 6, 654-61; Altschuler and Wu, Cell, 2010, 141, 559-563). Thus, ultra-sensitive reagent kits were developed to enable single cell PCR and sequencing analysis by processing individual cells in separate tubes (Tang, et al., Nat Methods., 2009, 6; Dalerba, et al., Nat. Biotechnol., 2011, 29, 1120-1127; Ramskold, et al., Nat. Biotechnol., 2012, 30, 777-8). However, those approaches have several intrinsic drawbacks. Without a robotic system, it is very labor intensive to isolate cells in each tube, limiting the assay throughput (Liao, et al., Cancer Res., 2007, 67, 8131-8138). With robotic sorting systems such as fluorescent activated cell sorting (FACS) technology, it's possible to achieve higher throughput with higher single cell yield in tubes, but the high shear stress during the sorting process may affect cell viability and its gene expression (Shapiro, et al., Nat. Rev. Genet., 2013, 14, 618-3). Additionally, the cost for reagents adds up dramatically if the higher throughput is needed, which limits its application in research labs and clinics.

To overcome the challenge, microfluidics emerges as a promising technology for single cell transcriptome analysis. By trapping single cells in microfluidic chambers, microfluidic single cell RT-PCR was developed to analyze up to hundreds of cells on chip for gene expression analysis (White, et al., Proc. Natl. Acad. Sci. U.S.A., 2011, 108, 13999-14004; Streets, et al., Proc. Natl. Acad. Sci. U.S.A., 2014, 111, 7048-53). With the passive cell trapping structure, individual cells are isolated in each chamber for analysis, which increases the throughput without intensive manual operation. By processing the assay in microfluidic chambers with nano-liter and micro-liter volume, reagent consumption is also reduced significantly. However, this technology requires large PCR reagent chamber next to the cell capture chamber for on chip PCR, which occupies a large area and limits the throughput. The quantitative PCR method also requires a selection of genes for analysis in advance, limiting the number of genes that can be profiled per assay. To overcome these challenges, droplet-based microfluidics with cell and molecule barcoding technologies such as drop-seq and in-drop were developed for high throughput analysis at the scale around thousands of cells per assay (Macosko, et al., Cell, 2016, 161, 1202-1214; Klein, et al., Cell, 2016, 161, 1187-1201). Single cells are randomly encapsulated in liquid droplet and paired to a barcoded bead in lysis buffer. After cell lysis, the barcoded beads capture the mRNA released from cells, and the beads are retrieved off chip for downstream processes such as reverse transcription and PCR amplification. With the barcoded beads, micro-well based microfluidics was also reported to pair beads and cells for single cell transcriptome analysis (Fan, et al., Science (80)., 2015, 347; Bose, et al., Genome Biol., 2015, 16, 1-16). However, with droplet and microwell system, it usually requires thousands of cells for analysis due to the cell loss in the single cell capture process, limiting its application for rare cell analysis. As a result, as there are clinical samples with small number of cells such as circulating tumor cells (CTCs), there is an unmet need to analyze such rare sample to enable more fundamental research and investigate the clinical application of CTCs.

SUMMARY OF THE DISCLOSURE

The present disclosure relates to systems and methods for whole cell analysis. In particular, the present disclosure relates to single cell genomic analysis (e.g., gene expression analysis).

For example, in some embodiments, the present disclosure provides a microfluidic device, comprising: a plurality of branched channels comprising an entrance channel and an exit channel and a plurality of parallel single cell chambers comprising a cell capture site disposed therein. In some embodiments, the entrance channel is tapered smaller in the direction of fluid flow and the exit channel is tapered larger in the direction of fluid flow. In some embodiments, the device further comprises a fluid inlet and/or a fluid outlet. In some embodiments, the entrance and exit channels have a height of approximately at least 5 times the height of the single cell chambers. In some embodiments, the entrance and exit channels have a height of at least 10 times the height of the single cell chambers. In some embodiments, the device comprises at least 500 (e.g., at least 5000, or at least 10,000) single cell chambers. In some embodiments, the single cell chambers further comprise an entrance valve distal to the single cell chamber and/or an exit valve proximal to the single cell chamber. In some embodiments, the cell capture chamber further comprises a bead capture site. In some embodiments, the cell capture site and the bead capture site comprise sealing valves proximal to the cell capture site and distal to the bead capture site. In some embodiments, the cell capture site and bead capture site are separated by a wall (e.g., at least 20 µm thick and 20 µm long). In some embodiments, the cell capture chamber and the sealing valves overlap at least 20% into the valve area. In some embodiments, the bead capture sites and the cell capture sites alternate. In some embodiments, the entrance valve has an opening of at least 35 µm and the exit valve has an opening of at least 15 µm. In some embodiments, the device further comprises a plurality of bead capture chambers in parallel with the single cell capture chambers. In some embodiments, the bead capture chambers and said single cell capture chambers are separated by a channel. In some embodiments, the channel comprises an isolation valve between the bead capture chamber and the single cell capture chamber. In some embodiments, the device further comprises a plurality of wash valve controlled washing channels in fluid communication with the entrance channel and the exit channel. In some embodiments, the bead capture site or the bead capture chamber further comprise a curved bead capture pocket and a bead capture channel. In some embodiments, the bead capture pocket is droplet shaped. In some embodiments, at least one of the wash valves, entrance valve, exit valves, sealing valves, and isolation valves are addressable. In some embodiments, the cell capture chamber and the bead capture chamber are configured to allow laminar flow to the bead capture chamber when buffer is introduced to the bead capture chamber. In some embodiments, the bead capture chamber and the cell capture chamber are separated by a channel with a distance of 20-40 microns. In some embodiments, the bead capture site comprises a bead capture channel at the bottom of said bead capture site, wherein the bead capture channel has a rectangular shape. In some embodiments, the opening of the bead capture channel is smaller than the diameter of the bead. In some embodiments, the bead capture channel allows fluid flow into and out of said bead capture channel while retaining the bead in the channel or capture site. In some embodiments, the interior of the device (e.g., one or more of channels or chambers) are coated with a material (e.g., protein or surfactant) that prevents nucleic acids (e.g., RNA) from adhering to the device. In some embodiments, the material is bovine serum albumin (BSA) or Pluronic® F108 Block Copolymer Surfactant (difunctional block copolymer surfactant terminating in primary hydroxyl groups).

Further embodiments provide a system, comprising: a) the devices described herein; and b) computer software configured to obtain an image of the device or a subcomponent thereof and calculate one or more parameters of interest for the device (e.g., number of cells in the chambers, number of live cells in the chambers, intensity of fluorescence signal, presence of contamination with unwanted cells or debris, or size of cells in the chambers). In some embodiments, the system further comprises one or more of a computer processor, a camera, a display system, lysis buffer, beads, a plurality of control mRNA sequences, and/or analysis reagents. In some embodiments, the beads are bar-coded.

Further embodiments provide a method of analyzing cells, comprising: a) contacting the system described herein with a plurality of cells under conditions such that the cells are isolated in the single cell capture chambers; and b) analyzing one or more parameters of the cells. In some embodiments, the cells are eukaryotic cells, prokaryotic cells, immortalized cells, pluripotent cells, or primary cells. In some embodiments, the cells are cancer cells (e.g., circulating tumor cells). In some embodiments, the cells are at concentration of 0 to 200,000 cells/ml prior to the contacting. In some embodiments, the contacting comprises the steps of closing the sealing valve distal to the bead capture chamber; loading the cells; opening the sealing valve distal to the bead capture chamber; loading a plurality of the beads; and closing the sealing valves. In some embodiments, the method further comprises the step of washing the chamber to remove uncaptured cells or debris prior to or after the step of loading a plurality of the beads. In some embodiments, the analyzing comprises determining one or more parameters of interest (e.g., number of cells in the chambers, number of live cells in the chambers, and size of cells in the chambers). In some embodiments, the method further comprises the step of lysing the cells in the cell capture chamber. In some embodiments, the nucleic acids from the lysed cells are attached to the bead in the bead capture chambers or the cell capture chamber. In some embodiments, the lysing step comprises the steps of adding lysis buffer to the bead capture chamber, closing the sealing valves and the entrance valve, and agitating the device. In some embodiments, lysis buffer is introduced such that laminar flow of the lysis buffer is obtained in the bead capture site.

In some embodiments, the method further comprises the step of contacting a plurality of different known barcoding mRNA sequences with different cell chambers or groups of cell chambers, wherein the barcoding mRNA sequences attach to the bead. In some embodiments, the barcoding mRNA sequences are introduced before or after cell lysis. In some embodiments, the barcoding mRNA is introduced at a concentration that does not saturate mRNA binding sites on the bead. In some embodiments, each cell chamber or group of cell chambers comprises a barcoding mRNA with a distinct sequence. In some embodiments, addressable valves are used to direct the barcoding mRNA sequences to cell chambers or groups of cell chambers. In some embodiments, the sequence of the barcoding mRNA sequences is different than the sequence of mRNA from the cells (e.g., the barcoding mRNAs do not include any human mRNA sequences). In some embodiments, plurality of different barcoding mRNA sequences comprises at least two distinct sequences per cell chamber or group of cell chambers. In some embodiments, the beads are removed from the device and subjected to further analysis (e.g., sequencing analysis, hybridization analysis, or amplification analysis). In some embodiments, the further analysis comprises determining the sequence of said barcoding mRNA in order to identify the cell chamber or group of cell chambers that a bead originated in.

Additional embodiments will be apparent to persons skilled in the relevant art based on the teachings contained herein.

DEFINITIONS

Figure 1:
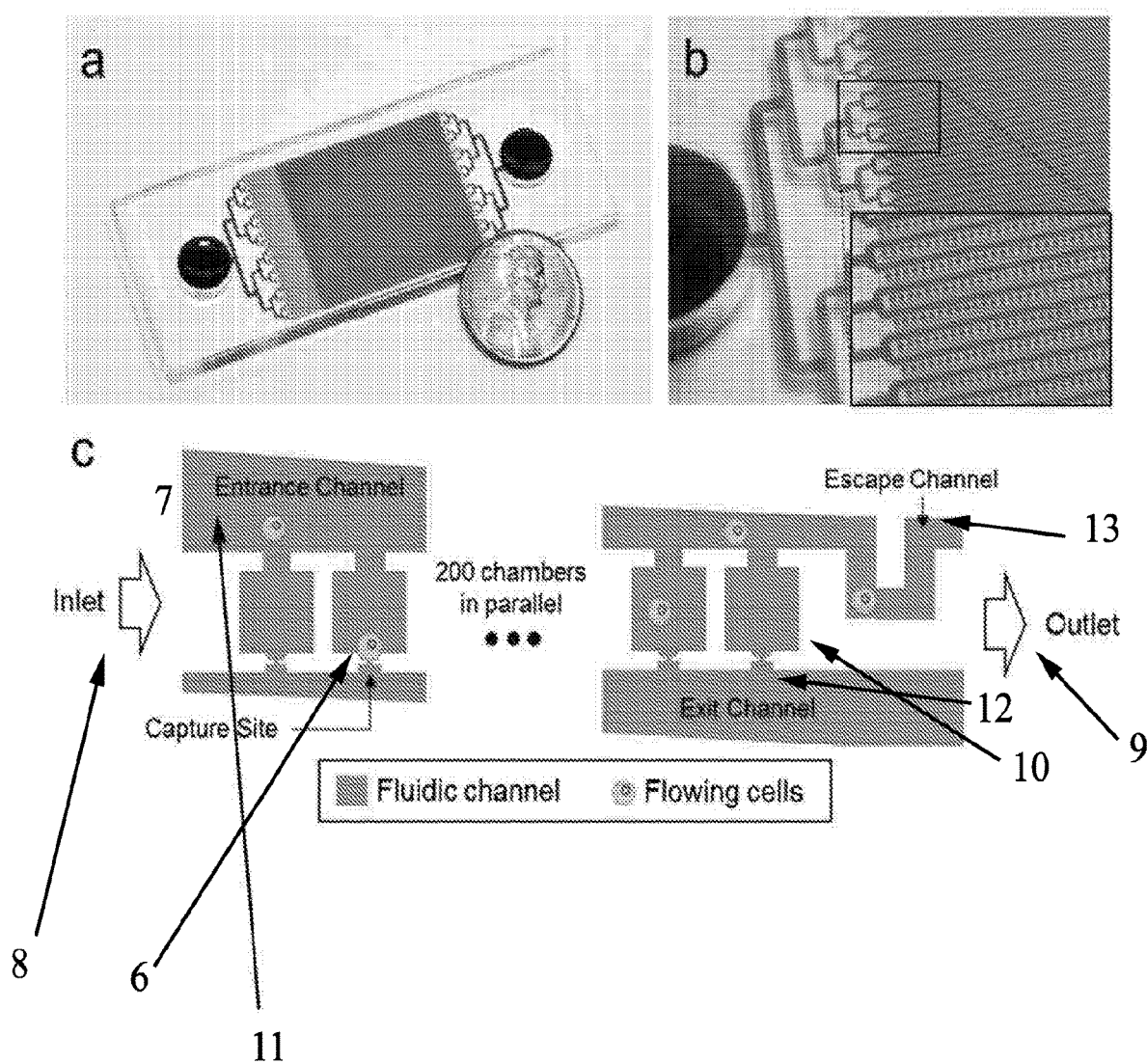
FIG. 1 shows an overview of an exemplary high-throughput single cell culture chip (a) Photograph of a chip with 12,800 single cell chambers. (b) Close-up photograph of the branching channels and single cell chambers. (c) Schematic of a single branch channel with 200 single cell chambers. (d) Schematic of a whole device with specified structure height. (e) Microscopic picture of single-cells captured in the well arrays. (Scale bar: 100 µm)
Figure 1:
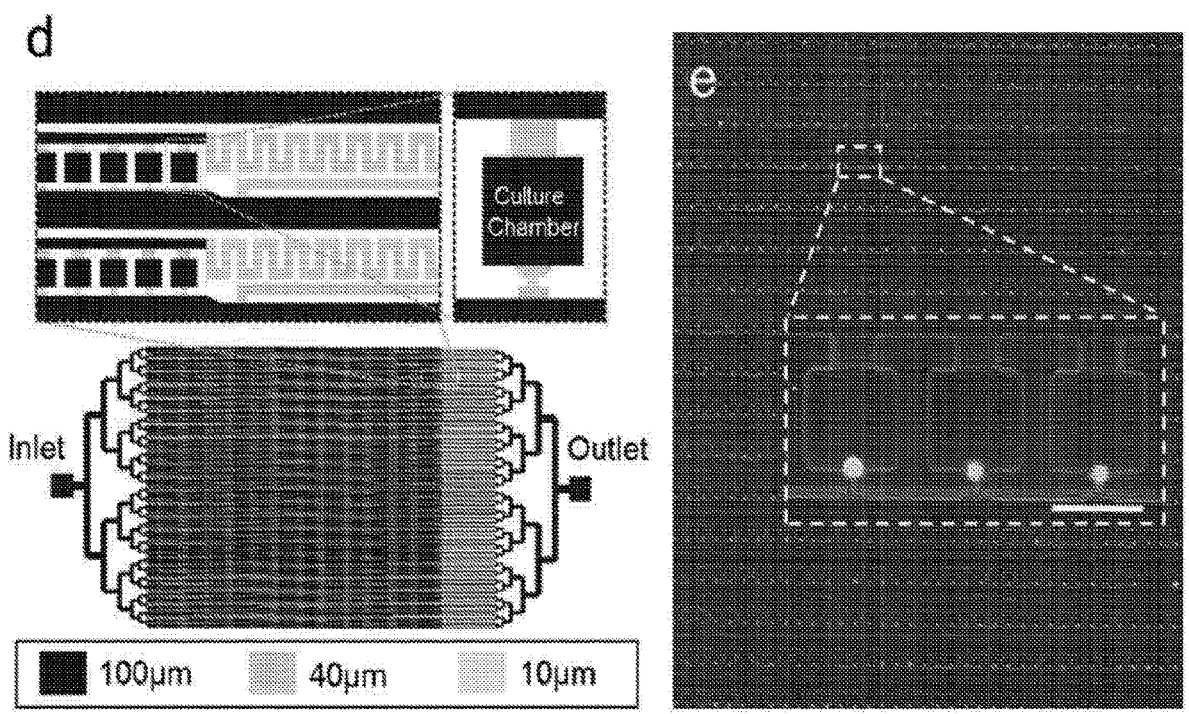

To facilitate an understanding of the present disclosure, a number of terms and phrases are defined below:

As used herein, the term "adherent culture chamber" refers to a well or chamber configured for cells to adhere to. In some embodiments, adherent culture chambers are adherent due to the surface material or coating.

As used herein, the term "suspension culture chamber" refers to a chamber or well that cells are unable to adhere to. In some embodiments, the surface of the suspension culture chamber is coated with a material that prevents or repels cells (e.g., polyHEMA).

The term "sample" is used in its broadest sense. On the one hand it is meant to include a specimen or culture. On the other hand, it is meant to include both biological and environmental samples. A sample may include a specimen of synthetic origin.

As used herein, the term "cell" refers to any eukaryotic or prokaryotic cell (e.g., bacterial cells such as *E. coli*, yeast cells, mammalian cells, avian cells, amphibian cells, plant cells, fish cells, and insect cells), whether located in vitro or in vivo.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

DETAILED DESCRIPTION OF THE DISCLOSURE

The present disclosure relates to systems and methods for cell (e.g., whole cell) analysis. In particular, the present disclosure relates to single cell genomic analysis (e.g., gene expression analysis).

In some embodiments, provided herein are devices, systems, and methods for single cell analysis. Such devices, systems, and methods meet an unmet need for analysis at the single cell level.

The devices described herein provide a variety of advantages over existing devices. For example, the devices provide robust and high single cell capture rate (e.g., ~75%) using a passive capture method. In some embodiments, the devices also provide high-density cell chamber spacing, saving imaging time over a large area. In some embodiments, devices provide wide cell size capture ranges from 10-40 μm, although other ranges are specifically contemplated. Many commercially available cell capture systems like the Fluidigm C1 capture only a certain size of cells.

In some embodiments, the devices and systems described herein provide automatic analysis that enables easy assay readout from thousands of single cells. The readout parameters include, for example, the number of cells inside each micro-well, the size of the captured single-cell, and the size of the cell sphere. The use of automated analysis also avoids the potential variance and bias created from manual readout.

In addition, whole transcriptome analysis allows users to learn the whole picture of gene signatures instead of a selected number of genes from PCR. The devices described herein provide high cell capture efficiency when handling small number of cells (e.g., at least 65% with 50 cells loaded) and low bead consumption per assay (e.g., only 2000-3000 beads needed for 800 chamber chip) compared to droplet and micro-well technologies.

The devices and systems described herein provide the capability to check the cell/bead capture condition for quality control and selective bead retrieval for analysis, which is difficult to achieve in droplet systems. The quality control option is particularly useful when analyzing clinical samples. For example, clinical samples like CTCs are frequently contaminated with red blood cells. The inspection capability allows a user to see if the chamber is thoroughly washed.

Furthermore, the systems described herein provide low reagent consumption compared to traditional tube processing methods and high throughput (e.g., at least 800 chambers per chip) compared to tube processing methods. The devices described herein further provide the option for selective bead retrieval to analyze the cells of interests.

Exemplary devices, systems, and methods are described herein.

I. Devices

For example, in some embodiments, provided herein are microfluidic devices comprising a highly parallel channel structure for throughput scaling. In some embodiments, single-cells are captured in micro-wells when they flow into the micro-wells and block the capture site.

Exemplary devices are shown in the Figures. FIG. 1 shows an exemplary cell capture device. The device comprises inlet 8 and outlet 9 channels connecting a plurality of parallel fluid channels 10. The fluid channels 10 comprise entrance 11 and exit 12 channels and cell capture chamber 6 and escape port 13. In some embodiments, the single cell chambers further comprise a deformable entrance and/or exit valve 1 (FIG. 13) distal and/or proximal to said single cell chamber. In some embodiments, the entrance valve has an opening of at least 35 μm (or smaller depending on bead size) and the exit valve has an opening of at least 15 μm. In some embodiments, the entrance channel 11 is tapered smaller in the direction of fluid flow and the exit channel 12 is tapered larger in the direction of fluid flow. In some embodiments, the entrance 11 and exit 12 channels have a height of at least 5 times (e.g., at least 10 times) the height of the single cell chambers 4. In some embodiments, the device comprises at least 500 (e.g., at least 500, at least 1000, at least 5000, or at least 10,000) single cell chambers. The parallel channel structure allows for chamber scaling with flow circuit design. The lower flow resistance along the entrance and exit channel compared to resistance along the capture chambers obtained by multilayer fabrication and increased width and height in channel design enhances fluid flow. In addition, the tapered entrance and exit channel maintain flow velocity and prevent cell adhesion to the substrate. The device design is highly adaptive to different capture chamber designs and allows cell and bead retrieval without clogging issues.

Figure 18:
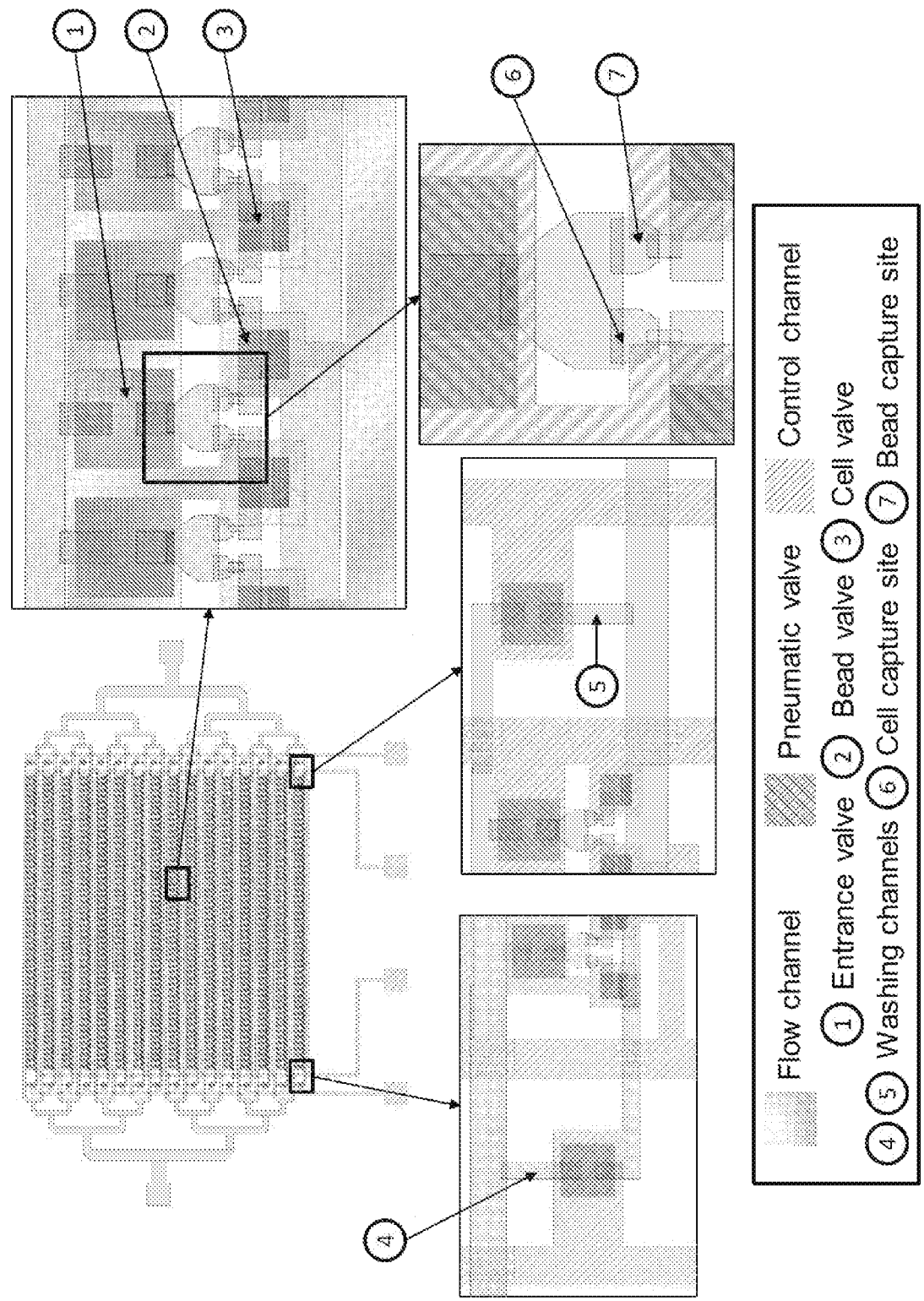
FIG. 18 shows design of hydro-Seq single chamber model. (a) A close up view of the multiple bead cell pairing chamber connected with the scaling structure. (b and c) The wash channel added to the two ends of the entrance and exit channels.
Figure 19:
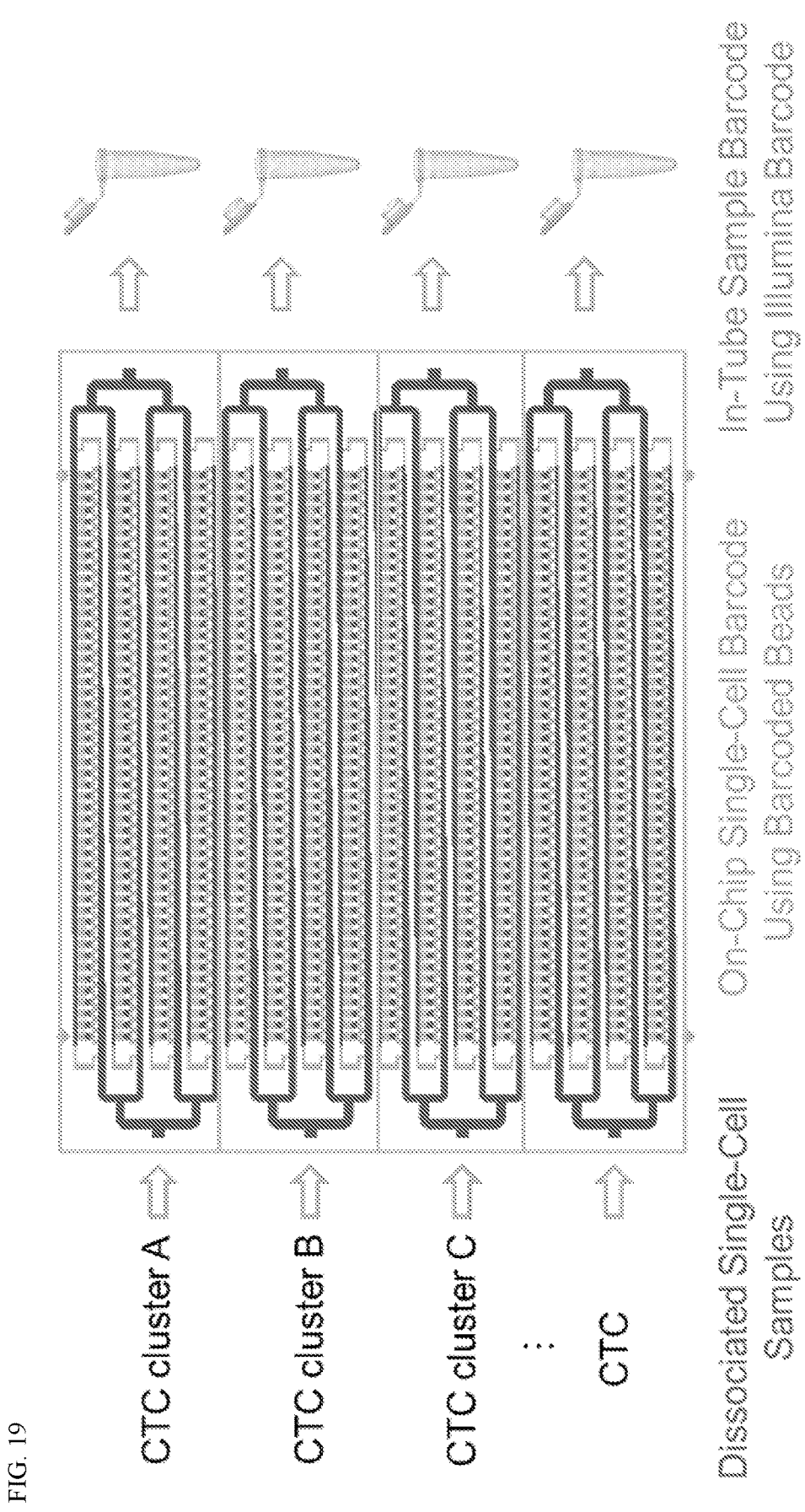
FIG. 19 shows on-chip multiplexing to enable handling multiple samples using a single chip.

In some embodiments, devices further comprise wash channels 4 and 5 (See e.g., FIG. 18) in fluid communication with the entrance and exit channels. In some embodiments, wash channels 4 and 5 comprise integrated wash valves to control opening and closing of the wash channels. FIG. 18 further shows sealing valves (e.g., bead valve 2 and cell valve 3), and bead capture site 7.

Figure 14:
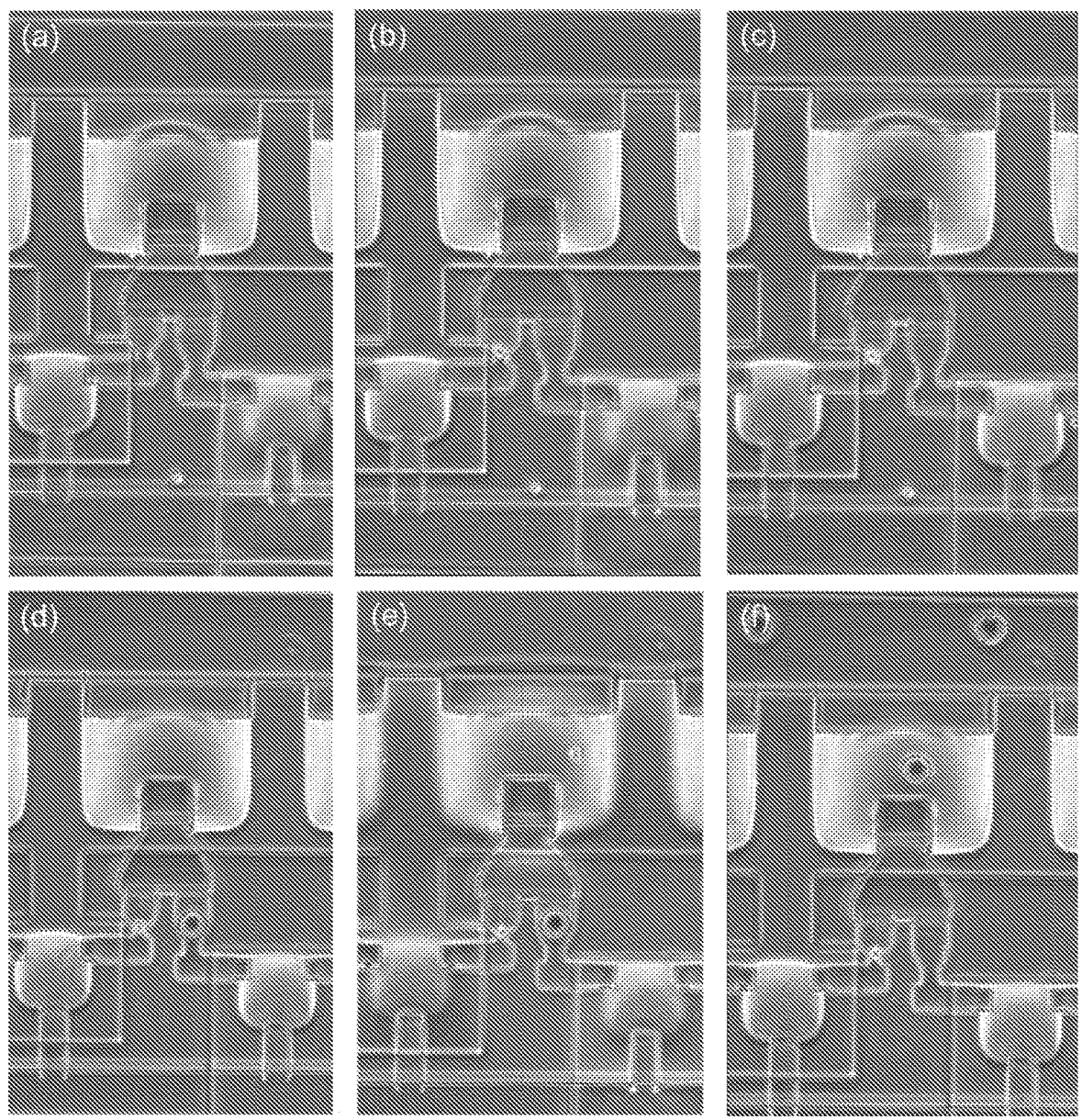
FIG. 14 shows single chamber bead-cell-pairing operation flow. (a) Close the valve after the bead capture site to block the flow path. (b) Load cell suspension solution into device. Cells are captured at the cell capture by capture site blocking. (c) Open the valve after the bead capture site to restore the flow path. (d) Load the bead suspension and capture a single bead at the bead capture site. (e) Close all the valves and perform cell lysis. (f) After incubation, reverse the flow and beads can be collected from the inlet for downstream process and sequencing. (g) schematic of bead capture and lysis. Bead capture valve is closed during sample loading. The smaller red blood cells flow through the capture until a larger cell (larger than 12 µm) blocks the channel for cell capture. After cell capture, the bead capture valve is then opened to wash the contaminations away. After removing contaminations in the chamber, the bead is then loaded for pairing. Lysis buffer is into the chamber while cell remains in the dead volume. After closing all the valves, the cell is pushed to the middle of the chamber for lysis and mRNA capture. By opening all the valves and introducing a back flow, the beads can be retrieved to the inlet for downstream preparation.
Figure 14:
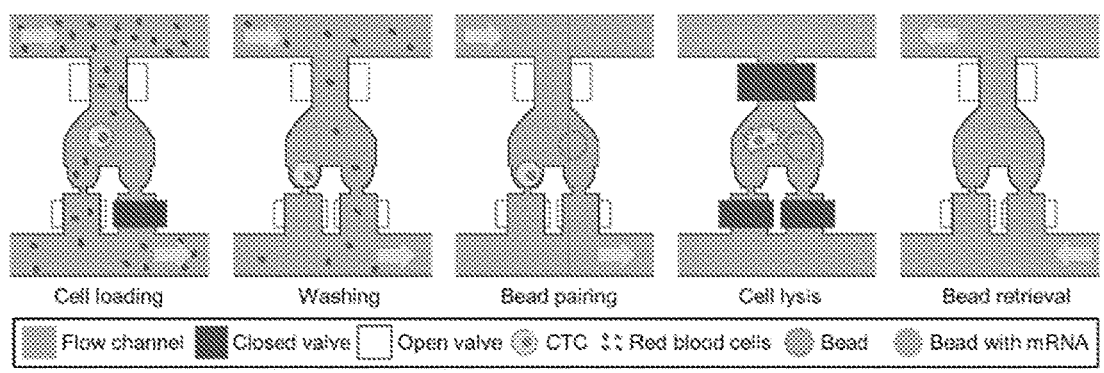
Figure 15:
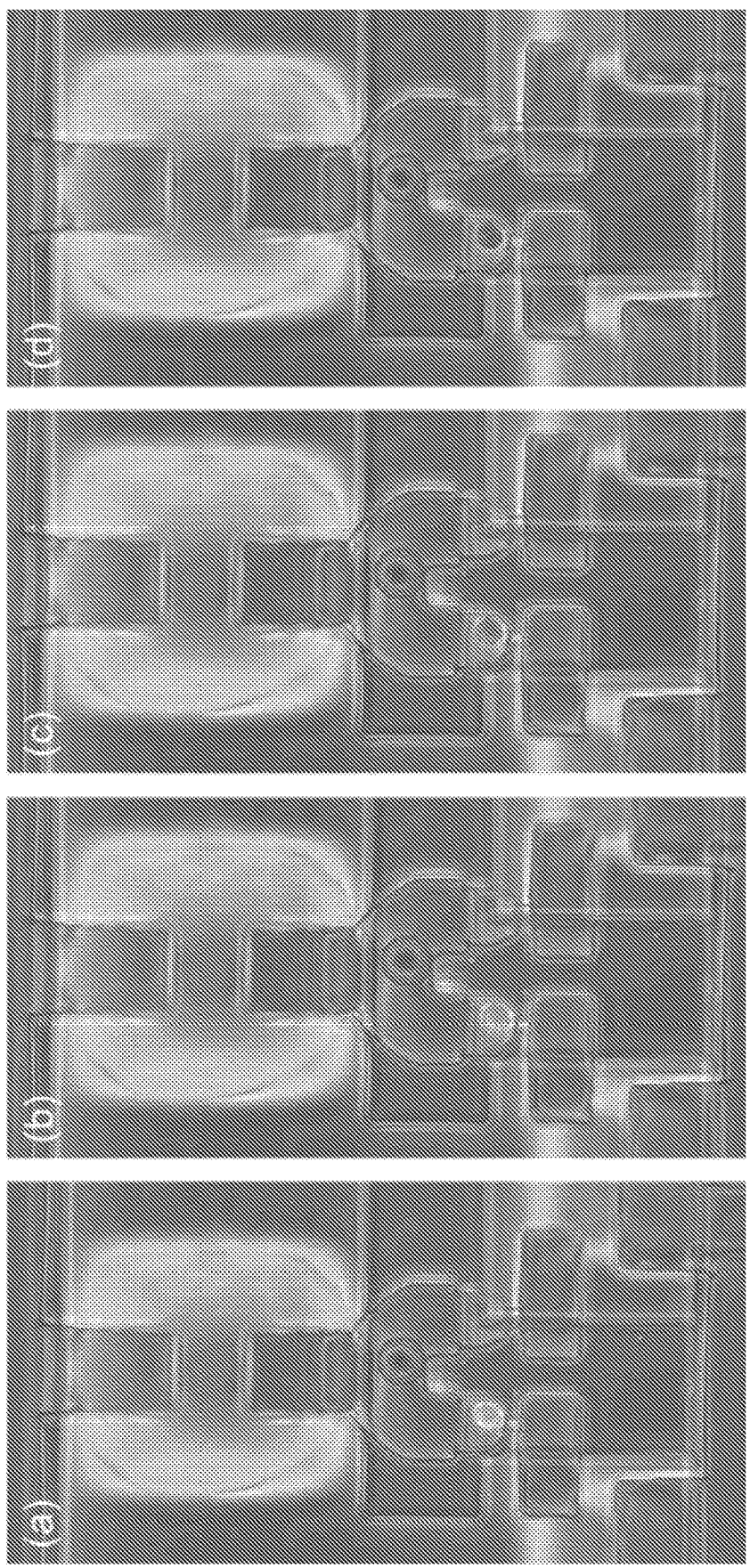
FIG. 15 shows cell lysis in hydro-Seq single chamber design. (a) A viable cell with red fluorescence was captured at the capture site. (b) After introducing cell lysis buffer for several seconds, morphology and color change can be observed. (c) The red fluorescent signal decayed after the cell membrane was compromised. (d) The red fluorescence signal drops to background value, indicating the fluorescent protein is fully released into the chamber.
Figure 16:
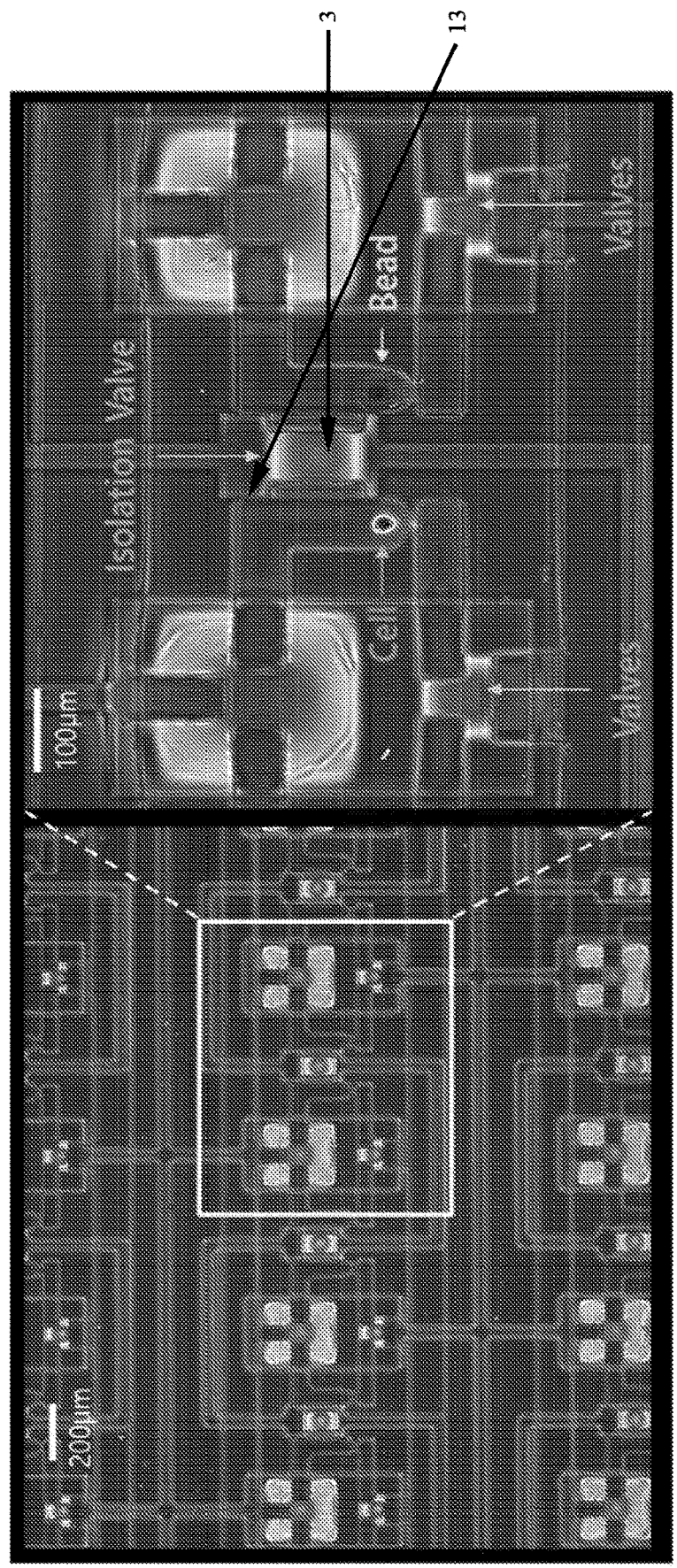
FIG. 16 shows hydro-Seq dual chamber bead-cell-pairing design.
Figure 20:
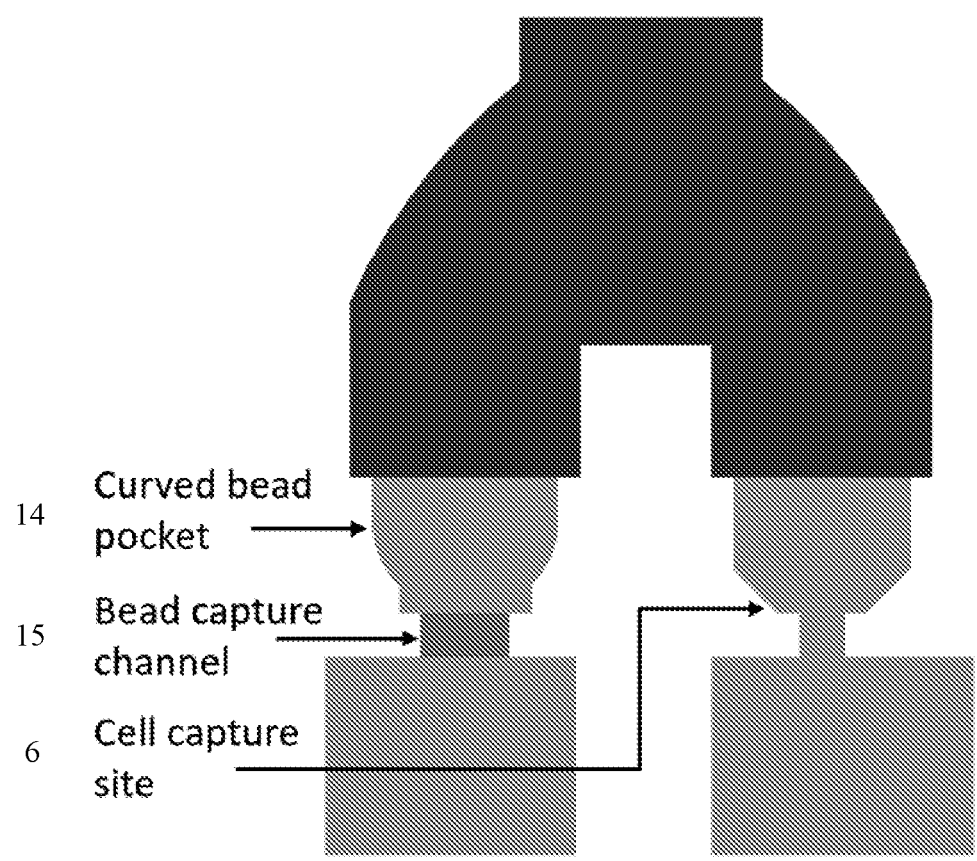
FIG. 20 shows bead capture site design.

In some embodiments, the device furthers comprise a plurality of bead capture chambers or sites 7 in parallel with the single cell capture chambers. FIGS. 13-19 show devices with bead capture chamber 7 and cell capture chamber 6. In some embodiments, the bead capture chambers 7 and the single cell capture chambers 6 are separated by a channel 13 (FIG. 16). In some embodiments, the channel comprises an isolation or cell valve 3 (FIG. 16) between the bead capture chamber 7 and the single cell capture chamber 6 (FIG. 16). In some embodiments, the cell capture site and the bead capture site comprise sealing valves 2 and 3 proximal to the cell capture site and distal to the bead capture site. In some embodiments, the bead capture chambers further comprise a curved bead capture pocket 14 and bead capture channel 15 (FIG. 20). In some embodiments, the bead capture pocket 14 is droplet shaped. The droplet shape minimizes dead volume during loading and washing (FIGS. 14 and 15). In some embodiments, the cell capture site and bead capture site are separated by a wall (e.g., at least 20 μm thick and 20 μm long). In some embodiments, the wall prevents the cell from leaving the cell capture site during valve operation (e.g., during valve closure, the flow pumped out can push the cells back to chamber and potentially be lost when the bead capture site is open). In some embodiments, the cell capture chamber and the sealing valves overlap at least 20% into the valve area to prevent bead clogging and improve capture performance. In some embodiments, the bead capture sites and the cell capture sites alternate to allow valve sharing. In some embodiments, at least one of the wash valves, entrance valve, exit valves, sealing valves, and isolation valves are addressable.

The use of separate cell capture site and bead capture site, along with an optional curved bead capture pocket minimizes flow leakage after bead capture. The use of a valve controlled bead capture site enables sequential loading of cells and beads and prevention of sample contamination. In some embodiments, devices utilize valve sharing with neighboring chambers (See e.g., FIGS. 18 and 19) to minimize chamber area consumption and maximize area efficiency In some embodiments, valve multiplexing allows for multiplex sample processing on the same chip sharing valve control with multiple inlets and outlets. The valve multiplexor is exemplified in FIG. 25. The valve multiplexor allows for a plurality of different assays to be performed on one chip.

In some embodiments, devices comprise double or multiple capture sites to capture cells for co-culture assay, enabling the study of cell-to-cell interaction and cell engulfment.

In some embodiments, to improve the throughput, multiple layers of the presented capture structure are stacked in a single chip to enable more single cell analysis on chip.

In some embodiments, different kinds of chemical sensing beads are incorporated into the device to study the property of single cells. For instance, ELISA beads can be used to study the single cell secretion analysis.

The present disclosure is not limited to particular methods for fabricating microfluidic devices. In some embodiments, devices are made from poly-dimethylsiloxane (PDMS).

In some embodiments, layers are made by supplying a negative "master" and casting a castable material over the master. Castable materials include, but are not limited to, polymers, including epoxy resins, curable polyurethane elastomers, polymer solutions (e.g., solutions of acrylate polymers in methylene chloride or other solvents), curable polyorganosiloxanes, and polyorganosiloxanes which predominately bear methyl groups (e.g., polydimethylsiloxanes ("PDMS")). Curable PDMS polymers are well known and available from many sources. Both addition curable and condensation-curable systems are available, as also are peroxide-cured systems. All of these PDMS polymers have a small proportion of reactive groups which react to form crosslinks and/or cause chain extension during cure. Both one part (RTV-1) and two part (RTV-2) systems are available. Additional curable systems are preferred when biological particle viability is needed.

In some embodiments, transparent devices are desirable. Such devices may be made of glass or transparent polymers. PDMS polymers are well suited for transparent devices. A benefit of employing a polymer which is slightly elastomeric is the case of removal from the mold and the potential for providing undercut channels, which is generally not possible with hard, rigid materials. Methods of fabrication of microfluidic devices by casting of silicone polymers are well known. See, e.g. D. C. Duffy et al., "Rapid Prototyping of Microfluidic Systems in Poly(dimethylsiloxane)," Analytical Chemistry 70, 4974-4984 (1998). See also, J. R. Anderson et al., Analytical Chemistry 72, 3158-64 (2000); and M. A. Unger et al., Science 288, 113-16 (2000), each of which is herein incorporated by reference in its entirety.

In some embodiments, in order to facilitate cell culture assays, the substrate is modified to create different culture environments with various assay applications. In some embodiments, for suspension culture, polyHEMA coated glass slide or F108 coated PDMS is used. In some embodiments, for adherent culture, glass slide or polystyrene is used. In some embodiments, extracellular matrix such as laminin, collagen, and fibronectin is coated to create the micro-environment specific for a given assay.

In some embodiments, the cell capture chamber is designed for different assay applications including but not limited to sphere culture assay, migration assays, ELISA assays, co-culture assays, and chemical/metabolite sensing assays.

In some embodiments, fluids are supplied to the device by any suitable method. Fluids may, for example, be supplied from syringes, from microtubing attached to or bonded to the inlet channels, etc.

Fluid flow may be established by any suitable method. For example, external micropumps suitable for pumping small quantities of liquids are available. Micropumps may also be provided in the device itself, driven by thermal gradients, magnetic and/or electric fields, applied pressure, etc. All these devices are known to the skilled artisan. Integration of passively-driven pumping systems and microfluidic channels has been proposed by B. H. Weigl et al., Proceedings of MicroTAS 2000, Enshede, Netherlands, pp. 299-302 (2000).

In other embodiments, fluid flow is established by a gravity flow pump, by capillary action, or by combinations of these methods. A simple gravity flow pump consists of a fluid reservoir either external or internal to the device, which contains fluid at a higher level (with respect to gravity) than the respective device outlet. Such gravity pumps have the deficiency that the hydrostatic head, and hence the flow rate, varies as the height of liquid in the reservoir drops. For many devices, a relatively constant and non-pulsing flow is desired.

To obtain constant flow, a gravity-driven pump as disclosed in published PCT application No. WO 03/008102 A1 (Jan. 18, 2002), herein incorporated by reference, may be used. In such devices, a horizontal reservoir is used in which the fluid moves horizontally, being prevented from collapsing vertically in the reservoir by surface tension and capillary forces between the liquid and reservoir walls. Since the height of liquid remains constant, there is no variation in the hydrostatic head.

Flow may also be induced by capillary action. In such a case, fluid in the respective outlet channel or reservoir will exhibit greater capillary forces with respect to its channel or reservoir walls as compared to the capillary forces in the associated device. This difference in capillary force may be brought about by several methods. For example, the walls of the outlet and inlet channels or reservoirs may have differing hydrophobicity or hydrophilicity. Alternatively, the cross-sectional area of the outlet channel or reservoir is made smaller, thus exhibiting greater capillary force (See e.g., above description of channel sizes optimized for fluid flow.

Additional embodiments provide systems and kits comprising the devices described herein and one or more additional components. In some embodiments, systems comprise computer software configured to obtain an image of the device and calculate one or more parameters of interest (e.g., number of cells in the chambers, number of live cells in the chambers, and size of cells in the chambers) for the device.

In some embodiments, systems further comprise one or more of a computer processor, a camera, a display system, lysis buffer, beads (e.g., bar-coded beads), or analysis reagents.

II. Methods

In some embodiments, the present disclosure provides a method of analyzing cells using the devices and systems described herein. In some embodiments, cells are loaded (e.g., at a concentration of 1 to 200,000 (e.g., 50,000) cells/ml) and cultured in the single cell capture chambers of the device. The present disclosure is not limited to particular cells (e.g., prokaryotic (e.g., bacterial) cells or eukaryotic (e.g., single celled organisms, mammalian cells, primary cell culture, immortalized cells, pluripotent cells, etc.) may be utilized. In some embodiments, cells are cancer cells. In some embodiments, cells are loaded by closing the valve distal to the bead capture chamber; loading the cells; opening the valve distal to the bead capture chamber; loading a plurality of the beads; and closing the valves.

In some embodiments, cells in chamber are subjected to drug screening, immunostaining, or cell morphology analysis prior to lysis. In some embodiments, cells are imaged in the chamber. In some embodiments, following lysis, cells are analyzed (e.g., for levels of gene expression or other parameters).

In some embodiments, beads are barcoded to track nucleic acids to a specific cell. In some embodiments, known different mRNA sequences are added to each cell or row/column. This allows one to identify the location (column/row) of the bead after analysis (e.g., by sequencing the barcoding mRNA). For example, in some embodiments, a plurality of different known barcoding mRNA sequences are introduced into different cell chambers or groups of cell chambers, wherein the barcoding mRNA sequences attach to the bead (e.g., using addressable valves). In some embodiments, the barcoding mRNA sequences are introduced prior to or after to cell lysis. In some embodiments, the barcoding mRNA is introduced at a concentration that does not saturate mRNA binding sites on the bead. In some embodiments, each cell chamber or group of cell chambers comprises a barcoding mRNA with a distinct sequence. In some embodiments, the sequence of the barcoding mRNA sequences is different than the sequence of mRNA from the cells (e.g., the barcoding mRNAs do not include any human mRNA sequences). In some embodiments, plurality of different barcoding mRNA sequences comprises at least two distinct sequences per cell chamber or group of cell chambers.

After culture, cells are analyzed (e.g., to determine number of cells in the chambers, number of live cells in the chambers, or size of cells in the chambers). In some embodiments, analysis is Contrast-limited adaptive histogram equalization (CLAHE) with k-means cluster algorithm for cell identification and analysis. In some embodiments, the method further comprises the step of lysing the cells in the cell capture chamber (e.g., using lysis buffer or pico-second laser with Au—Pd or CNT coated substrate). In some embodiments, nucleic acids from the lysed cells are attached to the bead in the cell capture or bead capture chambers. In some embodiments, the beads are removed from said device and subjected to further analysis (e.g., sequencing analysis, hybridization analysis, or amplification analysis).

The present disclosure is not limited to particular types of analyses. Examples include, but are not limited to, screening cells for gene expression at the mRNA or protein level (e.g., via reporter genes in live cells or molecular analysis); screening compounds (e.g., drugs) for their effect on cell growth, cell death, viral infectivity, or gene expression; screening viruses for infectivity (e.g., plaque formation); epigenome analysis (e.g., methylation status of genes and/or promoters), protein analysis (e.g., immunoassays such as e.g., single cell Western blot and mass spectrometry analysis), copy-number variations (CNVs) assays, and screening for mutations or polymorphisms (e.g., SNPs).

The present disclosure is not limited to particular analysis methods. Examples include, but are not limited to, sequencing analysis, hybridization analysis, and amplification analysis. Exemplary analysis methods are described herein.

A variety of nucleic acid sequencing methods are contemplated for use in the methods of the present disclosure including, for example, chain terminator (Sanger) sequencing, dye terminator sequencing, and high-throughput sequencing methods. Many of these sequencing methods are well known in the art. See, e.g., Sanger et al., Proc. Natl. Acad. Sci. USA 74:5463-5467 (1997); Maxam et al., Proc. Natl. Acad. Sci. USA 74:560-564 (1977); Drmanac, et al., Nat. Biotechnol. 16:54-58 (1998); Kato, Int. J. Clin. Exp. Med. 2:193-202 (2009); Ronaghi et al., Anal. Biochem. 242:84-89 (1996); Margulies et al., Nature 437:376-380 (2005); Ruparel et al., Proc. Natl. Acad. Sci. USA 102:5932-5937 (2005), and Harris et al., Science 320:106-109 (2008); Levene et al., Science 299:682-686 (2003); Korlach et al., Proc. Natl. Acad. Sci. USA 105:1176-1181 (2008); Branton et al., Nat. Biotechnol. 26(10):1146-53 (2008); Eid et al., Science 323:133-138 (2009); each of which is herein incorporated by reference in its entirety.

Next-generation sequencing (NGS) methods share the common feature of massively parallel, high-throughput strategies, with the goal of lower costs in comparison to older sequencing methods (see, e.g., Voelkerding et al., *Clinical Chem.*, 55: 641-658, 2009; MacLean et al., *Nature Rev. Microbiol.*, 7: 287-296; each herein incorporated by reference in their entirety). NGS methods can be broadly divided into those that typically use template amplification and those that do not. Amplification-requiring methods include pyrosequencing commercialized by Roche as the 454 technology platforms (e.g., GS 20 and GS FLX), the Solexa platform commercialized by Illumina, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen, Oxford Nanopore Technologies Ltd., Life Technologies/Ion Torrent, and Pacific Biosciences, respectively.

Other emerging single molecule sequencing methods include real-time sequencing by synthesis using a VisiGen platform (Voelkerding et al., *Clinical Chem.*, 55: 641-58, 2009; U.S. Pat. No. 7,329,492; U.S. patent application Ser. No. 11/671,956; U.S. patent application Ser. No. 11/781,166; each herein incorporated by reference in their entirety) in which immobilized, primed DNA template is subjected to strand extension using a fluorescently-modified polymerase and florescent acceptor molecules, resulting in detectable fluorescence resonance energy transfer (FRET) upon nucleotide addition.

Illustrative non-limiting examples of nucleic acid hybridization techniques include, but are not limited to, in situ hybridization (ISH), microarray, and Southern or Northern blot. In situ hybridization (ISH) is a type of hybridization that uses a labeled complementary DNA or RNA strand as a probe to localize a specific DNA or RNA sequence in a portion or section of tissue (in situ), or, if the tissue is small enough, the entire tissue (whole mount ISH). DNA ISH can be used to determine the structure of chromosomes. RNA ISH is used to measure and localize mRNAs and other transcripts within tissue sections or whole mounts. Sample cells and tissues are usually treated to fix the target transcripts in place and to increase access of the probe. The probe hybridizes to the target sequence at elevated temperature, and then the excess probe is washed away. The probe that was labeled with either radio-, fluorescent- or antigen-labeled bases is localized and quantitated in the tissue using either autoradiography, fluorescence microscopy or immunohistochemistry, respectively. ISH can also use two or more probes, labeled with radioactivity or the other non-radioactive labels, to simultaneously detect two or more transcripts.

Different kinds of biological assays are called microarrays including, but not limited to: DNA microarrays (e.g., cDNA microarrays and oligonucleotide microarrays); protein microarrays; tissue microarrays; transfection or cell microarrays; chemical compound microarrays; and, antibody microarrays. A DNA microarray, commonly known as gene chip, DNA chip, or biochip, is a collection of microscopic DNA spots attached to a solid surface (e.g., glass, plastic or silicon chip) forming an array for the purpose of expression profiling or monitoring expression levels for thousands of genes simultaneously. The affixed DNA segments are known as probes, thousands of which can be used in a single DNA microarray. Microarrays can be used to identify disease genes or transcripts (e.g., those described in table 1) by comparing gene expression in disease and normal cells. Microarrays can be fabricated using a variety of technologies, including but not limiting: printing with fine-pointed pins onto glass slides; photolithography using pre-made masks; photolithography using dynamic micromirror devices; ink-jet printing; or, electrochemistry on microelectrode arrays.

Southern and Northern blotting is used to detect specific DNA or RNA sequences, respectively. DNA or RNA extracted from a sample is fragmented, electrophoretically separated on a matrix gel, and transferred to a membrane filter. The filter bound DNA or RNA is subject to hybridization with a labeled probe complementary to the sequence of interest. Hybridized probe bound to the filter is detected. A variant of the procedure is the reverse Northern blot, in which the substrate nucleic acid that is affixed to the membrane is a collection of isolated DNA fragments and the probe is RNA extracted from a tissue and labeled.

Nucleic acids may be amplified prior to or simultaneous with detection. Illustrative non-limiting examples of nucleic acid amplification techniques include, but are not limited to, polymerase chain reaction (PCR), reverse transcription polymerase chain reaction (RT-PCR), transcription-mediated amplification (TMA), ligase chain reaction (LCR), strand displacement amplification (SDA), and nucleic acid sequence based amplification (NASBA). Those of ordinary skill in the art will recognize that certain amplification techniques (e.g., PCR) require that RNA be reversed transcribed to DNA prior to amplification (e.g., RT-PCR), whereas other amplification techniques directly amplify RNA (e.g., TMA and NASBA).

The methylation levels of non-amplified or amplified nucleic acids can be detected by any conventional means. For example, in some embodiments, Methylplex-Next Generation Sequencing (M-NGS) methodology is utilized. In other embodiments, the methods described in U.S. Pat. Nos. 7,611,869, 7,553,627, 7,399,614, and/or 7,794,939, each of which is herein incorporated by reference in its entirety, are utilized. Additional detection methods include, but are not limited to, bisulfate modification followed by any number of detection methods (e.g., probe binding, sequencing, amplification, mass spectrometry, antibody binding, etc.) methylation-sensitive restriction enzymes and physical separation by methylated DNA-binding proteins or antibodies against methylated DNA (See e.g., Levenson, Expert Rev Mol Diagn. 2010 May; 10(4): 481-488; herein incorporated by reference in its entirety).

In some embodiments, gene expression or other protein analysis (e.g., detection of cell surface antigens) is performed using immunoassays or mass spectrometry.

Illustrative non-limiting examples of immunoassays include, but are not limited to: immunoprecipitation; Western blot; ELISA; immunohistochemistry; immunocytochemistry; flow cytometry; and, immuno-PCR. Polyclonal or monoclonal antibodies detectably labeled using various techniques known to those of ordinary skill in the art (e.g., colorimetric, fluorescent, chemiluminescent or radioactive) are suitable for use in the immunoassays. Immunoprecipitation is the technique of precipitating an antigen out of solution using an antibody specific to that antigen. The process can be used to identify protein complexes present in cell extracts by targeting a protein believed to be in the complex. The complexes are brought out of solution by insoluble antibody-binding proteins isolated initially from bacteria, such as Protein A and Protein G. The antibodies can also be coupled to sepharose beads that can easily be isolated out of solution. After washing, the precipitate can be analyzed using mass spectrometry, Western blotting, or any number of other methods for identifying constituents in the complex.

EXPERIMENTAL

Example 1

Design of the Highly Parallel Channel Structure for Throughput Scaling

Figure 2:
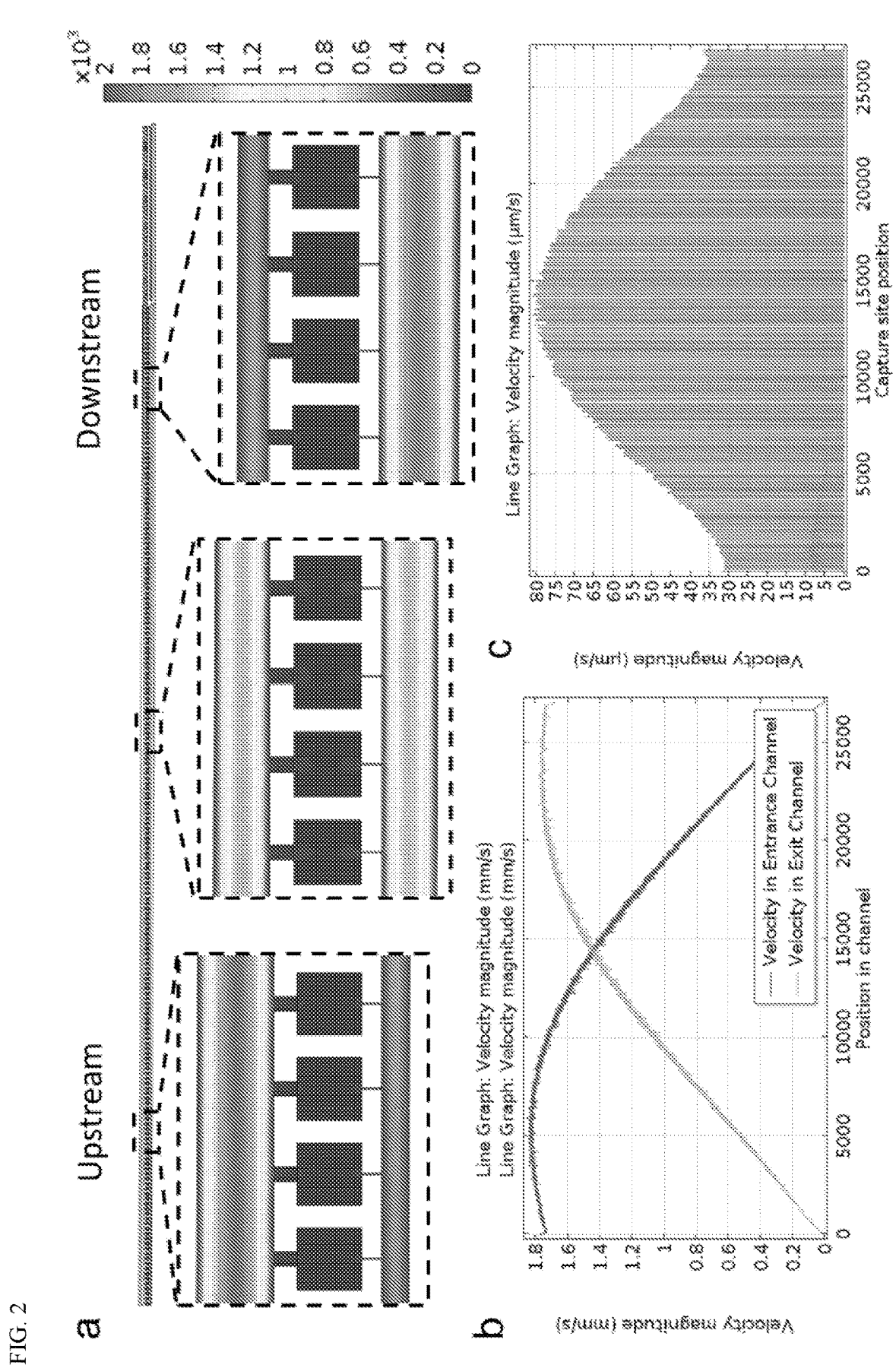
FIG. 2 shows a (a) Simulation of one branch channel with 50 Pa input pressure (unit: µm/min) (b) The tapered entrance and exit channel help maintain the constant flow rate at the upstream and midstream (c) Flow distribution across the 200 capture sites, showing higher flow rate at the midstream and lower flow rate at the upstream and downstream with ~65% difference from peak value.
Figure 3:
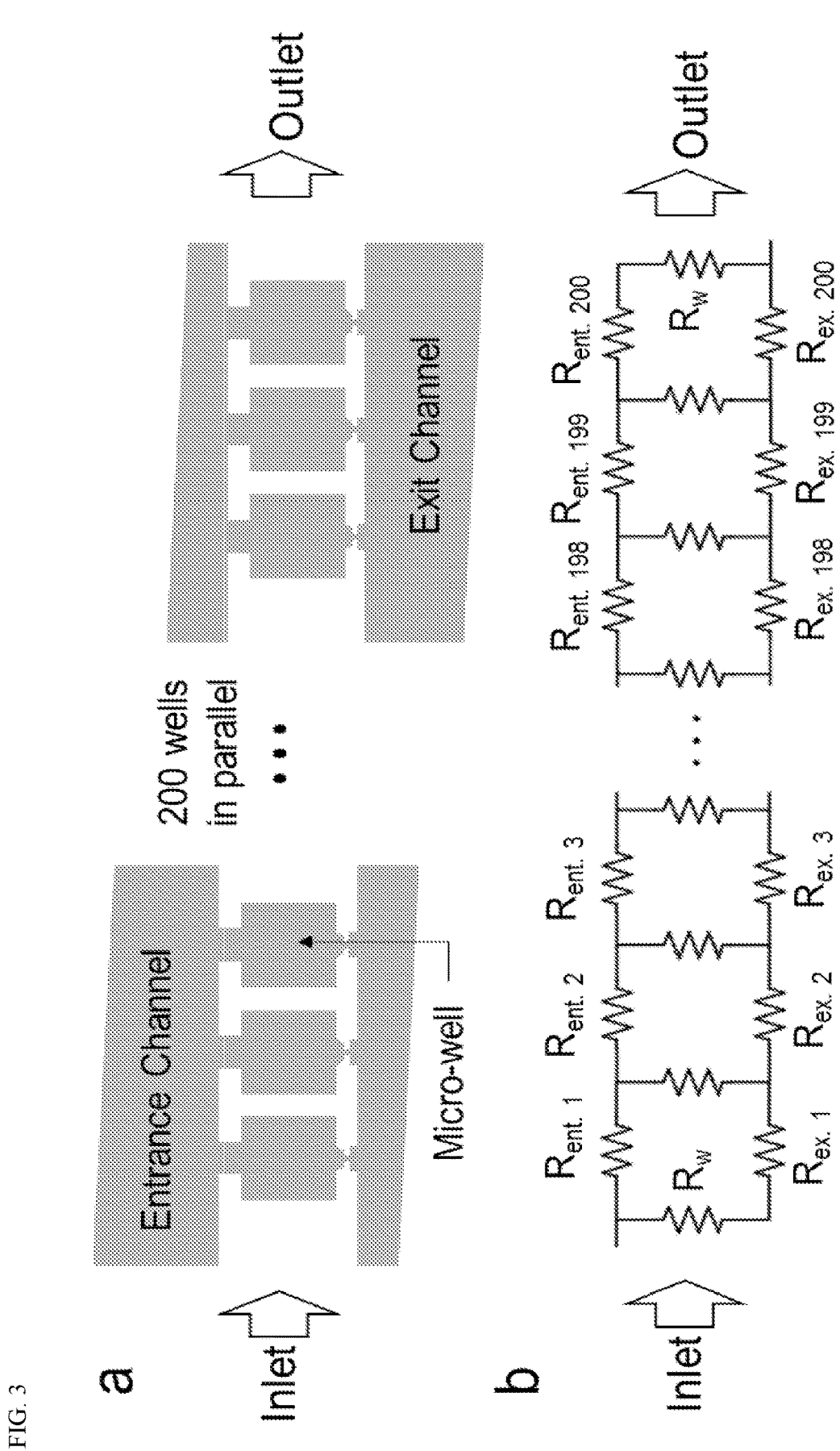
FIG. 3 shows fluidic circuit analogy for channel design. (a) Channel diagram of a single branch channel. (b) Equivalent electrical circuit diagram to the fluidic channel in (a). $R_{ent}$ is the unit resistance of an entrance channel segment between two neighboring wells.
Figure 4:
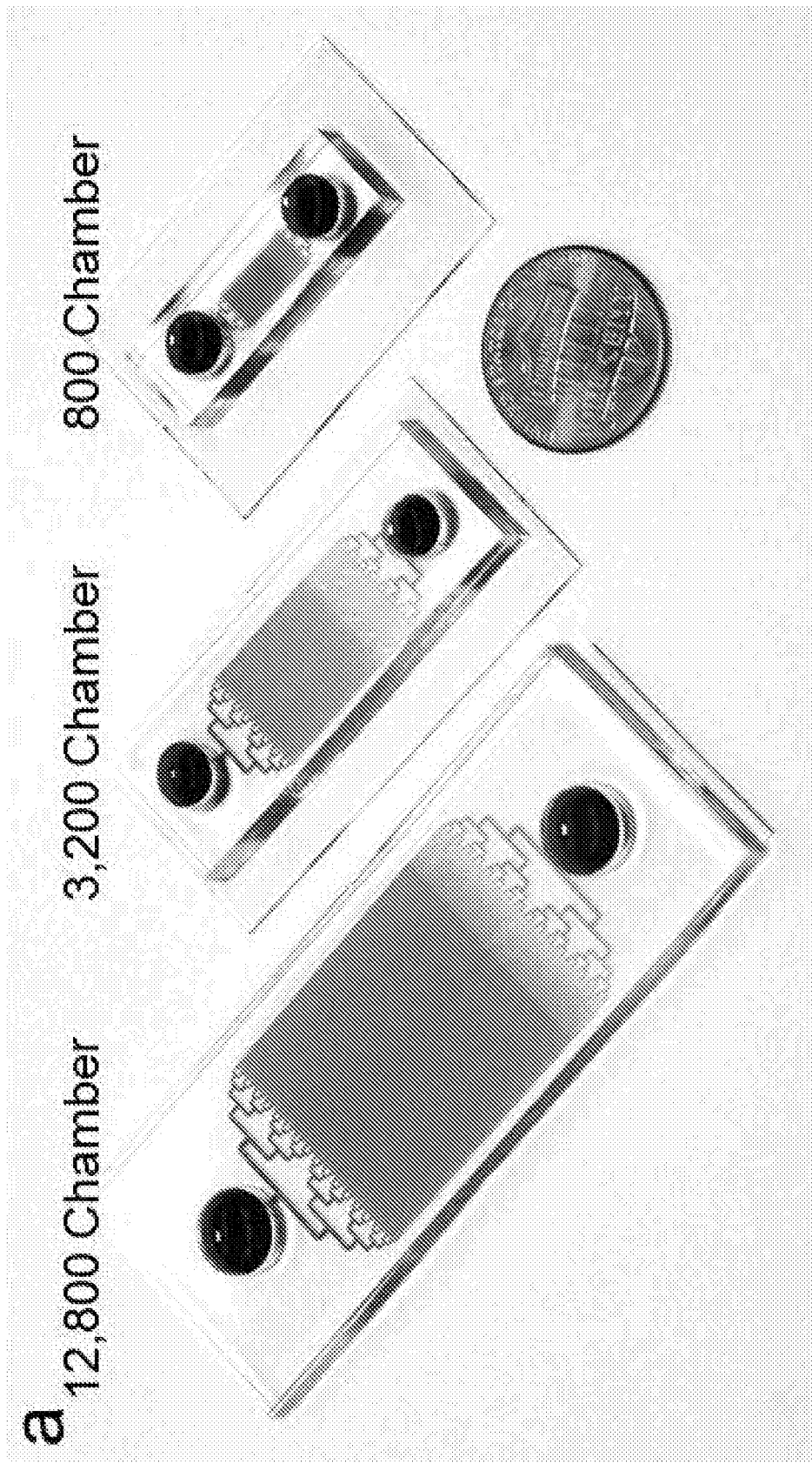
FIG. 4 shows (a) Picture of devices with 800 chambers, 3,200 chambers, and 12,800 chambers for single cell capture and culture (b) Cell capture distribution for the 800 chamber chip, showing similar capture distribution compared to the 12,800 chamber chip. (N=1 for each concentration)
Figure 4:
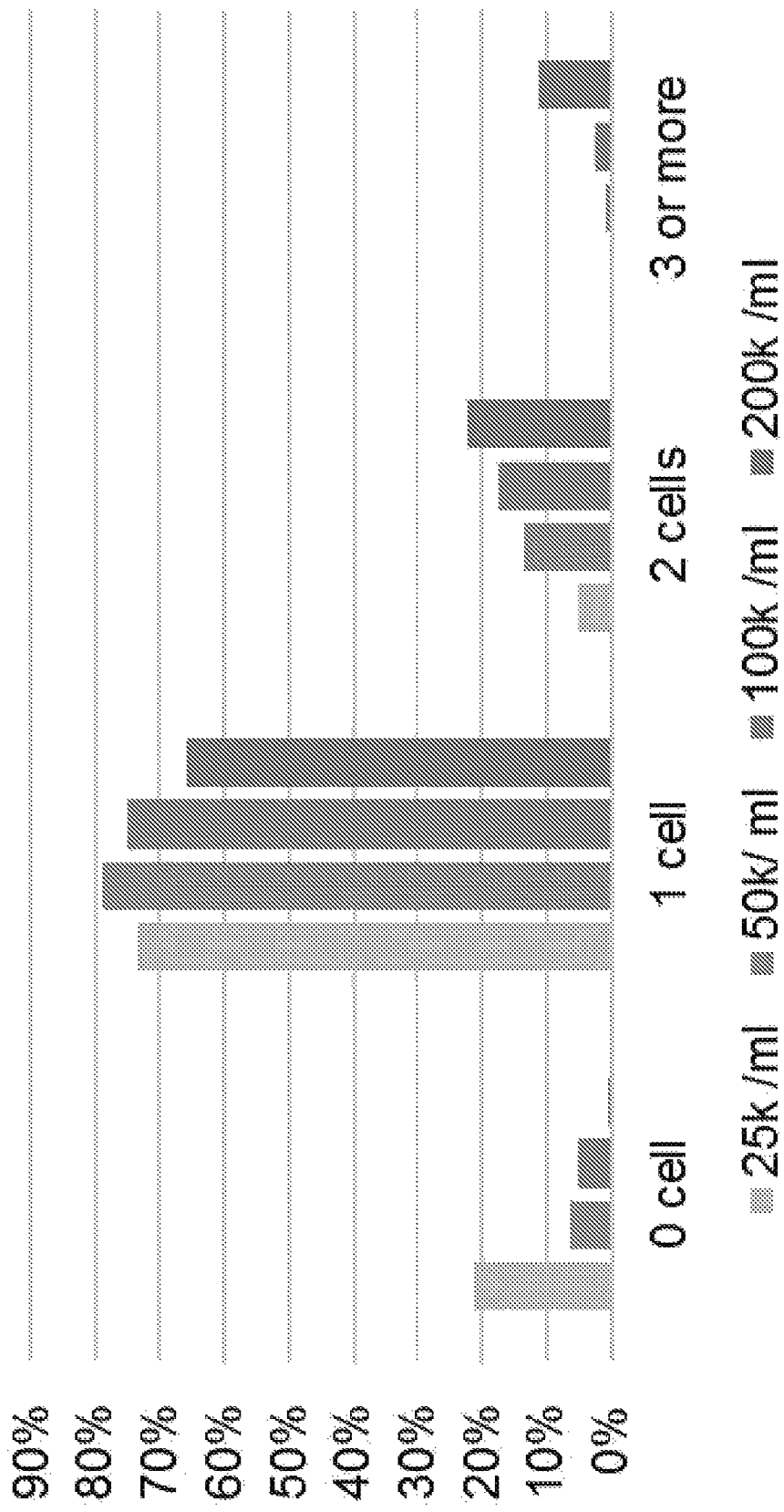

Single-cells are captured in micro-wells when they flow into the micro-wells and block the capture site. To increase the throughput, it was found that duplication of identical micro-wells into a larger array will suffer from low cell capture rate and clogging caused by non-uniformity of cell distribution between the upstream and downstream. To overcome this challenge, the scaling of the chip is achieved by engineering in two aspects. First, it was investigated how to increase more cell capture wells in each branch channel. Second, the throughput was scaled up by parallelizing the branch channels. A branch channel of 12,800-well chip is shown in FIG. 1 (c). In one design, each branch channel comprises an entrance channel and an exit channel with 200 micro-wells connected in parallel between them. After the entrance channel, a 40 μm high escape channel was added to release residual cells in the entrance channel after loading. To ensure uniform cell capture at the upstream and downstream of each branch channel, the unit flow resistance of entrance and exit channels was designed to be significantly lower than each capture well by 100 times using multi-layer fabrication (FIGS. 2 and 3). The flow resistance difference was achieved by implementing entrance channels and exit channels with a large channel height (100 μm) compared to the capture sites (10 μm). As the fluid was gradually transferred from entrance channels to exit channels when flowing to downstream, the entrance channels were tapered smaller and the exit channels were tapered larger to maintain the flow velocity in the channel. After finalizing the branch channel design, the channels were connected to the same inlet and outlet with branching channels. Using the scheme, chips with throughput from 800 wells/chip to 12,800 wells/chip are fabricated and tested. 800-well devices are composed of 16 branch channels with each containing 50 micro-wells, whereas 3,200-well devices are composed of 32 branch channels with each containing 100 micro-wells. (FIG. 4) The 12,800-well array is composed of 64 parallel branch channels with each containing 200 micro-wells as shown in FIGS. 1 (a) and (b). The highly-parallel structure also results in low flow resistance, enabling gravity flow (100 Pa) cell loading by simple pipetting. The complete layout of a 12,800-well chip is shown in FIG. 1 (d). FIG. 1 (e) shows the microscopic image of cells being captured in the array, highlighting the power of high-throughput single-cell capture capability.

Automatic Image Analysis Program

Figure 5:
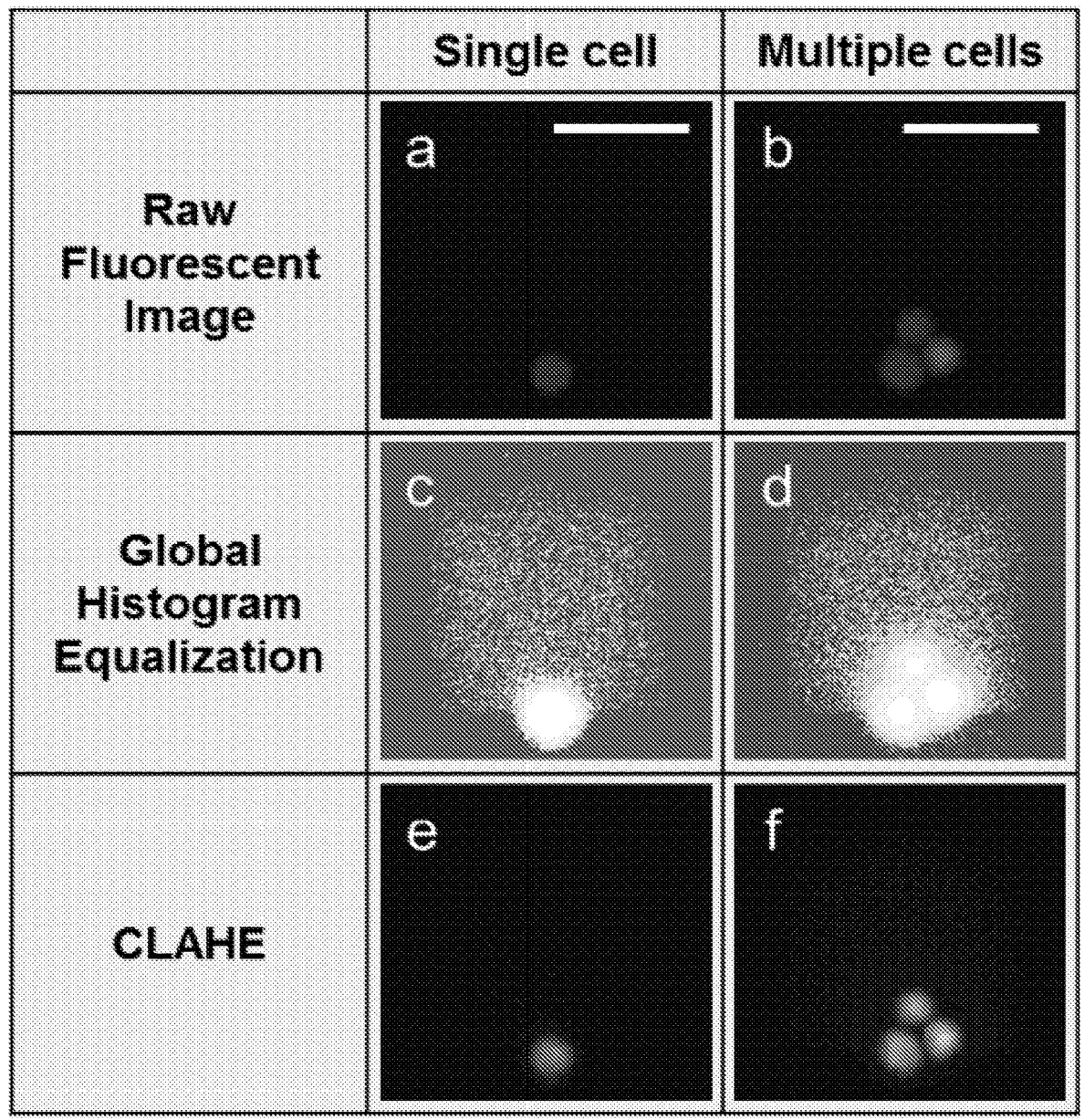
FIG. 5 shows contrast enhancement for image processing.
Figure 6:
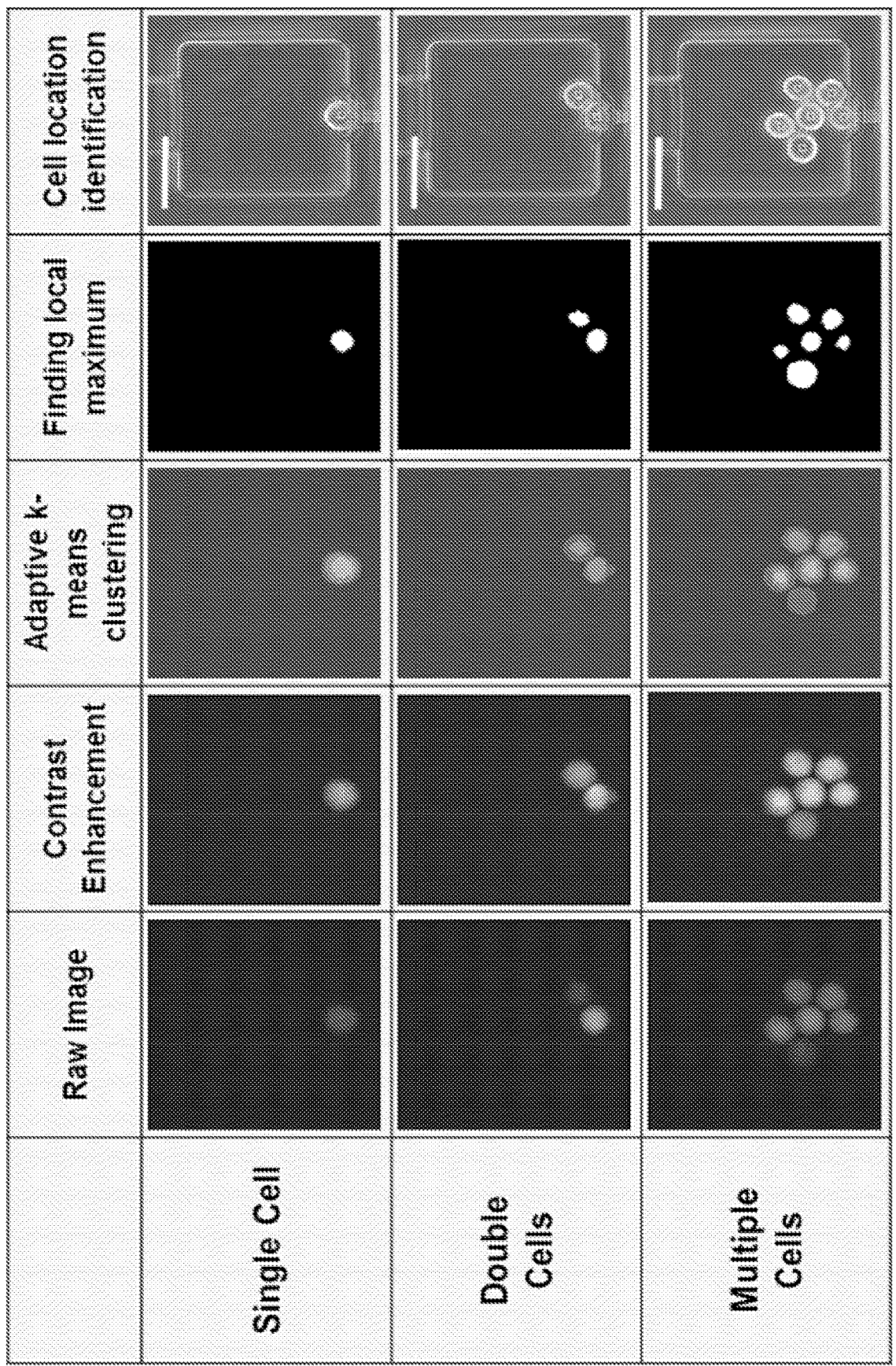
FIG. 6 shows cell counting with CLAHE contrast enhancement and adaptive k-means clustering to find the center of the cells in the image.
Figure 7:
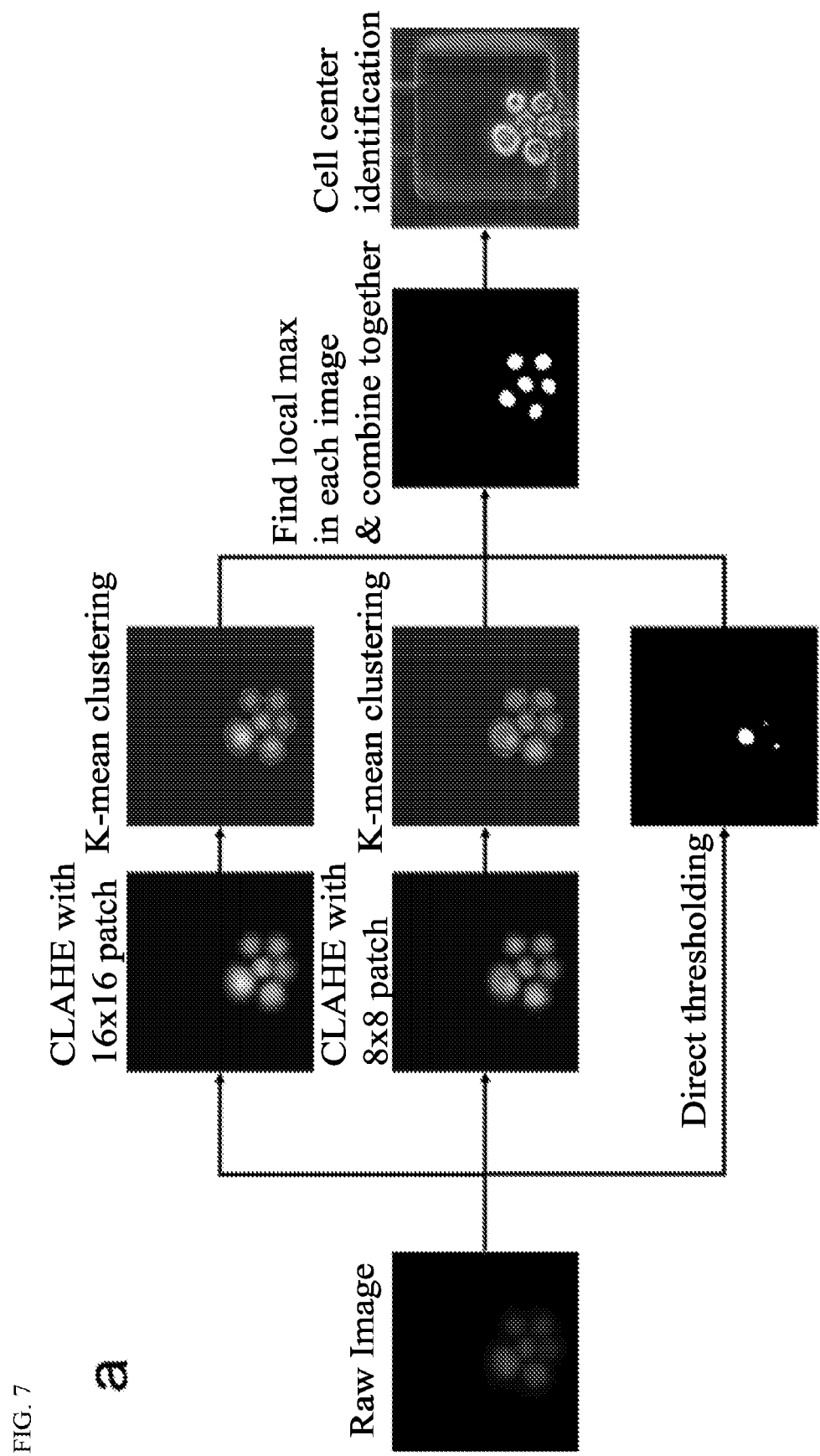
FIG. 7 shows µFAST cell counting working flow and accuracy testing result (a) Step-by-step diagram of cell counting. (b) Example of accuracy testing result, showing 98% high accuracy with few cases of over-count (+1 and +2) and under-count (−1 and −2). (N=6 with total 350 microwells tested)
Figure 7:
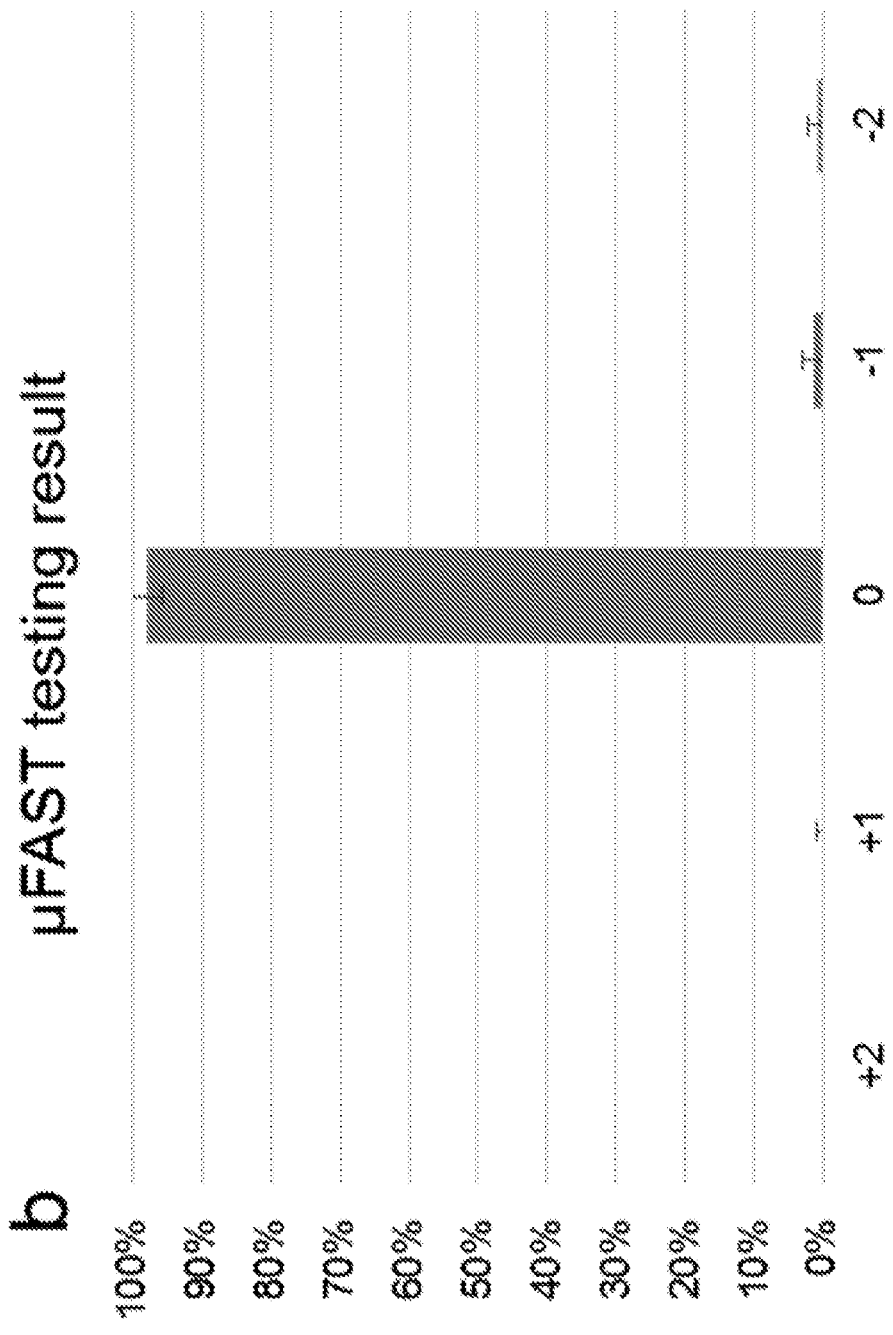
Figure 8:
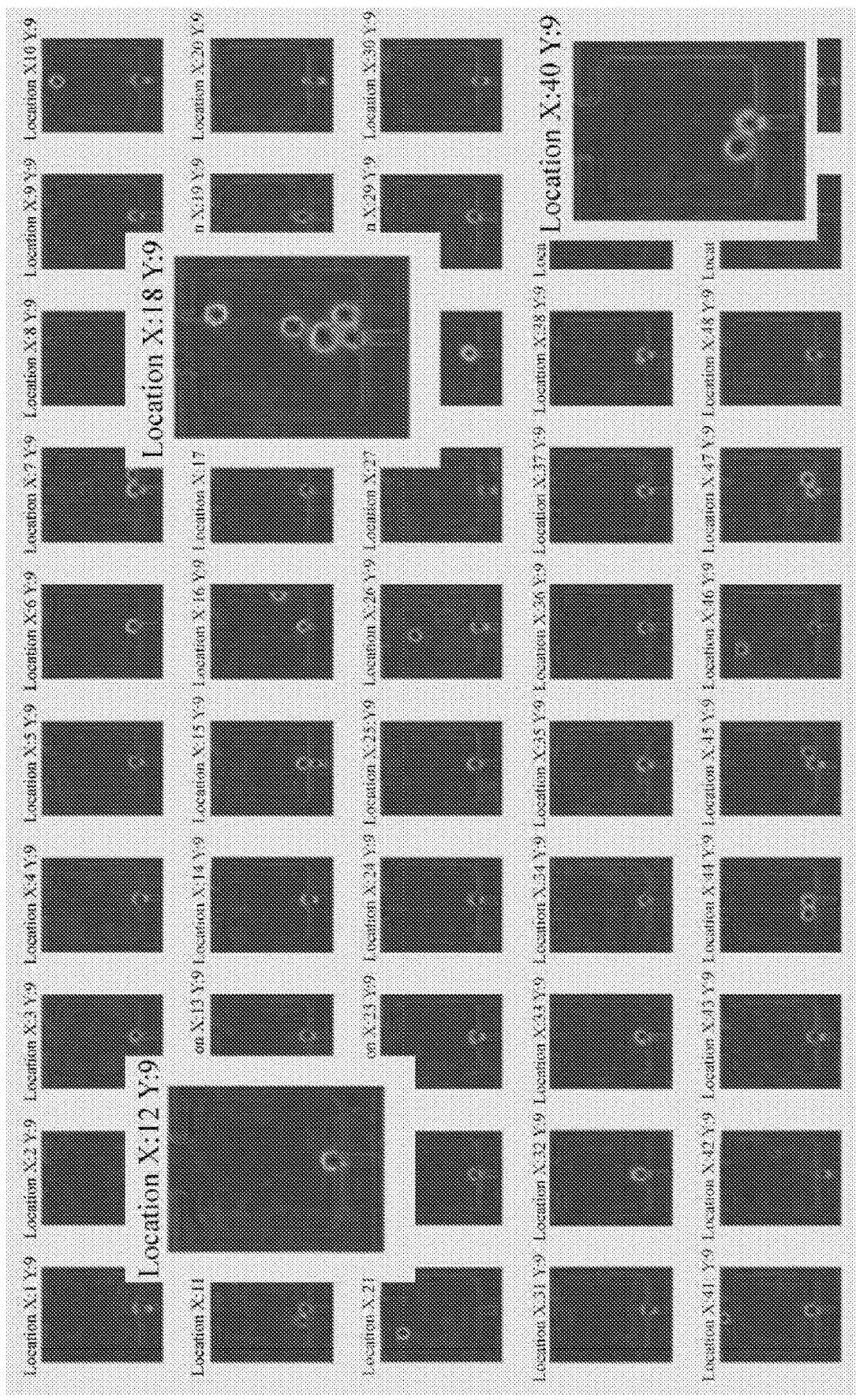
FIG. 8 shows an example of cell counting panel after cell capture to confirm counting accuracy.
Figure 9:
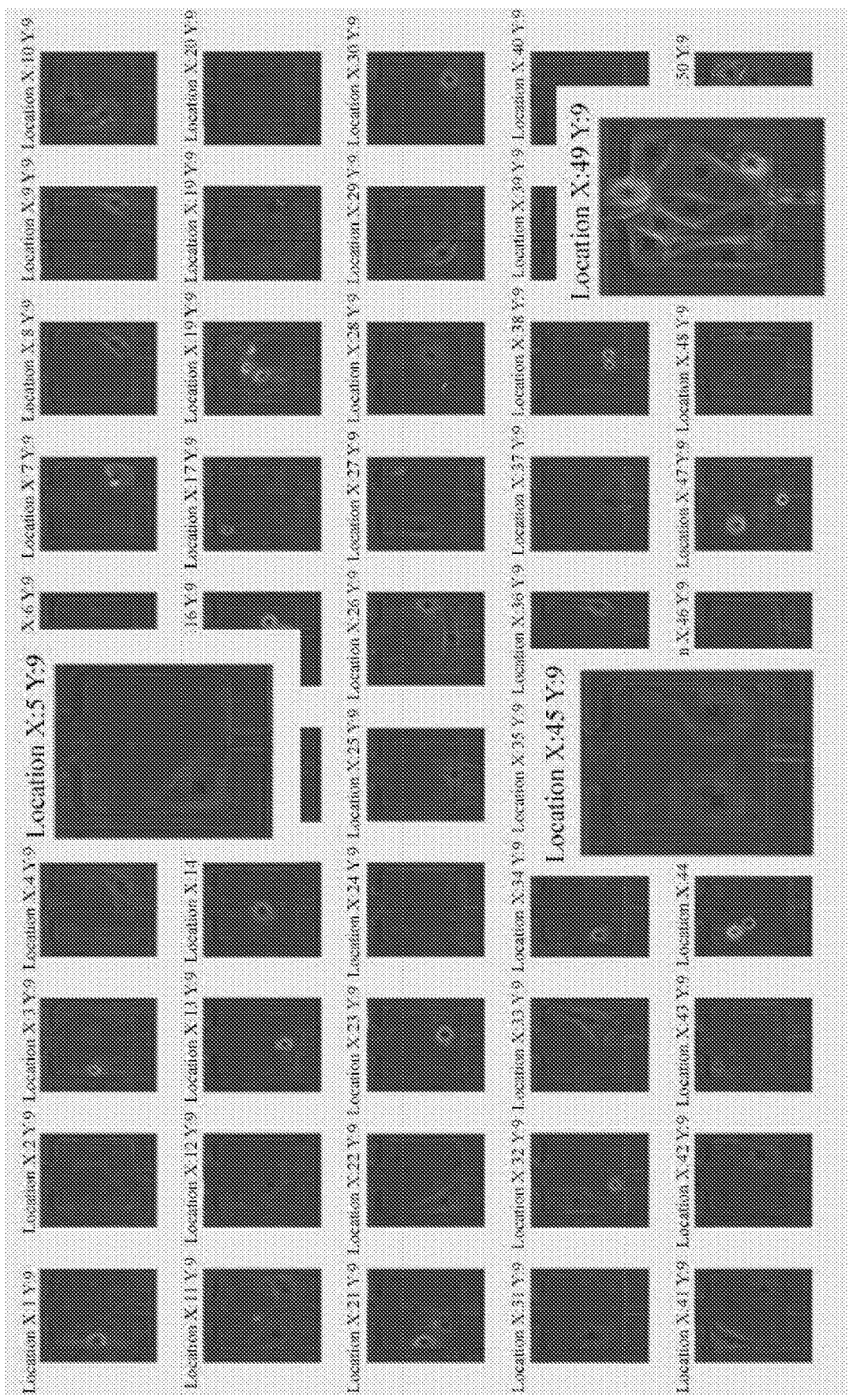
FIG. 9 shows an example of cell counting panel for adherent culture.
Figure 10A:
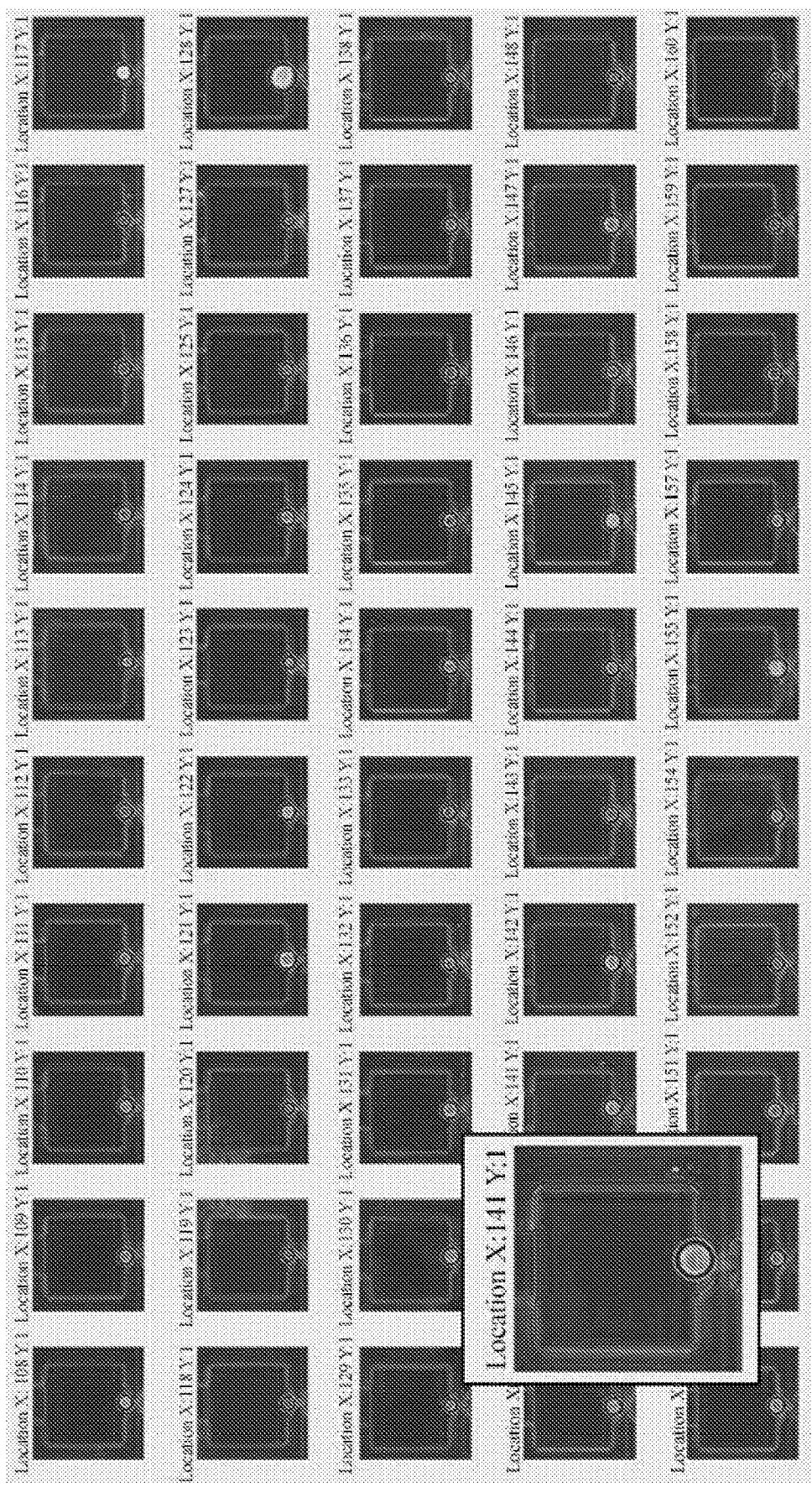
FIG. 10 shows cell size measurement with each cell size highlighted in a circle. (a) An example of cell size measurement panel for cells captured on chip. (b) To measure bulk cell size distribution, cells were flooded into a 100 µm-high chamber to ensure good imaging quality with cells on the same focal plane. (c) Cell size measurement of cells in bulk from the yellow box in (b).
Figure 10:
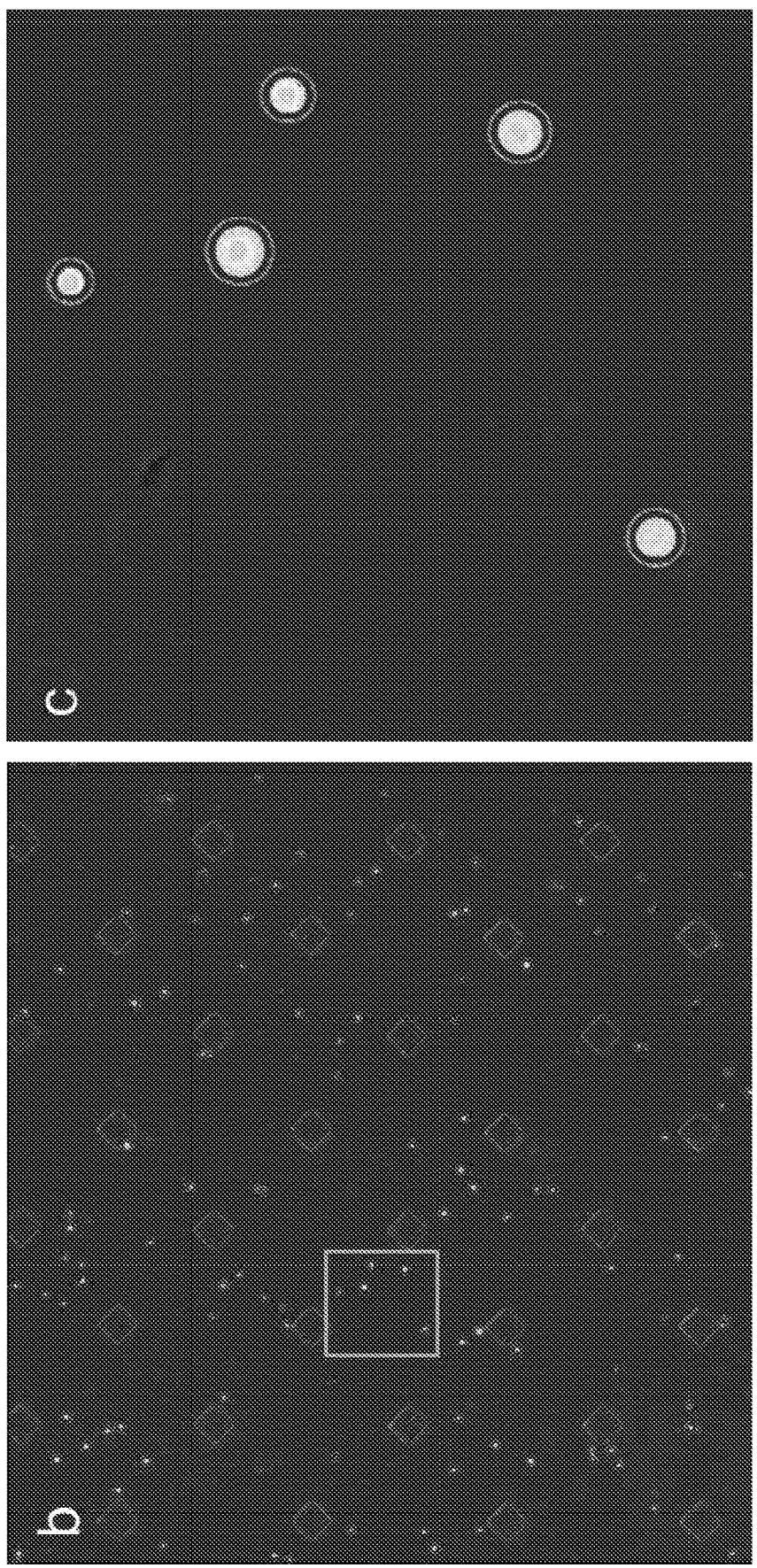
Figure 11:
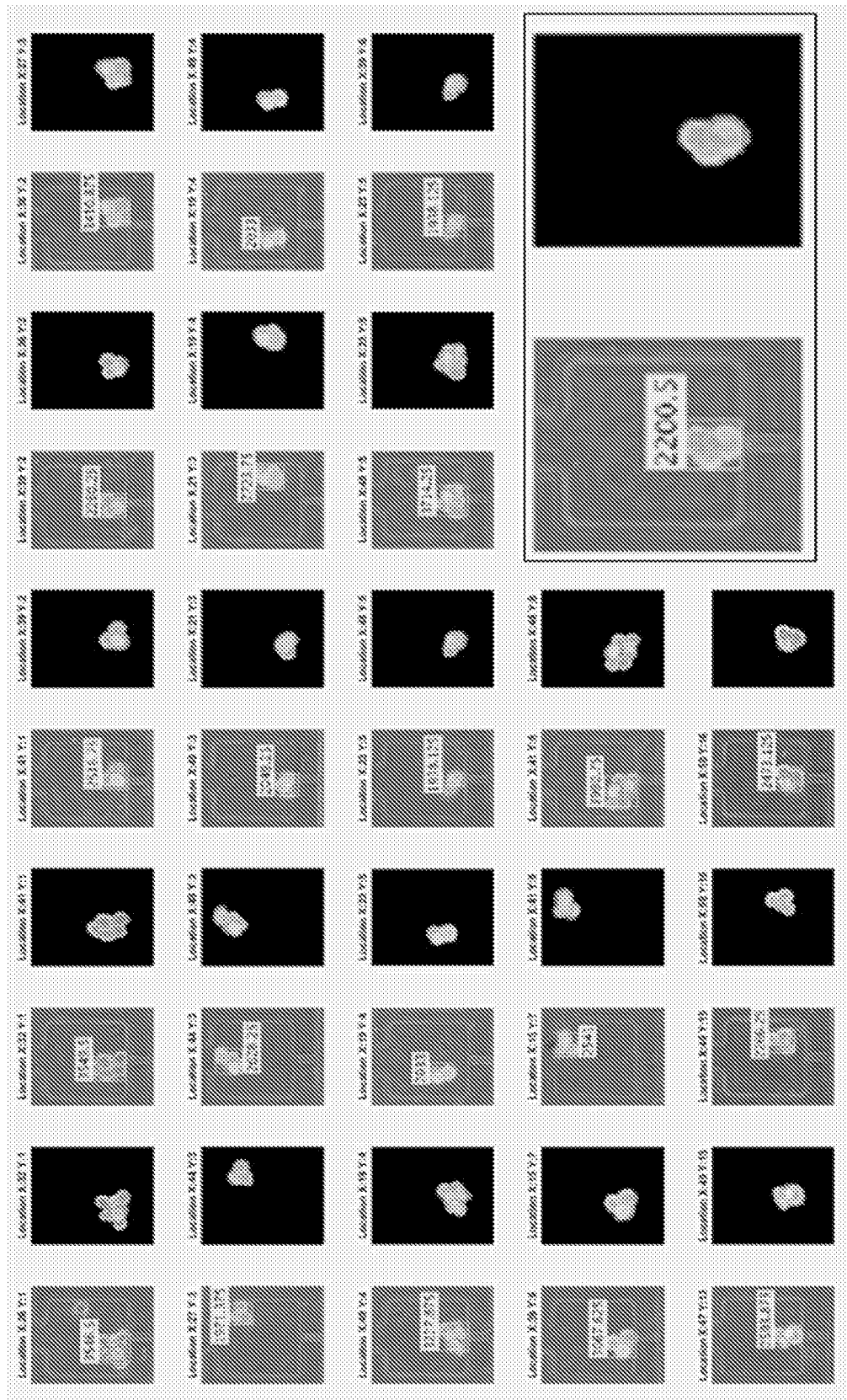
FIG. 11 shows sphere size measurement by fluorescent intensity thresholding.

A custom-made MATLAB program, called μFAST, was developed to achieve "image-in-result-out" capability with manual sample checking function to ensure analysis quality. First, a user specifies the four corners of a chip, so μFAST can identify the location of each cell micro-well with a unique address using vector space operation. After well segmentation, μFAST performs image analysis to calculate the parameters of interest such as the number of cells and the size of the cell/sphere in each well. Due to the heterogeneity of cell fluorescent intensity, contrast enhancement should be done before analysis to ensure dim cells are also counted (FIGS. 5 (a) and (b)). Since most parts of the background fluorescent image were dark, global histogram equalization generates artifact signals from noise in the background, making the image unusable for analysis (FIGS. 5 (c) and (d)). To overcome this problem, contrast-limited adaptive histogram equalization (CLAHE) was used to enhance contrast in a localized patch area, minimizing the noise from a homogenous dark background (FIGS. 5 (e) and (f)). For cell counting, a double k-mean clustering algorithm was then applied to find the local peak of the fluorescent intensity to identify the position of cells (FIGS. 6 and 7). A noise removal mechanism by morphological opening operations in local pixel area was also applied to remove false positives such as cell debris or local noise. This counting mechanism works reliably for both suspension and adherent cells (FIGS. 8 and 9). To measure the cell size, the Hough transform was used to identify circular cells and their diameters (FIG. 10). For sphere size calculation, intensity thresholding was applied to calculate the pixel area to extract the sphere area (FIG. 11). The pixel area was then converted to μm2 to calculate the sphere diameter. The presented μFAST program enables high-throughput analysis of thousands of cells with information such as cell size, number of cells, and also the sphere size for cell assay analysis.

Cell Capture and Captured Cell Size Characterization of the Scaling Structure

Figure 12A:
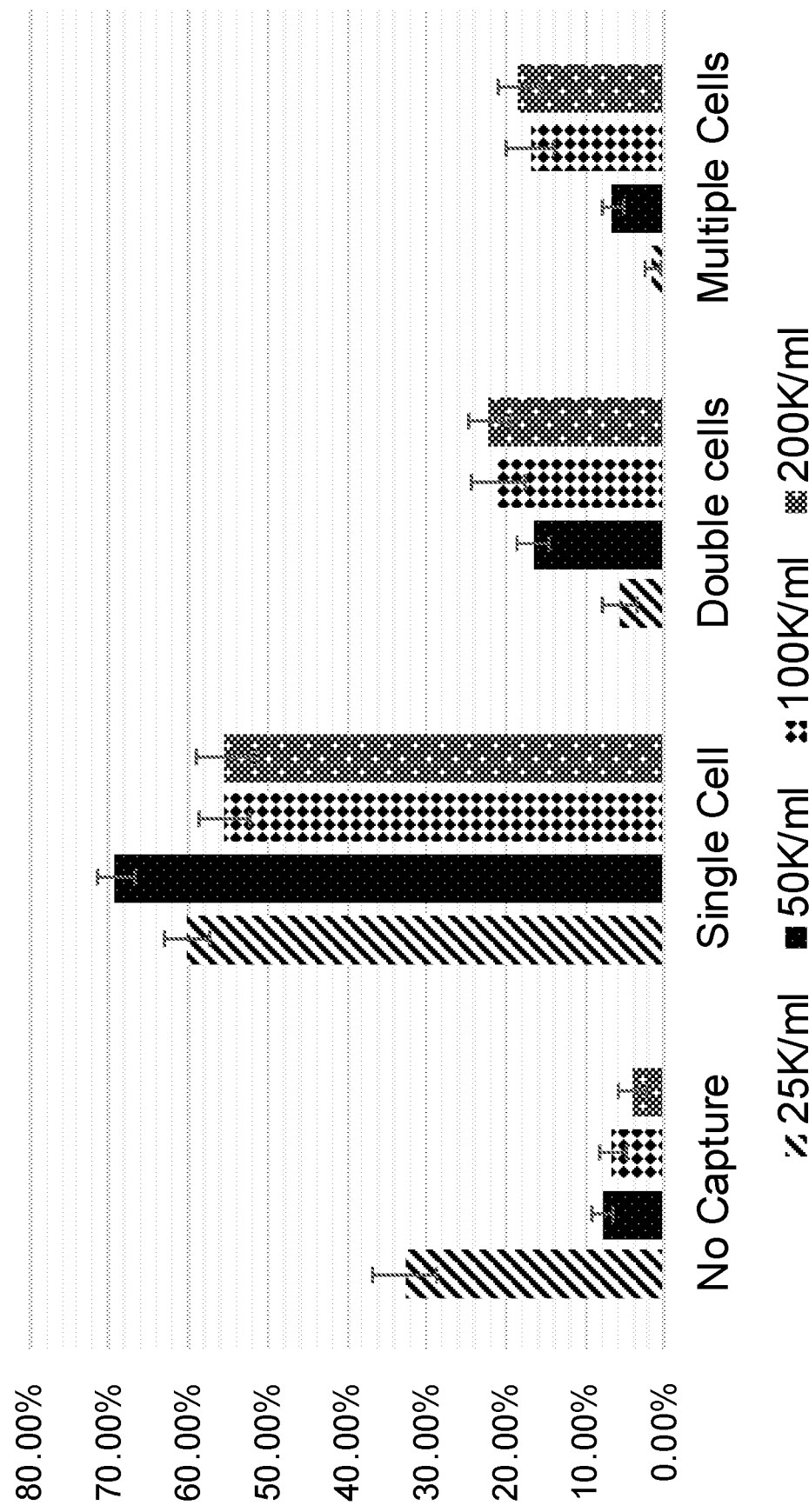
FIG. 12 shows (a) Cell capture result with different loading cell concentration (N=5) (b) Size distribution of MDA-MB-231 cells in bulk and captured in chip (N=600 for each case) (c)-(f) Examples of cells with different sizes captured in the chamber. The cell diameters are 12 µm in (c), 20 µm in (d), 30 µm in (e), and 40 µm in (f). (Scale bar: 50 µm)
Figure 12:
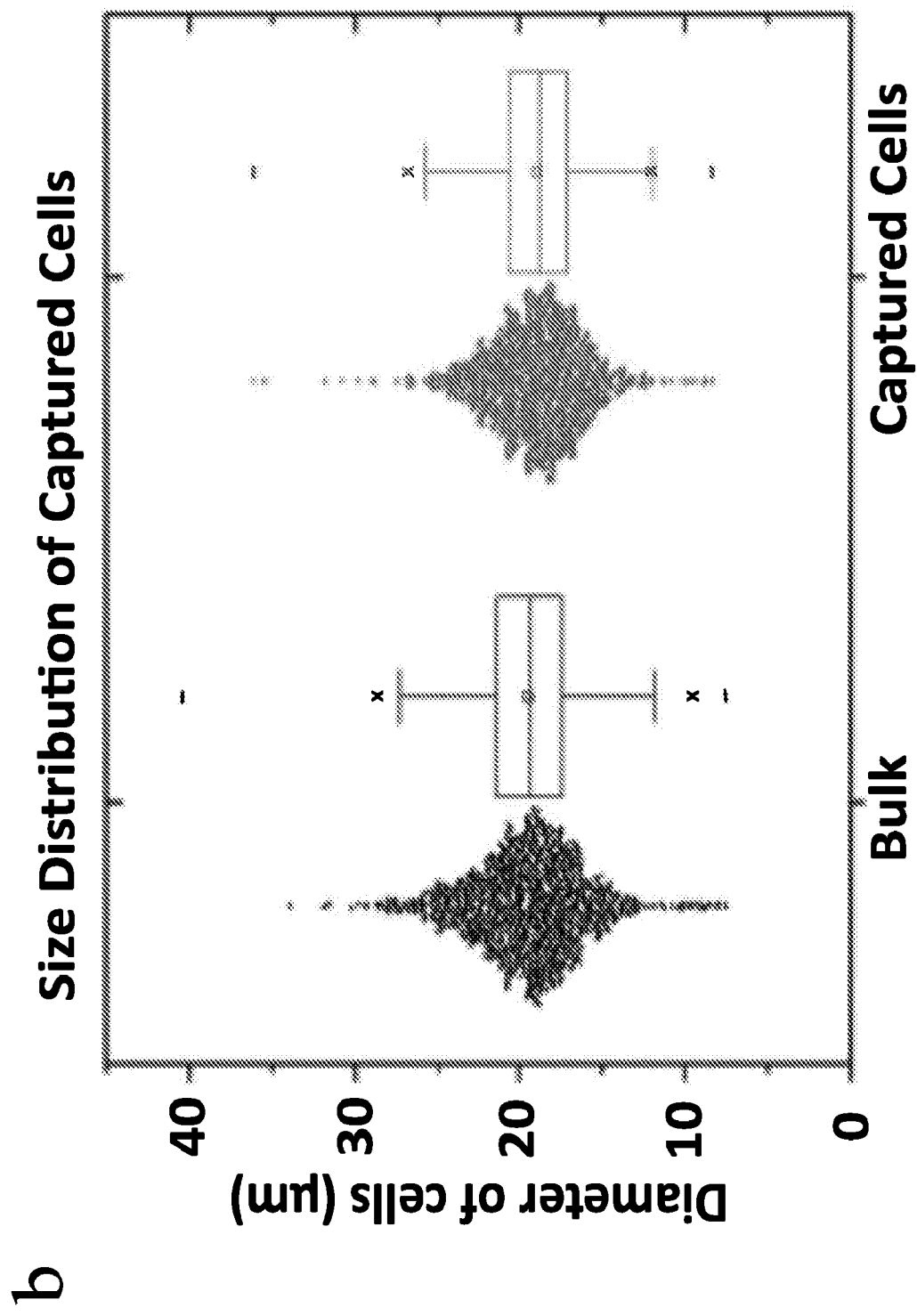
Figure 12:
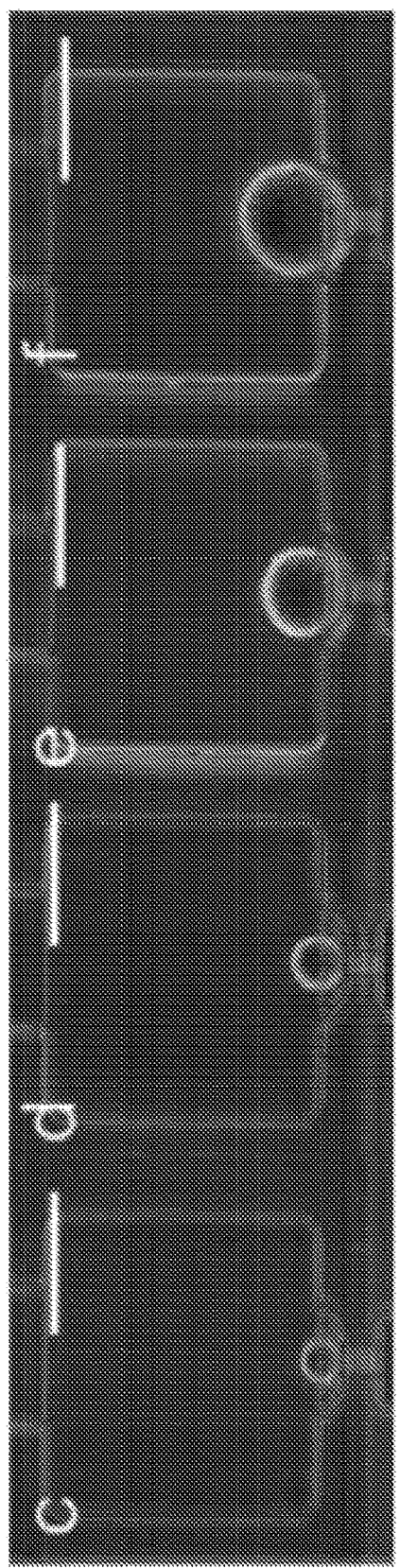

A high single-cell capture rate of ~76.5% was achieved at the optimal cell concentration of 50 k cells/mL. Reliable capture rate of >60% were attained in a wide range of concentrations from 25-100 k cells/mL (FIG. 12 (a)) Double and multiple captures had higher occurrence when higher concentration was used. It was observed that double and multiple captures have two different causes. They could be caused by the second cell coming into the micro-well before the first cell blocking the capture site. It could also be the consequence of the cells aggregating together in higher concentration in the cell suspension, resulting in cell cluster captures. Loading a lower concentration of cells helped reduce double and multiple capture significantly. However, the cell loading time is longer for lower cell concentrations, which can potentially affect cell viability. Given a 15 minutes loading time, 50 k cells/ml provides the optimal capture rate with consistent result. Due to the size heterogeneity of cancer cells, it is important that the capture scheme samples a representative population from bulk cells. The size distributions of cells captured on-chip and in bulk were measured and compared (FIG. 12 (b)). This shows the capability to capture cells with a wide range of sizes comparable to bulk cells as shown in FIG. 12 (c-f). The high capture rate performance with a representative cell size distribution provides robust single-cell isolation to study highly heterogeneous cancer cells.

Single Chamber Design for Bead Cell Pairing

Figure 13:
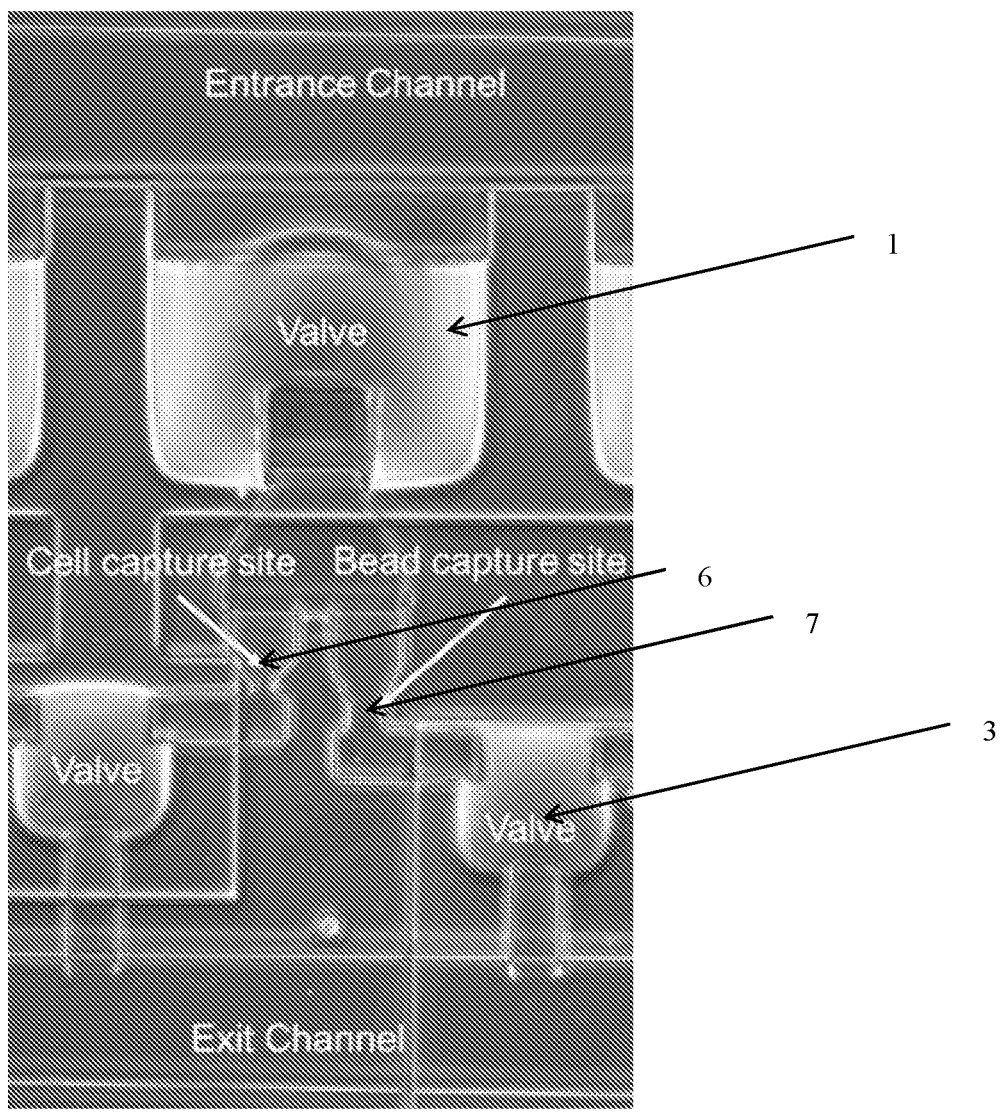
FIG. 13 shows hydro-Seq single chamber bead-cell-pairing design, showing the capture sites for cells and beads with the integration of pneumatic valves for flow path control.

In the hydro-Seq single chamber design, single beads and single cells are paired inside the same chamber (FIG. 13). The cells are captured at cell capture sites with 10 μm×10 μm opening area. During cell loading, the captured cells block the channel and stop the flow, preventing the next cell from entering the same chamber. As a result, each chamber only captures a single-cell. Similarly, in the bead capture chamber, a bead capture site was designed to prevent the next bead from entering the chamber when the capture site is occupied by a capture bead. Since beads are not deformable to seal the capture site area, it's important to optimize the capture site design and minimize multiple capture. The optimization is discussed in a following section. To sequentially load beads and cells into the chamber, the valve after the bead capture site was closed to block the flow path (FIG. 14). When the cell solution is loaded into the chip, the cells are captured at the cell capture site. After cell capture, the valve after the bead capture site is opened again to allow the flow to pass through. Thus, when introducing bead solutions, the beads are captured at the bead capture site following that flow path. After bead-cell pairing, different cell lysis methods are used to release the mRNA from the cells for analysis (FIG. 15). To use chemical lysis, the lysis buffer is flowed through the channels first and the valves are then opened for 1-2 second to allow some lysis buffer to enter the chamber. The valve is then closed quickly before the cells are lysed so the released mRNA wouldn't be lost through the flow wash. After cell lysis, the chip is incubated for mRNA hybridization onto the beads. Finally, the beads are retrieved by reserve flow and collected in the chip inlet. The beads are processed using a drop-seq protocol for sequencing analysis.

Single Chamber Design Bead Cell Pairing Procedure

Before testing, the device was heated at 150° C. for 30 minutes to deactivate any enzyme activities on the chip. The device was then placed in a desiccator with vacuum pressure for 20 minutes. After the vacuum process, the device was sanitized using UV radiation and primed using a 5% (w/w) PEO-terminated triblock polymer (Pluronic® F108, BASF) in DI-water for 20 mins. Before cell loading, channels were washed by flowing through 150 μL phosphate-buffered saline (PBS). The tubing was then connected to designated ports to enable pneumatic valve control. For Mixed-Species test, HEK cells and 3T3 cells were suspended using Trypsin-EDTA (Gibco 25200) and mixed together into 25 k cells/ml in PBS. For mixed cell line test, MDA-MB-231 and T47D were suspended using Trypsin-EDTA (Gibco 25200) and mixed together into 25 k cells/ml in PBS. The cell suspension solution was then loaded into the device inlet and cells were driven into the chip by gravity with flow rate around 2 μL/min. The valves after the bead capture sites were closed during cell loading. After cell loading, all valves were closed and the residual cells in the inlet and channels were washed away using PBS. Beads stored in TE buffer were then re-suspended in PBS twice and loaded into the chip with 20 k beads/ml by gravity flow. During the loading all the valves were opened to enable bead-cell pairing inside the chambers. Since the beads settle down easily in the inlet, it's important to pipette up and down from time to time during the loading process to ensure enough beads to enter the device. After bead-cell pairing, all the valves were closed and the lysis buffer was loaded into the outlet of the device. After lysis buffer flowing through the channels, the valves were opened for around 5 seconds to allow lysis buffer to enter the chambers while keeping the cells intact and inside the chambers. After cells were lysed, valves remained closed to incubate the sample and allow released mRNA to hybridize with the barcoded beads. Right before bead retrieval, the valves were opened and beads were retrieved by drawing 500 μL of PBS from the outlet to the inlet using negative pressure. The retrieved beads were then processed for sequencing according to drop-seq protocol with minor modifications.

Dual Chamber Design for Bead Cell Pairing

Figure 17:
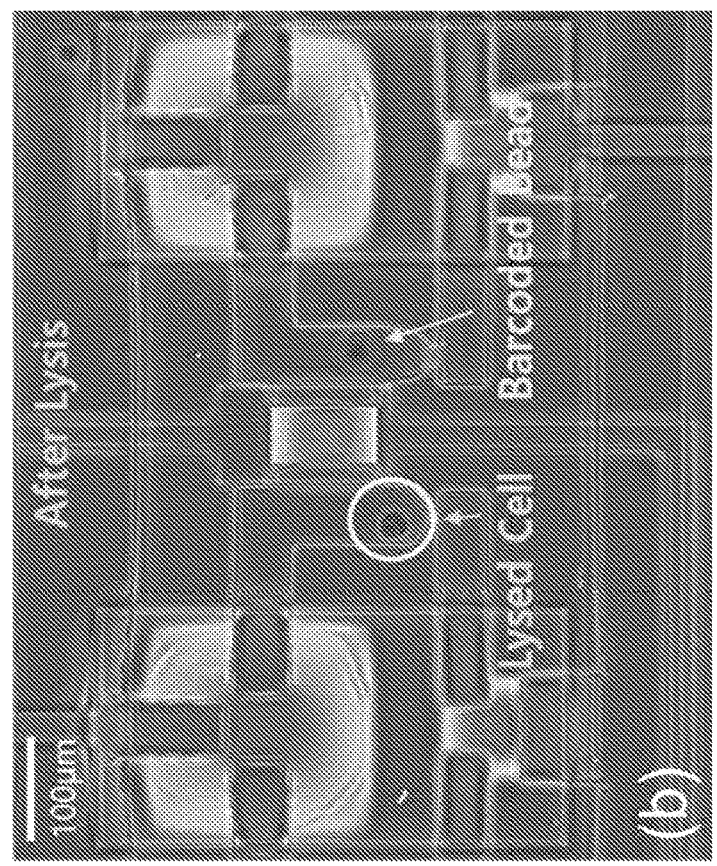
FIG. 17 shows cell lysis process in hydro-Seq dual chamber design. (a) Before opening the isolation valve, a healthy cell can be observed inside the cell capture chamber paired with another bead inside the neighboring bead capture chamber. (b) After opening the isolation valve, the lysis buffer in the bead chamber diffused into the cell chamber and lysed the cell.
Figure 17:
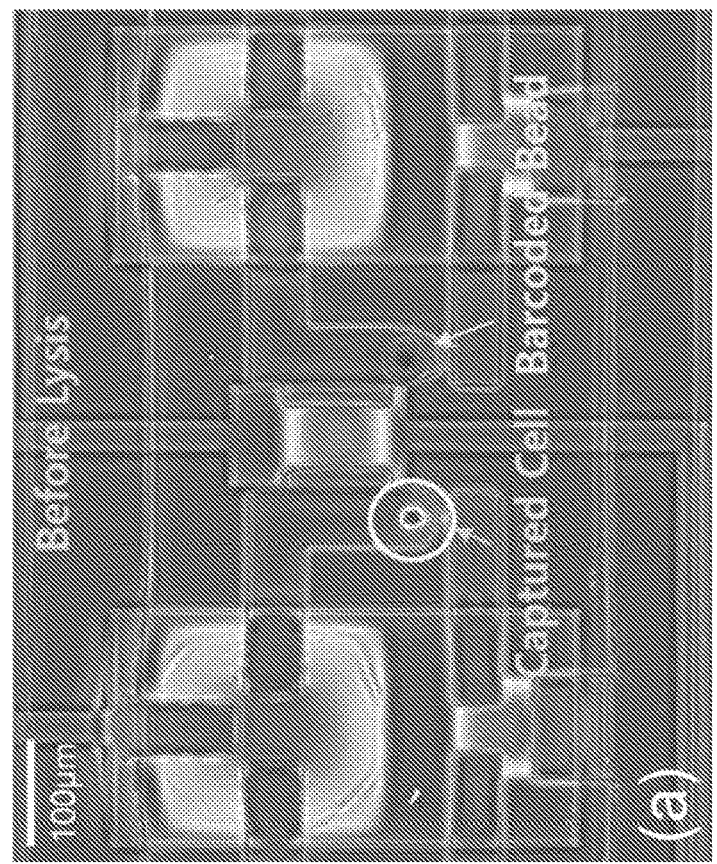

In the hydro-Seq dual chamber design, there are paired chambers to capture single cells and single beads separately (FIG. 16). In the cell capture chamber, there is a narrow channel with 10 μm×10 μm size as cell capture site. During cell loading, the captured cells block the channel and stop the flow, preventing the next cell from entering the same chamber. Similarly, in the bead capture chamber, a bead capture site was designed to prevent the next bead from entering the chamber when the capture site is occupied by a capture bead. To enable the assay procedure, the pneumatic valves were integrated on chip. There are valves to control the close and open the cell capture and bead capture chambers. There is another isolation valve in between the cell and bead chambers. During the cell and bead capture process, the isolation valve is closed to prevent the cross-talk between the cell and bead capture chambers. After cells and beads are captured, the bead capture chamber is filled with lysis buffer. By closing the valve around the capture chambers and opening the isolation valve, the lysis buffer diffuses into the neighboring chambers and lyses the cells (FIG. 17). After some incubation time to allow mRNA to hybridize onto the beads, the beads are collected form the chip inlet by reversing the flow. The beads are processed following drop-seq protocol for sequencing analysis.

Dual Chamber Bead Cell Pairing Procedure

Before testing, the device was heated at 150° C. to deactivate enzyme activities on chip for 30 minutes. The device was then placed in a desiccator with vacuum pressure for 20 minutes. After the vacuum process, the device was sanitized using UV radiation and primed using a 5% (w/w) PEO-terminated triblock polymer (Pluronic® F108, BASF) in DI-water for 20 mins. Before cell loading, channels were washed by flowing through 150 μL phosphate-buffered saline (PBS). The tubing was then connected to designated ports to enable pneumatic valve control. For Mixed-Species test, MDA-MB-231 cells and T47D cells were suspended using Trypsin-EDTA (Gibco 25200) and mixed together into 25 k cells/ml in PBS. For mixed cell line test, MDA-MB-231 and T47D were suspended using Trypsin-EDTA (Gibco 25200) and mixed together into 25 k cells/ml in PBS. The cell suspension solution was then loaded into the device inlet and cells were driven into the chip by gravity with flow rate around 2 μL/min. The isolation valves and bead valves were closed during cell loading. After cell loading, all valves were closed and the residual cells in the inlet and channels were washed away using PBS. Beads stored in TE buffer were then re-suspended in lysis buffer and loaded into the chip with 20 k beads/ml by gravity flow. During the loading, cell valves and isolation valves were closed to ensure good bead capture and prevent cells from exposing to lysis buffer. Since the beads settle down easily in the inlet, it is useful to pipette up and down from time to time during the loading process to ensure enough beads to enter the device. After bead-cell pairing, bead and cell the valves were closed. Then the isolation valves were opened and closed several times to facilitate the mixing of lysis buffer and PBS to fully release mRNA from single-cells (FIG. 2, 4). After cells were lysed, samples were incubated for 10 minutes to allow released mRNA to hybridize with the barcoded beads. Right before bead retrieval, the valves were opened and beads were retrieved by drawing 500 μL of PBS from the outlet to the inlet using negative pressure. The retrieved beads were then processed for sequencing according to drop-seq protocol with minor modifications.

Scaling of Bead-Cell Pairing Chambers with Washing Channels

With the chamber design, the throughput of hydro-Seq is easily scaled using the presented scaling method. To achieve quality sequencing results, it is important to wash away residual cells, reagents, or debris in the entrance and exit channel. Thus, valve controlled washing channels were added to connect the entrance and exit channel at the two ends (FIG. 18). During cell and bead loading, the channels are closed using pneumatic valves. When washing is needed, the valves are opened so fresh reagent can flush the channel to remove potential contaminants in the channels. Depending on the application, it is possible to build multiple inlets to the same chip (FIG. 18). For example, in an application where multiple CTC clusters are analyzed, each sample is processed in different areas of the chip and collected into different tubes. With different barcodes for each tube, the sample of origin can be tracked after sequencing analysis.

Bead Capture Site Optimization

Figure 21:
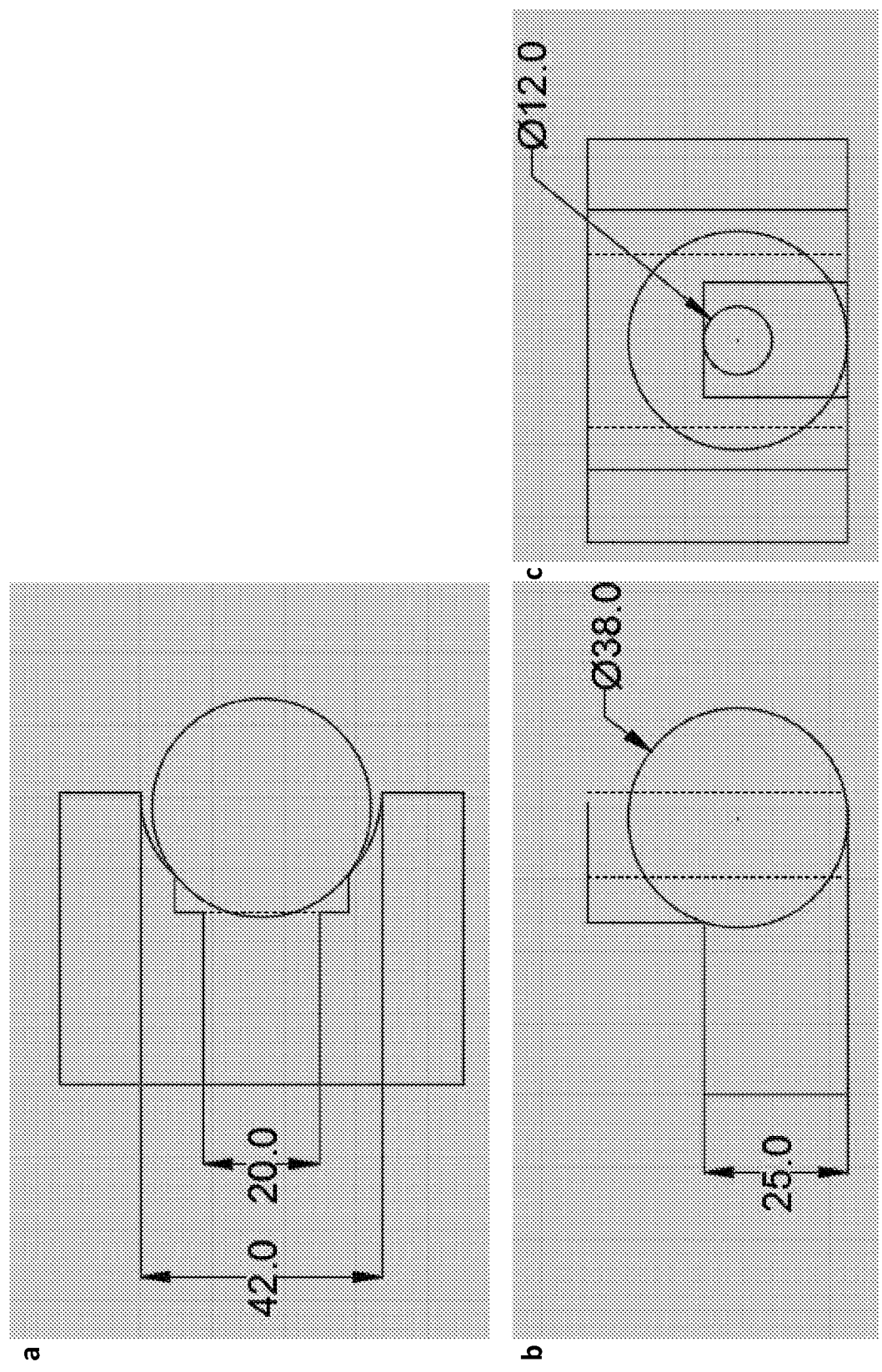
FIG. 21 shows a cross section of bead capture with 38 µm diameter bead. (a) Top view of bead capture site. (b) Side view of bead capture site. (c) Front view of bead capture site. The inner circle denotes the portion of the capture channel blocked by the bead.

The bead capture site of the chamber is optimized to capture beads with a wide range in diameter. In the current embodiment, single beads ranging from 25 to 42 μm in diameter can be captured in the chamber and prevent further beads from entering. The capture site comprises two components, a curved "pocket" that holds the bead in place, and a narrow capture channel that the bead cannot pass through (FIG. 20). The curved pocket has a semicircular profile designed to accommodate beads up to 42 µm in diameter. In addition to holding the bead in place, the curved pocket also improves the ability of a bead to block the flow of fluid through the capture channel. FIG. 21 shows a cross section of the top, side, and front view of the curved pocket and capture channel when a 38 µm diameter bead is captured. The front view of the capture site in FIG. 21c shows that a significant portion of the cross-sectional area is blocked by the bead at both the curved pocket and at the capture channel. This blockage increases the flow resistance of the chamber and prevents beads from entering the chamber if other downstream chambers are empty. To effectively capture beads with a certain range in diameter, the dimensions of the curved pocket and capture channel are adjusted. The three parameters used to optimize the capture site design are the minimum, maximum, and average bead diameter. When setting the capture channel dimensions, either the width or height of then channel should be less than the diameter of the smallest beads. For example, if the minimum bead size is 25 µm, the height of the capture channel should be 25 µm. With this constraint, the width is optimized to allow the greatest change in cross sectional area blocked by the bead. The average bead diameter is used to find the optimal channel width. The difference between the height of the channel and the radius of the bead defines the radius of the cross-sectional area blocked by the bead. The channel width should be set to twice this radius to maximize the change in cross sectional area blocked by the bead. For example, with a 25 µm channel height, a 15 µm radius bead blocks a 10 µm radius cross-section. Therefore, the channel width is set to 20 µm. FIG. 21c shows the 12 µm diameter cross-sectional area blocked by a 38 µm diameter bead. For larger beads, the curved pocket plays a role in increasing the area blocked by the bead. The optimal pocket size is the maximum bead diameter. Larger or smaller pocket sizes decrease the change in blocked area or prevent the bead from reaching the capture channel. By optimizing the dimensions of the capture site, bead capture rates of over 80% have been achieved.

Flow Balance During Valve Operation

Figure 22:
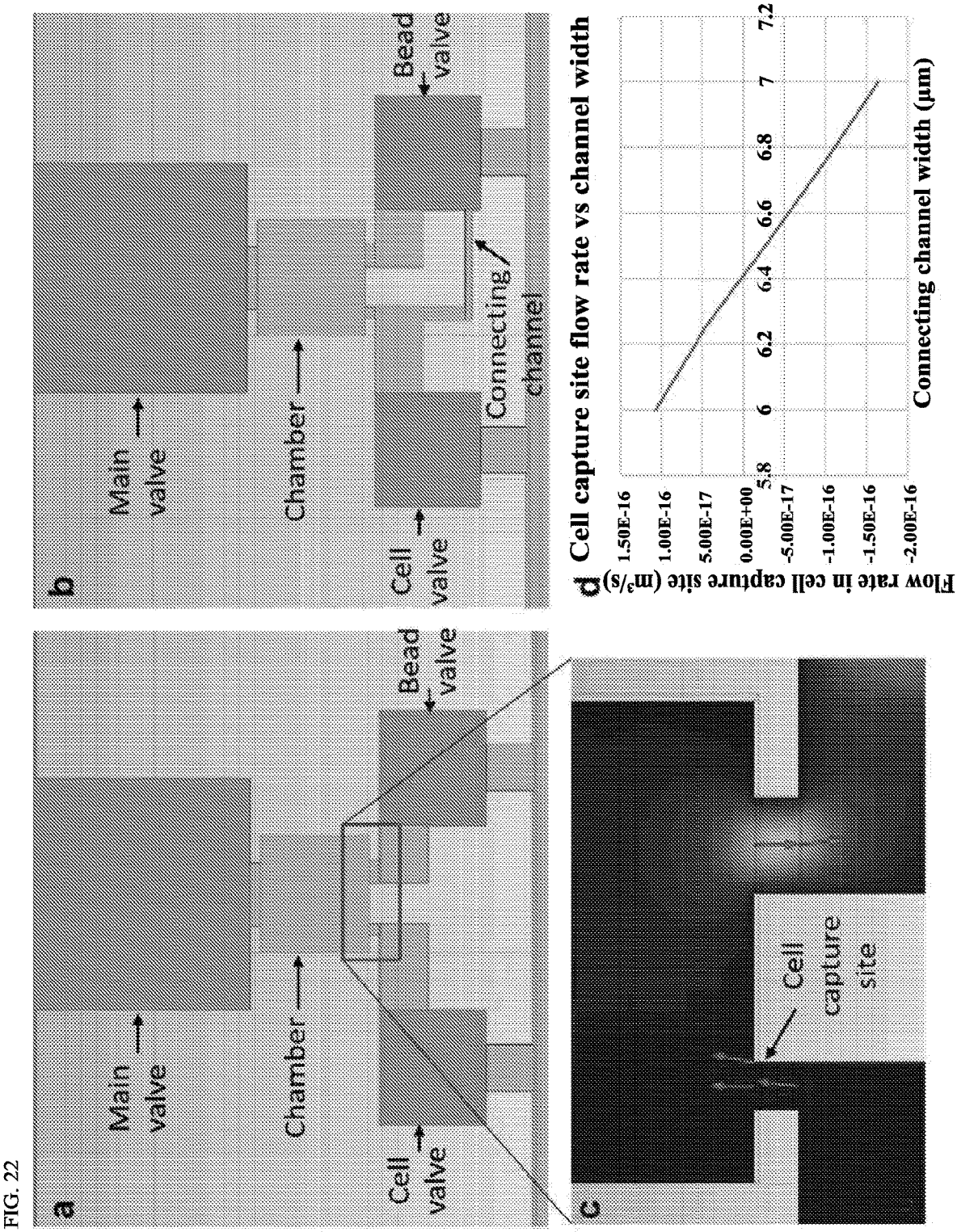
FIG. 22 shows flow balance at cell capture site during valve operation. (a) Device geometry without connecting channel. (b) Device geometry with connecting channel between cell capture site and bead valve. (c) Flow velocity near cell capture site after valve opening simulated using COMSOL. Without the connecting channel, the flow rate out of the cell capture site is positive. (d) Cell capture site flow rate vs connecting channel width.

During the cell loading process, the valves controlling the flow through the bead capture site are closed. When opening these valves to begin bead loading, the valve membrane deflects upward and creates a negative pressure in the valve region. This sudden pressure drop can disrupt the position of the captured cell, causing it to flow toward the valve region (FIG. 22a, c). It is possible to compensate the reverse flow in the cell capture site by adding a channel connecting the cell capture site to the bead control valve as shown in FIG. 22b. With the addition of this connecting channel, opening the bead control valve results in no net flow at the cell capture site. The net flow rate into or out of the cell capture site was simulated using COMSOL, and FIG. 22d shows the resulting flow rates for different connecting channel widths. For the device geometry shown, the connecting channel width of 6.4 µm results in a net flow of zero. This means that opening the bead valve does not disturb the position of the cell. Increasing the width of the connecting channel can increase the flow rate into the capture site, which holds the cell in place with greater pressure. This technique is useful to control the flow balance at the cell capture site and is valuable when large valves are used.

Device Fabrication

The devices were made using soft-lithography fabrication process. The multi-layer layout of the chip was designed using AutoCAD 2016 (Autodesk®). The masks for photolithography were made using a mask making instrument (µPG 101, Heidelberg instruments). The mold for the flow channel was fabricated with 10 µm, 25 µm, 45 µm, and 100 µm thick SU-8 (Microchem) following the manufacturer's protocol. The valves were created using AZ®9260 (AZ Electronic Materials) with peak thickness of 45 µm and 20 µm after reflow. The mold for the control channels was fabricated with 20 µm SU-8. The SU-8 mold was treated by vaporized trichloro(3,3,3-trifluoropropyl)silane (452807 ALDRICH) under vacuum overnight to promote the release of cured PDMS. PDMS (Sylgard 184, Dow Corning) was prepared by mixing with 10 (elastomer): 1 (curing agent) (w/w) ratio, poured on flow channel molds, and cured at 85° C. overnight before peeling. Thin film of PDMS was spun onto the control channel mold and cured at 85° C. for one hour. After peeling the PDMS from the flow control mold, the PDMS piece and the thin film PDMS were treated using oxygen plasma (80 W for 60 seconds) and bonded using MJB3 aligner (Karl Suss). The devices after bonding were heated at 80° C. overnight to ensure bonding quality.

Single Cell Transcriptome Analysis Sequencing Result

Figure 23:
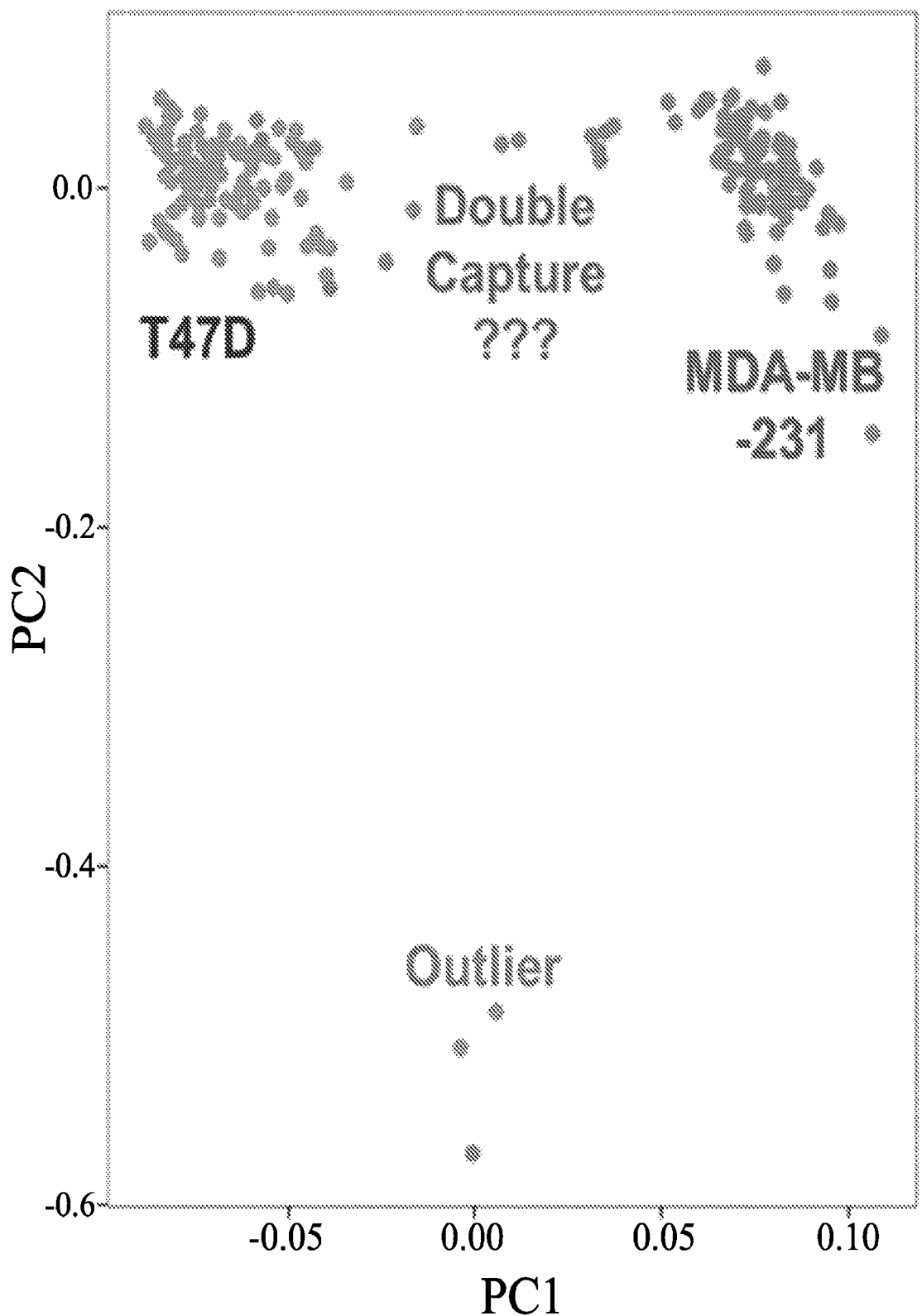
FIG. 23 shows single cell gene expression data with clustering plots. (left) PCA plot: cells are separated into T47D and MDA-MB-231 cells using EpCAM and Vimentin expression. (right) tSNE plot: two groups of cells (left and right) can be clustered, showing clear separation and difference between MDA-MB-231 cells and T47D cells.
Figure 23:
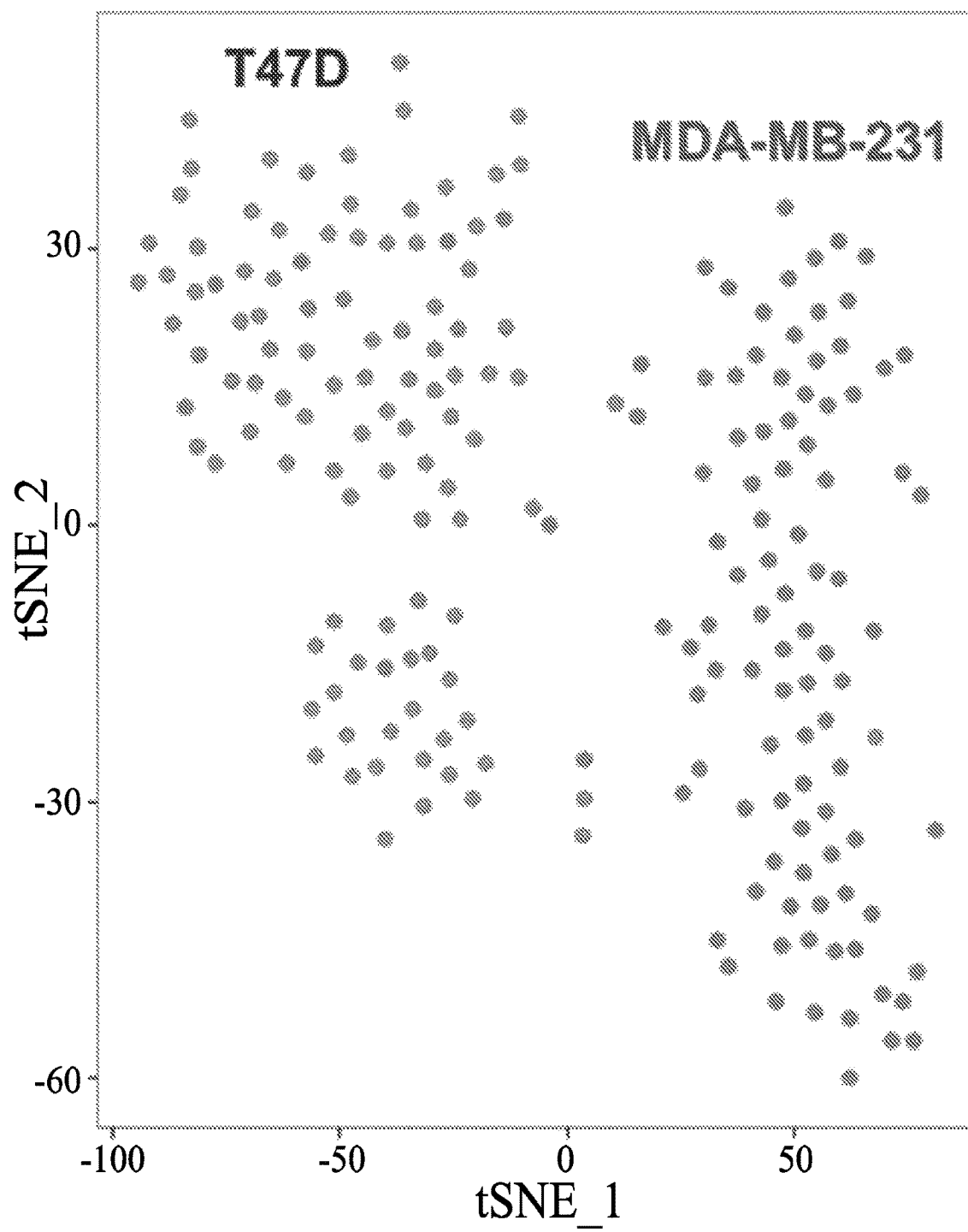
Figure 24:
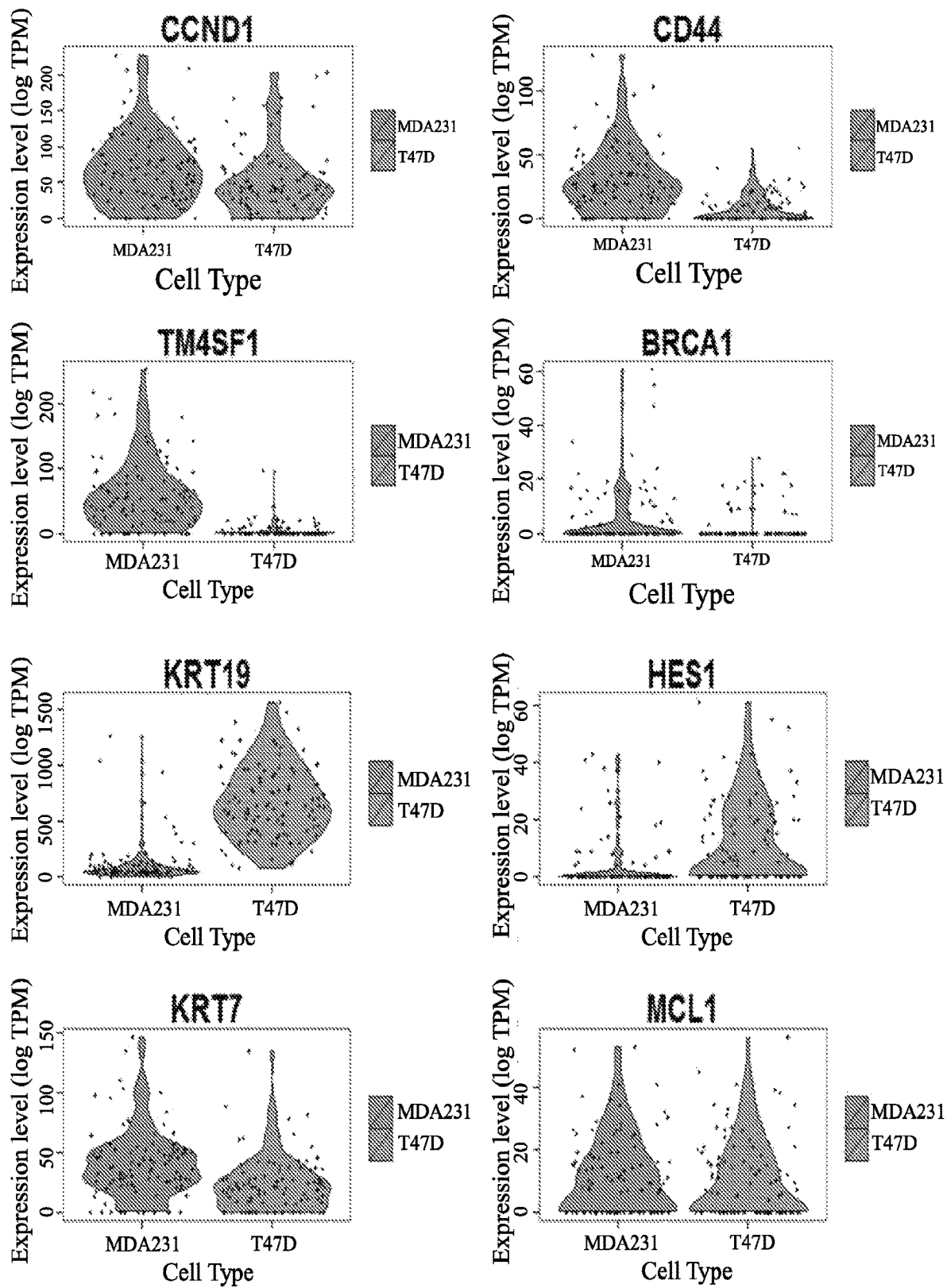
FIG. 24 shows a violin plot of selected genes from the single cell whole transcriptome analysis.
Figure 24:
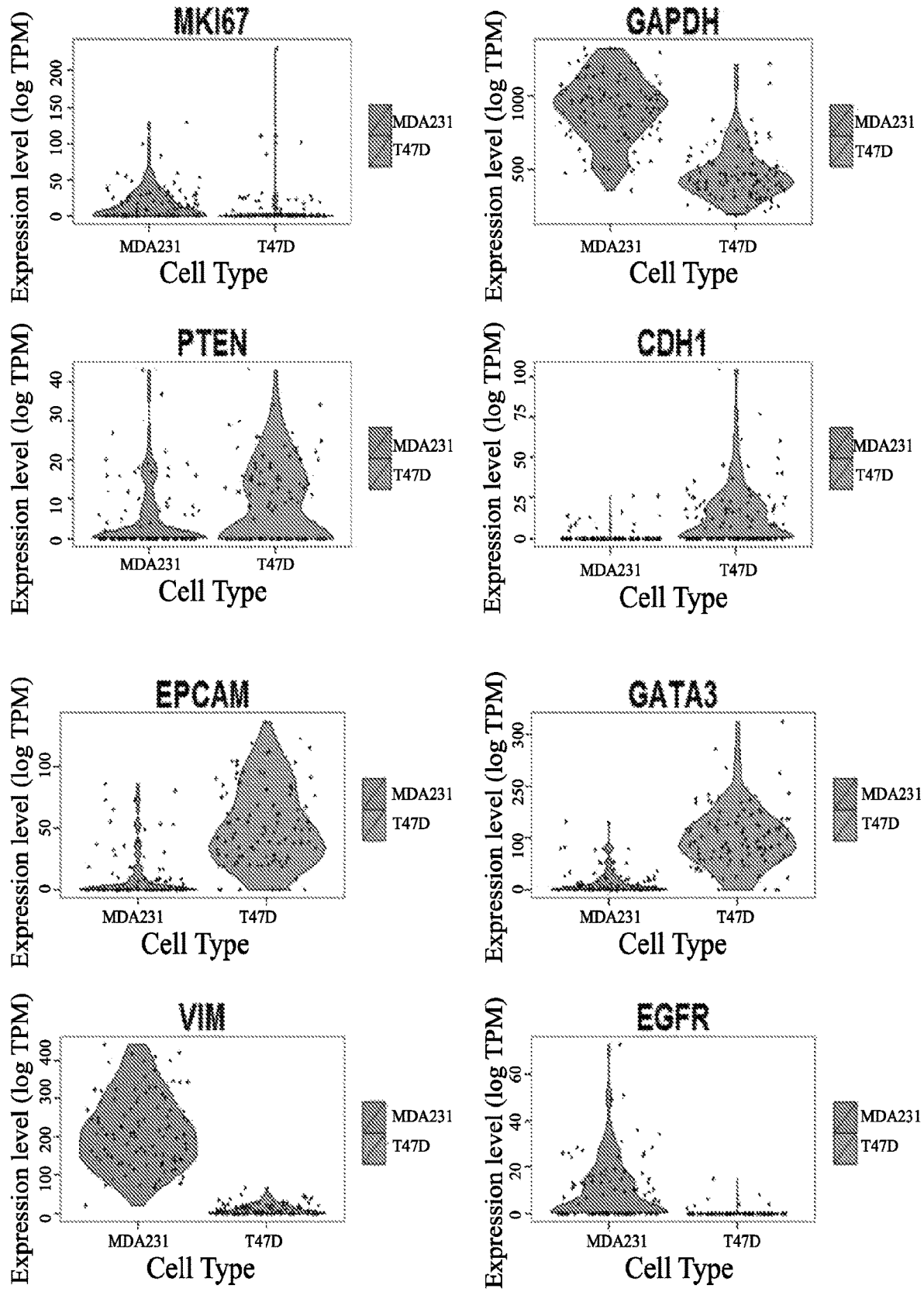

After the sequencing the prepared sample from the experiment, the gene expression profile was plotted in the PCA and two clusters were identified (FIG. 23). To identify the T47D and MDA-MB-231 populations, two well-known markers, VIM and EpCAM, were used because MDA-MB-231 should express VIM but not EpCAM, while T47D should express EpCAM but not VIM. The expression data of those two genes are pretty exclusive. The majority (~70%) of cells only expressed one of the genes. For the rest of the cells, cell types were distinguished by their relative expression level. Going back to the PCA plot, it was found that T47D and MDA-MB-231 cells have two distinct cluster with a small number of cells mixed in the group. There were also some outliners far away from the majority of cell populations in the plot (FIG. 23). Similar clustering was also found when using another clustering method called t-distributed stochastic neighbor embedding (tSNE) (FIG. 23). After distinguishing T47D and MDA-MB-231 cells, gene expressions was analyzed using a violin plot. The result matches well with previous published results (FIG. 24). When choosing the highest and lowest expressed genes from the sample, it was found that T47D and MDA-MB-231 showed very distinct gene expressions.

Addressable Multiplexed Valves

Figure 25:
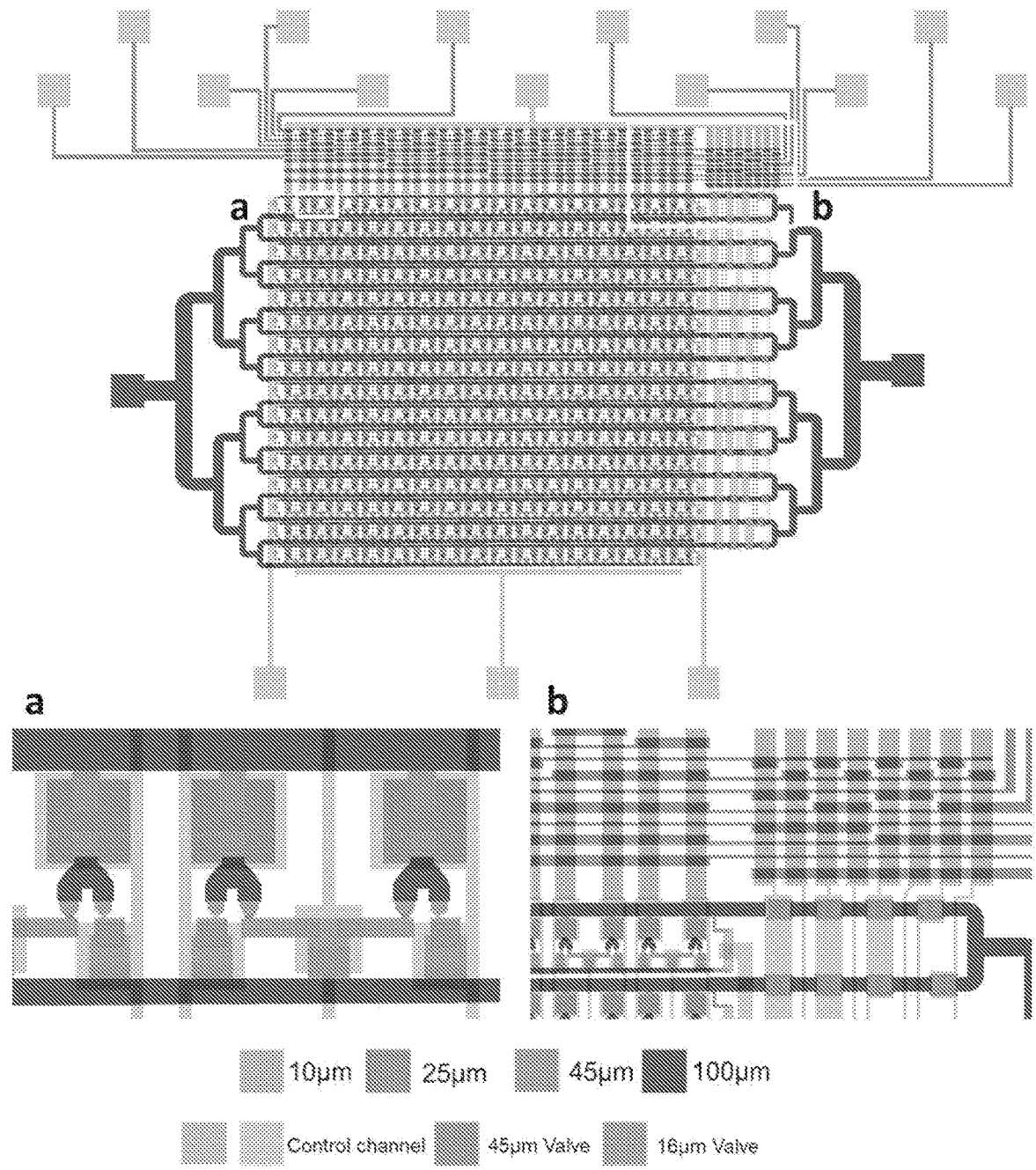
FIG. 25 shows an exemplary design of hydro-Seq addressable multiplexed valve model. (a) A close up view of the bead cell pairing chambers and valves. (b) View of the valve multiplexer structure with row and column control channels.

Chambers containing cells of interest are selectively addressed using a multiplexed valve structure. FIG. 25 shows a schematic layout of a chip with addressable multiplexed valves. Such a device enables selective bead retrieval by opening a particular column of chambers while simultaneously opening a valve controlling the retrieval flow in a particular row. FIG. 25b shows the valve configuration surrounding each chamber. The cell control valve and main entrance valve are connected to the same pressure line. This pressure line is addressable by the column multiplexer. The bead valves of each chamber are connected to a single pressure source. The row multiplexer controls the retrieval flow in the main channel. During a selective retrieval operation, the pressure is released in the desired column of valves. Nest, the corresponding row valve is released, allowing fluid to flow from the outlet to the inlet in a single row. Finally, the bead valves are opened, and the retrieval flow in the selected chamber allows the bead to exit the chip. This design allows higher sample purity and guarantees target cells identified by microscopy are selected for downstream analysis.

Chamber of Origin Barcoding

Figure 26:
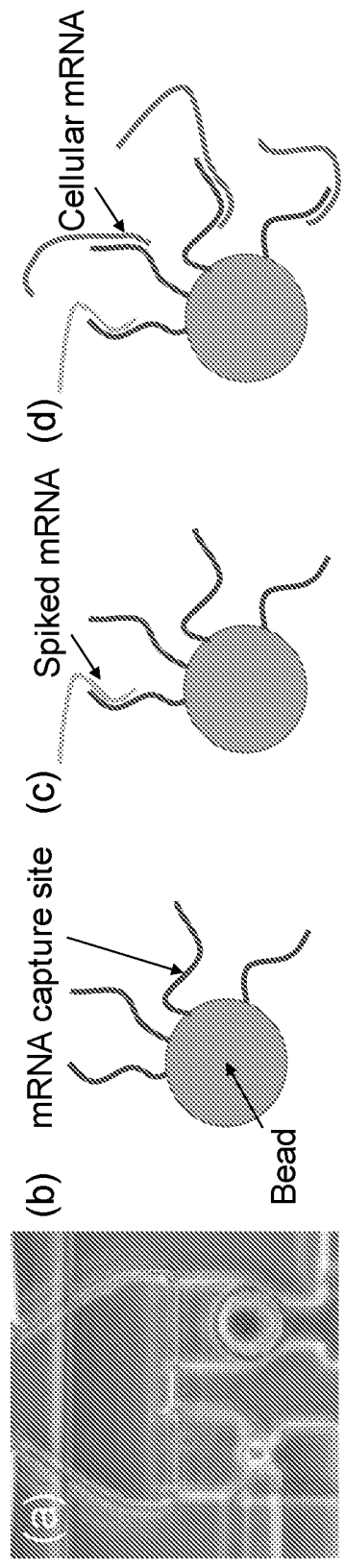
FIG. 26 shows barcode mRNA embodiments with barcodes introduced prior to cell lysis. (a) Bead cell pairing in a microfluidic chamber. (b) Schematic of a bead after bead-cell pairing and before introducing barcoding mRNA. (c) After introducing the barcoding (spiked) mRNA with the multiplex valve, the mRNA attaches to the bead. (d) After cell lysis, the mRNA from the cell attaches to the rest of the capture sites.
Figure 27:
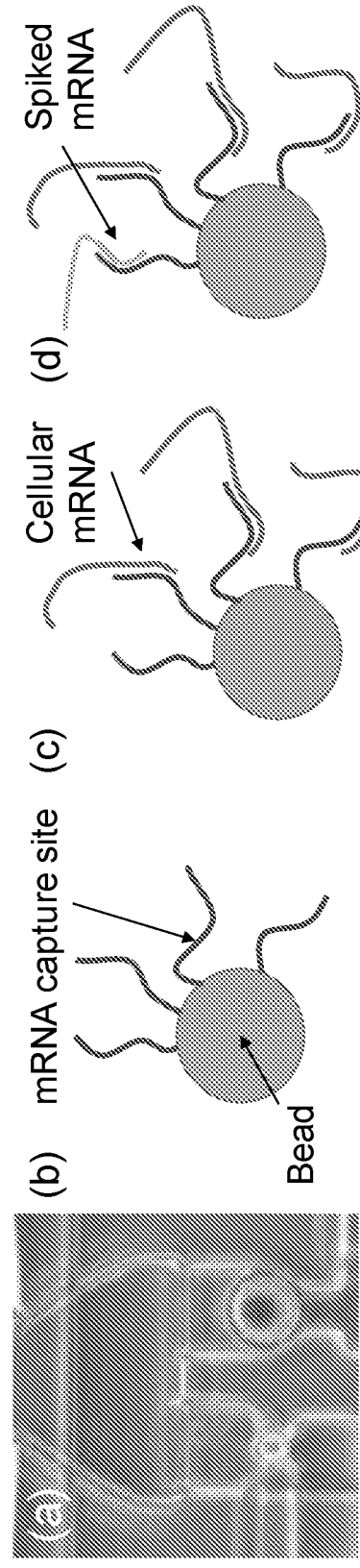
FIG. 27 shows barcode mRNA embodiments with barcodes introduced after cell lysis. a) Bead cell pairing in a microfluidic chamber. (b) Schematic of a bead after bead-cell pairing and before introducing barcoding mRNA. (c) After introducing the barcoding (spiked) mRNA with the multiplex valve, the mRNA attaches to the bead. (d) After cell lysis, the mRNA from the cell attaches to the rest of the capture sites.

To identify the chamber of origin for the beads, different known sequences of mRNA are introduced into each chamber on chip after bead-cell pairing (FIGS. 26 and 27). The spiked mRNA attaches to the barcoded bead inside the chamber of interest. The chamber can be selected using multiplex addressable valves to allow the spiked mRNA to only enter one specific chamber or a group of selected chambers. The sequence of the known mRNA should be different from the mRNA of human or other target cells, so the barcoding sequence can be distinguished from sequence of cellular gene expression. This barcoding technique enables many different applications. For example, single-cells in the chambers can be imaged and studied with the correlation between the gene expression and observed cellular property. With the capability to culture cells in chamber, different cellular properties such as drug susceptibility, immunostaining, and cell morphology can be studied with the transcriptome readout. In addition to different mRNA sequences, the combination of several mRNAs can be used as the barcode as well.

Example 2

Methods
Device Fabrication

The devices were made using soft-lithography fabrication process. The multi-layer layout of the chip was designed using AutoCAD 2016 (Autodesk®). The masks for photolithography were made using a mask making instrument (μPG 101, Heidelberg instruments). The mold for the flow channel was fabricated with 10 μm, 20 μm, 40 μm, and 100 μm thick SU-8 (Microchem) following the manufacturer's protocol. The valves were created using AZ®9260 (AZ Electronic Materials) with peak thickness of 15 μm and 45 μm after thermal reflow. The mold for the control channels was fabricated with 20 μm SU-8. The SU-8 mold was treated by vaporized Trichloro(1H,1H,2H,2H-perfluorooctyl) silane (448931 ALDRICH) under vacuum overnight to promote the release of cured PDMS. After coating, the mold was heated at 150° C. on a hot plate for 10 minutes. PDMS (Sylgard 184, Dow Corning) was prepared by mixing with 10 (elastomer): 1 (curing agent) (w/w) ratio, poured on flow channel molds, and cured at 85° C. overnight before peeling. Thin film of PDMS was spun onto the control channel mold and cured at 85° C. for one hour. After peeling the PDMS from the flow control mold, the PDMS piece and the thin film PDMS were treated using oxygen plasma (80 W for 60 seconds) and bonded using MJB3 aligner (Karl Suss). The devices after bonding were heated at 80° C. overnight to ensure bonding quality.

Cell Culture

Different cell lines, including MDA-MB-231, MDA-MB-231 GFP, HEK293, and 3T3 were cultured in petri dishes for device testing. MDA-MB-231, MDA-MB-231 GFP, HEK293 and 3T3 cells were cultured in DMEM (Gibco 11965) with 10% FBS (Gibco 10082) and 1% penicillin/streptomycin (Gibco 15070). All the cells were cultured and passaged when cells reached over 80% confluency in the dish.

Image Acquisition

The microfluidic devices were imaged using an inverted microscope (Nikon) with a XYZ motorized stage (ProScan II, Prior Scientific). The bright-field and fluorescent images were taken with a 4× objectives and a 10× objectives with a charge-coupled device (CCD) camera (Coolsnap HQ2, Photometrics). A FITC and a UV-2A filter cube were used for the fluorescent imaging. To ensure optimized image quality, auto-focusing was done after imaging every 5 frames. After scanning, the Nikon NIS-Elements Basic Research software module was used to stitch individual images to a large image for analysis.

Sealing Test

Before testing, the device was placed in a desiccator with vacuum pressure for 20 minutes. After the vacuum process, the device was primed using a 5% (w/w) PEO-terminated triblock polymer (Pluronic® F108, BASF) in DI-water for 20 mins. The small-molecule dye solution (fluorescein 5(6)-isothiocyanate, F3651, Sigma-Aldrich, molecular weight of 389 Daltons) was used to test the leakage of valves in Hydro-Seq chips. After flowing PBS through the chip, all chamber valves were closed, and dye solution was introduced to the branch channel. The chip was then imaged at 0 minute, 10 minutes, and 20 minutes after dye introduction to test the sealing of chambers.

Hydro-Seq Device Priming and Preparation

For scRNA-sequencing, the device was heated at 150° C. to deactivate enzyme activities on chip for 30 minutes. The device was then placed in a desiccator with vacuum pressure for 20 minutes. After the vacuum process, the device was sanitized using UV radiation and primed using a 5% (w/w) PEO-terminated triblock polymer (Pluronic® F108, BASF) in DI-water for 20 mins. Before cell loading, channels were washed by flowing through 150 μL phosphate-buffered saline (PBS). To enable pneumatic valve control, the tubing filled with DI water was then connected to designated ports with back pressure 25 PSI when activated. The syringe pump was connected to the outlet of the chip to drive the cell loading process.

Cell Capture Efficiency Test

MDA-MB-231 cells were first stained by green Cell-Tracker dye (ThermoFisher C2925) with 10 μM concentration following manufacturer's protocol and then suspended using Trypsin-EDTA (Gibco 25200). Cell concentrations were first calculated using a hemocytometer, and cells were diluted to the concentration 500 cells/mL. After preparing the chip, the cell suspension was sampled three times by loading 100 μL of the solution to a well in a 96-well plate. Each well was imaged using fluorescent imaging and counted to verify that each 100 μL solution contains 50 cells in average. After sampling, another 100 μL cell solution was then loaded to the Hydro-Seq chip by directly inserting the pipette tip to the inlet. The solution was then loaded with 10 μL/min flow rate until emptying the pipette tip. During cell loading, bead valves and wash channels were closed to prevent cells from passing by. After loading cell suspension, the pipette tip was then removed and another 20 μL PBS was added to the inlet and loaded to ensure all the cells in the inlet and branching channels were loaded to the chip. The chip was then imaged using large area fluorescent imaging to quantify the number of captured cells. To evaluate the number of captured cells after washing, the washing protocol was applied to the captured cells. The bead valves were then open and 100 μL of PBS was flushed with 50 μL/min flow rate from the inlet to the outlet. After flushing, the bead valves were closed again. Then, 100 uL of fresh PBS was added to the outlet and withdrawn from the outlet to the inlet by a pipette. The withdrawn 100 uL solution was then reloaded back to the chip again with 10 μL/min flow rate. The chip was imaged again using fluorescent microscopy for cell quantification. Finally, the beads are loaded with a 150 μL bead solution with 10K beads/mL concentration with 50 μL/min flow rate. During the bead loading, only the wash channels at the upstream branch channels remained closed.

After bead loading, the chip was imaged using fluorescent microscopy to quantify the number of bead cell pairs.

Cell Capture Efficiency Test of the Enriched Spike Samples

MDA-MB-231 cells were first stained by green Cell-Tracker dye (ThermoFisher C2925) with 10 µM concentration following manufacturer's protocol and then suspended using Trypsin-EDTA (Gibco 25200). Cell concentrations were first calculated using a hemocytometer, and cells were diluted to the concentration 2000 cells/mL. 100 µL of the cell solution was then spiked to 7 mL of whole blood from healthy donors. The blood sample was then processed by Celsee following manufacturer's protocol. The enriched CTC sample was then spun down to 200 µL from 4 mL. The solution was then pipetted up and down gently for mixing. After mixing, the first 100 µL solution was used for cell loading following the protocol in cell capture efficiency test. The second 100 µL solution was then taken to a well in 96-well plate to quantify the number of cells in the enriched sample. The well was scanned after 30 minutes to ensure cells precipitate to the bottom of the well for fluorescent imaging.

Mixed Species Experiment

HEK293 were stained with CellTracker Red (ThermoFisher C34552) and 3T3 cells were stained with Cell-Tracker Green (ThermoFisher C2925) following manufacturer's protocol. HEK293 and 3T3 cells were suspended using Trypsin-EDTA (Gibco 25200) and diluted into 25 k cells/ml in PBS. The cell suspension solution was then loaded into the device inlet and cells were driven into the chip by syringe pump with flow rate 10 µL/min. The valves after the bead capture sites were closed during cell loading. After cell loading, all valves were closed and the residual cells in the inlet and channels were washed away using PBS. Beads stored in TE buffer were then re-suspended in PBS twice and loaded into the chip with 20 k beads/ml by gravity flow. During the loading all the chamber valves were opened to enable bead-cell pairing inside the chambers while wash channels remain closed. Since the beads settle down easily in the inlet, it's required to pipette up and down during the loading process to redistribute beads in the suspension. After bead-cell pairing, the chamber valves were again closed, and wash channels were opened to allow cell lysis buffer to flow into the branch channel. Then, the chamber valves were open for 5 second to allow lysis buffer to enter the chamber for cell lysis. After lysis, the devices were tilted to move the beads to cell capture site and incubated for 20 minutes for mRNA capture. Finally, the valves were opened, and beads were retrieved by drawing 200 µL of PBS from the outlet to the inlet using a pipette. The retrieved beads were then processed for sequencing according to Drop-Seq protocol.

Patient Sample CTC Sequencing Experiments

Whole blood from patients with metastatic breast cancer was obtained. For experiments with Celsee purified samples, the blood samples were processed by the Celsee PREP100 system following manufacturer's protocol. For experiments with Labyrinth purified samples, the blood samples were processed using the protocol reported in a prior literature (Lin, E. et al. *Cell Syst.* 5, 295-304.e4 (2017)). For both technologies, the samples were spun down to 100 µl volume after CTC enrichment. After device priming and preparation, the CTC suspension was loaded to the device by inserting the pipette tip filled with the 100 µl solution to the inlet. After closing all the wash channels and bead valves, the suspension was loaded to the chip with 10 µl/min flow rate driven by a syringe pump. After emptying the pipette tip, the tip was removed and 100 µl PBS was added to the inlet. After washing with PBS with 10 µl/min for 2 minutes, the bead valves were opened, and the flow rate was increased to 50 µl/min to wash away residual red blood cells in the chamber. The PBS solution was refilled during the wash process. After washing for 3 minutes, the flow was stopped, and bead valves were closed again. To further remove contaminating cells in the chamber, 100 µl PBS was added to the outlet and a pipette tip was inserted to the inlet to retrieve the solution using a pipette. Then, the solution was loaded back to the chip and washed again using the same protocol in the first loading. After loading CTCs, the beads were loaded to the chip and prepared following the same procedure described in the mixed species session.

Gene Sequencing

Beads were obtained from HydroSeq chip and processed using dropseq protocol including RT (using Thermofisher Maxima RT kit), PCR (using Kapa HiFi Hotstart PCR Readymix), and library preparation (using Illumina Nextera XT Library Prep Kit) (Klein, A. M. et al. *Cell* 161, 1187-1201 (2016)). The DNA were quantified and pooled by the University of Michigan Sequencing Core for sequencing. Ten samples were pooled and sequenced using 1 NextSeq 500 mid-output sequencing lane. Each population is expected to have approximately 10 million reads (paired-end: one side 25 base pairs for barcode and the other side 115 base pairs for mRNA quantification).

Read Alignment and Data Analysis

The sequencing reads were aligned using STAR and processed by the standard flow suggested by Dropseq (Klein, A. M. et al. Cell 161, 1187-1201 (2016)). Then, gene sequencing data were analyzed using Seurat, a R package for single-cell analysis. Cells with more than 800 genes detected were considered as cells. The cells having more than 5% mitochondrial gene expression were discarded for their poor viability. WBCs were removed by eliminating any barcode with any CD45 (PTPRC) expression. RBCs were removed by eliminating any barcode with more than 1% of hemoglobin expression. The residual barcodes were considered healthy CTCs for further analysis. The gene expression was log-normalized for PCA and tSNE. Cell clustering was performed based on shared nearest neighbor (SNN) method. For pathway analysis, 500-1,000 significant top-ranked genes were identified using Seurat. Then, the significantly differential genes were applied to Enrichr, and the pathway dataset of NCI-Nature 2016 was used.

Results

Recent advances in single-cell RNA-sequencing (scRNA-seq) have enabled high-throughput analysis of cellular heterogeneity and identification of cellular types by their gene signatures (Klien et al., 2016, supra; Macosko, E. Z. et al. Cell 161, 1202-1214 (2016); Gierahn, T. M. et al. Nat. Methods 14, 395-398 (2017)). By pairing single barcoded beads with single cells in droplets or micro-wells, the mRNAs from single-cells can be uniquely labelled by a barcode and identified using single-cell whole transcriptome analysis (Macosko et al., supra). However, it is still challenging to apply scRNA-seq to samples containing limited cells of interest (10-100 cells) and massive contaminations such as debris, cell-free nucleic acids, and background cells. Due to severe cell loss in the bead-cell pairing process, thousands of cells are often needed to achieve reliable RNA readout, so rare samples still cannot be handled using current high-throughput techniques (Gierahn et al., supra). In addition, the inability to clean samples allows the barcoded beads to capture background mRNA, obfuscating the scRNA-seq analysis. As a result, when handling contaminated rare samples, single-cell picking is still the primary method to select cells of interests for RNA-sequencing. For instance, to analyze single-cell gene expression of circulating tumor cells (CTCs), cells are stained with fluorescent tags targeting EpCAM or Pan Cytokeratin, so the targeted cells can be selected by capillary suction or dielectrophoretic microfluidics for downstream RNA-seq analysis (Ferreira et al., S. S. Mol. Oncol. 10, 374-394 (2016); Vishnoi, M. et al. Sci. Rep. 5, 1-14 (2015); Lohr, J. G. et al. Nat. Biotechnol. 32, 479-484 (2014)). Those techniques are inadequate by their low throughput caused by slow fluorescent imaging process and sequential cell-picking procedure. The positive selection also skews the sample population, missing an important subpopulation of CTCs in tumor metastasis (Ferreira et al., supra; Lin, E. et al. Cell Syst. 5, 295-304.e4 (2017)). As some clinical samples, such as CTCs and primary biopsies, often contain a limited number of cells with contaminations in the background, it is important to further develop techniques to interface such challenging samples for potential clinical applications (Gierahn et al, supra; Ferreira et al., supra; Lin, E. et al., supra; Chen, Y.-C., et al., Sci. Rep. 6, 27154 (2016)).

Figure 30:
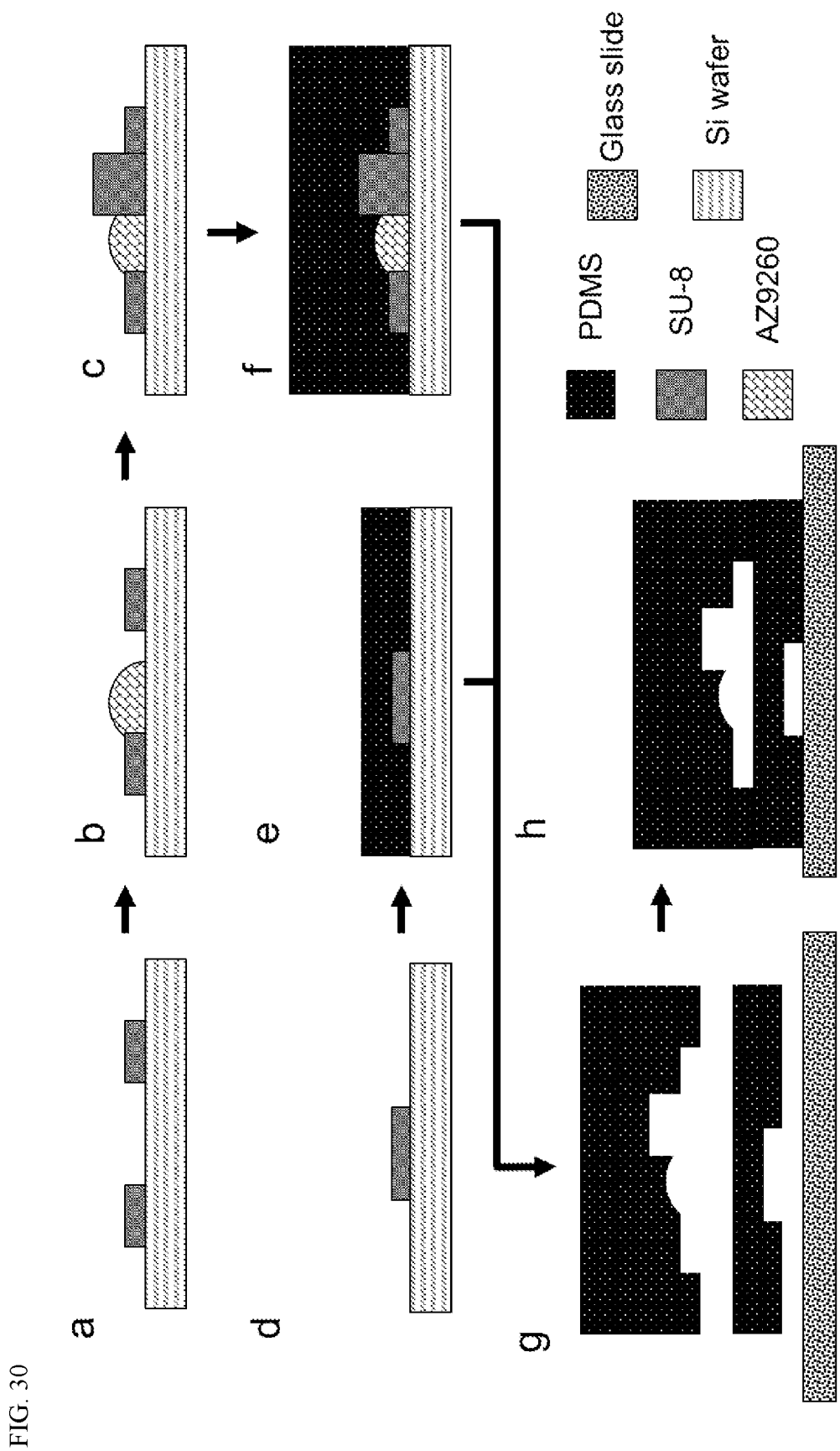
FIG. 30 shows multilayer fabrication for Hydro-Seq. (a) SU-8 patterned on the silicon wafer to create the mold for softlighography fabrication. (b) With photoresist AZ-9260 patterning, the thermal flow process creates curved structure for valve sealing. (c) The flow channel mold is patterned with 2 layers of AZ-9260 patterning and 4 layers of SU-8 with thickness specified in FIG. 31. (d) The valve control channel is made by one layer of SU-8 patterning. (e-f) After multilayer fabrication, self-assembled monolayer of silane coating is then applied to facilitate PDMS peeling. (e) The valve control layer made by spinning a 30 μm PDMS. (f) The flow layer made by pouring 2 mm PDMS on the mold for curing. (g) To assemble the layers together, the flow layer is detached from the mold. After alignment and surface plasma activation, the flow layer is bonded to the control channel. (h) The fabrication completed by attaching the PDMS layers to a glass substrate. (i) Photograph of the fabricated device with a US penny. Four valve control channels are connected to the device for valve manipulation. (j) Photograph of the high-density chamber array.

This example describes Hydro-Seq, a high-cell-capture-efficiency scRNA-seq platform for CTCs and samples with rare cells (FIG. 14g). Hydro-Seq has three main technical advantages: (1) size-based high-efficiency single-cell capture, (2) chamber washing capability for contaminant removal, and (3) scalable array design for massively parallel analysis. Without any channels allowing cells to bypass the capture sites, the massively parallel filter structure enables high-efficiency cell capture (FIG. 30). 800 chambers per chip were implemented to accommodate 1-100 CTCs from 10 mL of patient blood, and the design can be expanded to 12,800 chambers for other applications (Ferreira et al., supra; Cheng, Y.-H., et al., Lab Chip (2016)). In this design, there are 16 branch channels with each channel containing 50 capture chambers. Each chamber contains ~1 nL volume, similar to the well and droplet volume reported in other scRNA-seq methods (Macosko et al., supra; Gierahn et al., supra). For bead-cell pairing, each chamber contains one cell capture site and one bead capture site that can be blocked by different pneumatic valves. To enable cell lysis and other washing processes, two washing channels with valve controls were added to the beginning and the end of each branch channel.

Figure 31:
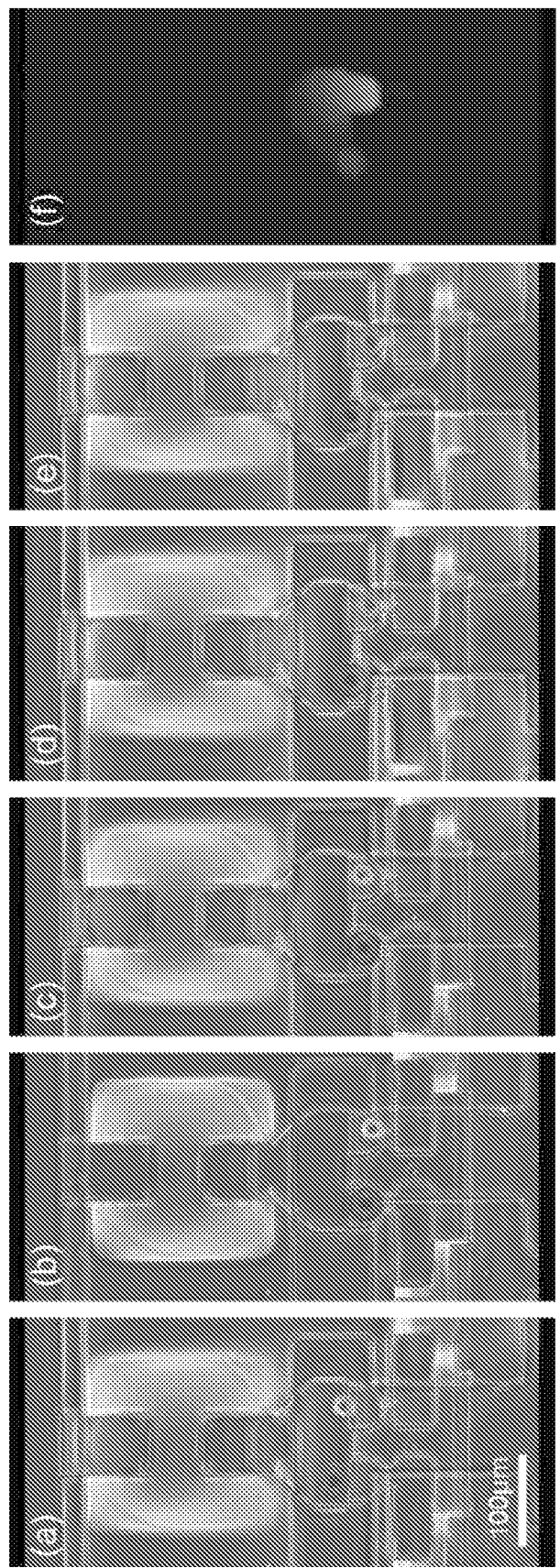
FIG. 31 shows cell lysis in Hydro-Seq. (a) Before lysis, the cell and bead are paired in the chamber with the valves closed. The lysis buffer is loaded to the branch channel. (b) After opening the valve, the flow pushes the bead and cell back to the capture site, and the lysis buffer flows into the chamber. As the cell seals the capture channel, the cell remains intact in the dead volume in the pocket. (c) After closing the valve, the operation creates flow in the chamber, exposing the cell to the lysis buffer. (d-e) The cell is lysed within 30 seconds. (f) The GFP cell releases the cellular content, with the GFP highlighted by fluorescent imaging.
Figure 32:
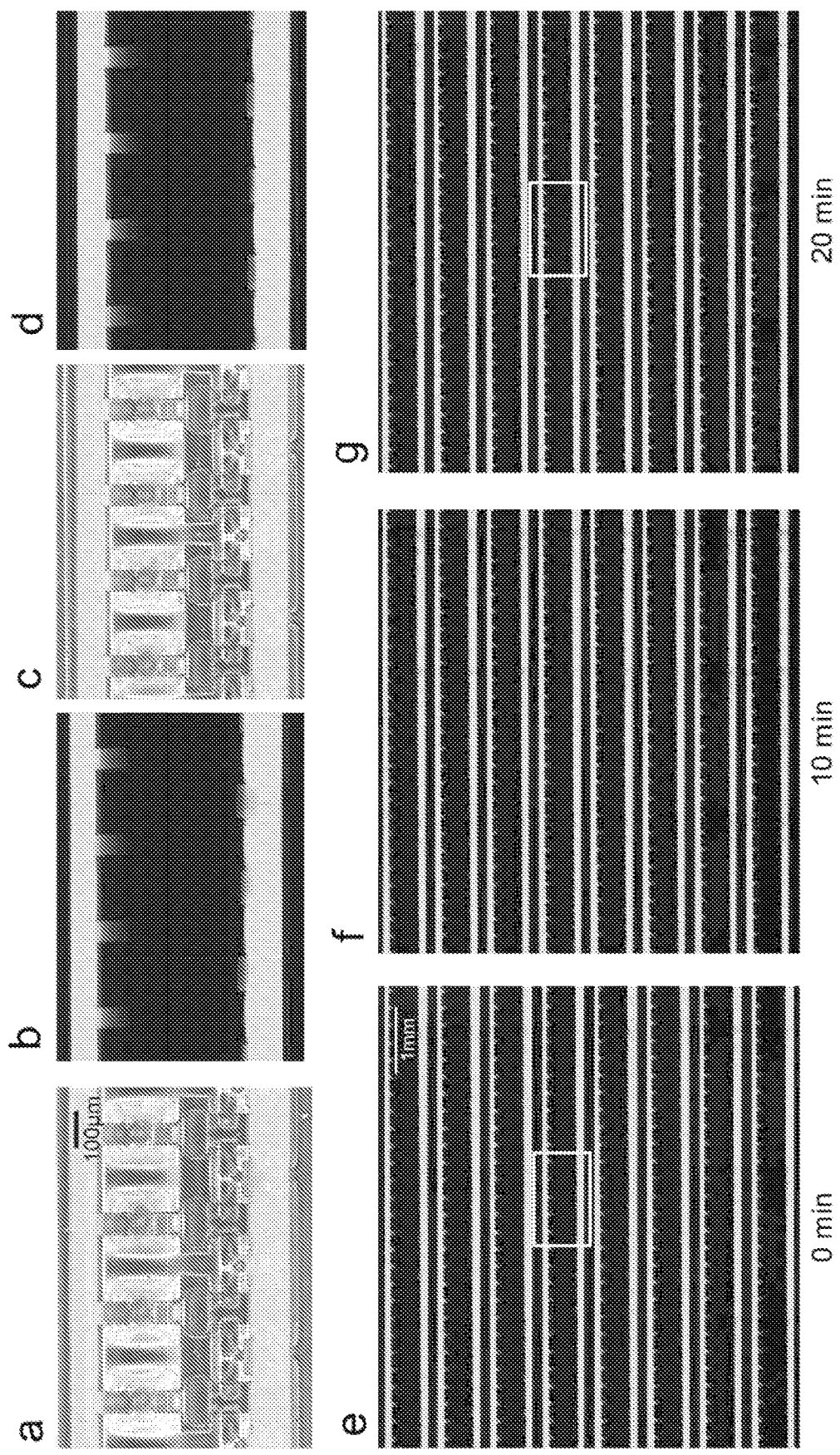
FIG. 32 shows a leakage test of the valve system. (a) Microscopic image showing the parallel chambers isolated by activating the pneumatic valves at 0 minute after introducing the fluorescent dye. (b) The corresponding fluorescent channel of image (a). (c) Microscopic image of the parallel chambers at 20 minutes after introducing the fluorescent dye. (d) The corresponding fluorescent channel of image (c). (e-g) Large area scan imaging highlights chamber isolation at scale at 0 minute (e), 10 minutes (0, and 20 minutes (g) after introducing fluorescent dye. The white box in (e) is shown in (a), and the box in (g) is shown in (c).
Figure 34:
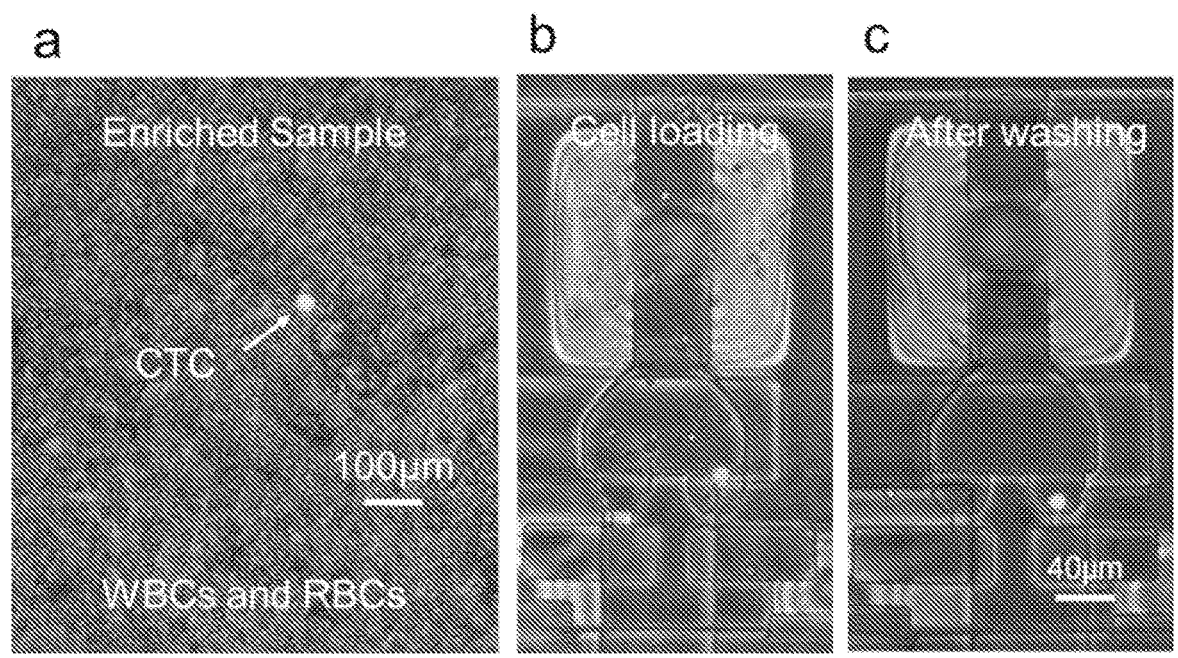
FIG. 34 shows advanced breast cancer patient sample processing with Celsee enrichment technology. (a) The sample after enrichment contains residual red blood cells and white blood cells. (b) During sample loading, CTC is introduced into the chamber with other red blood cells in the chamber. (c) After washing, single cell isolation can be achieved for contamination-free RNA-sequencing.

Before loading CTCs to Hydro-Seq, size-based CTC enrichment was performed using Celsee PREP100 systems (Lin et al., supra). The enriched sample was then transferred to Hydro-Seq for scRNA-seq preparation. During cell loading, the bead flow channels and washing channels were blocked, so CTCs could be captured at the cell capture sites. As breast CTCs are typically larger than other regular blood cells, the cell capture site is designed as a channel with 10 µm×10 µm opening (Ferreira et al., supra). This channel size allows smaller leukocytes, erythrocytes, and platelets to pass through before a larger cell (CTC or larger WBC) blocks the capture site (FIG. 14g). After cell loading, the bead capture site was then opened to wash away the contaminations remained in the chamber (FIG. 14g, FIG. 34). The barcoded beads were then loaded into the chip to pair with the captured cells (FIG. 14g). Since the beads have an averaged diameter of 40 µm, the bead capture site was designed with a 20 µm×25 µm opening. Cell lysis buffer was introduced into the chambers to lyse cells, and the released mRNA hybridized onto the barcoded beads (FIG. 14g and FIG. 31). Finally, the barcoded beads were retrieved with a back flow for downstream sequencing procedures, including reverse transcription, amplification, library preparation and paired-end sequencing (FIG. 14g). With the precisely controlled hydrodynamic capture operation, single-CTCs were captured and paired with barcoded beads for scRNA-seq with high purity, high efficiency, and high throughput.

To demonstrate high cell capture efficiency, cell loading tests were performed with ~50 cancer cells spiked in 100 µL PBS and 90.86±1.6% capture efficiency was achieved. To validate the performance on enriched blood samples, the CelSee CTC enrichment system was applied to spiked blood samples and 90.43±6.08% cell capture efficiency was achieved with similar input cell numbers. Since there is no bypass channel for cells to escape, the deficiency is caused by the loss in the loading interface (cells adhering to the sidewall of inlet or pipette tip). After cell capture, a washing procedure was applied to remove contaminating cells and 89.70±5.06% of the captured cells remained in the capture chambers after the washing step. Finally, 89.60±6.39% of the remaining cells were successfully paired with a single bead for barcoding mRNAs. Considering all the losses from cell loading, washing, and bead pairing, 72.85±2.64% of the initially loaded cell populations was successfully processed on chip.

Figure 33:
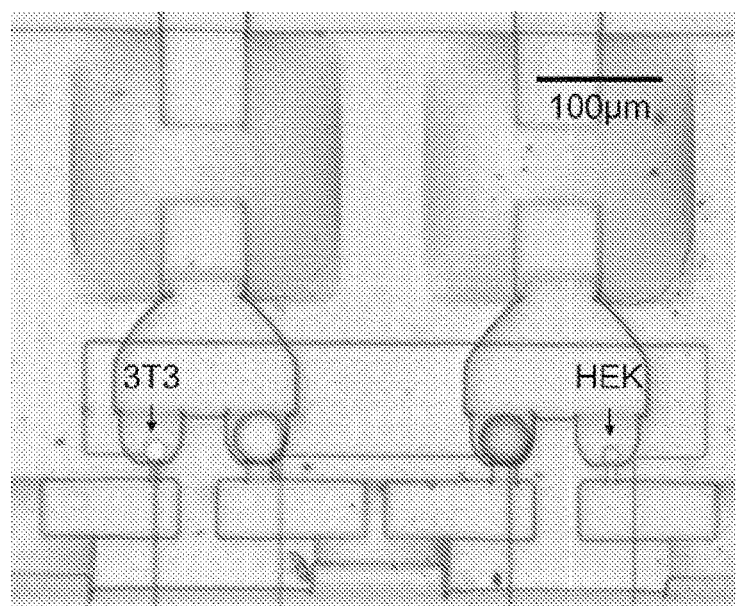
FIG. 33 shows the results of species mixing experiment. (a) Chambers with beads paired to a mouse cell (3T3) and a human cell (HEK). Fluorescent imaging was applied to examine the pairing condition and optimize the capture. (b) Histograms of the percent cross-species contamination of Hydro-Seq.
Figure 33:
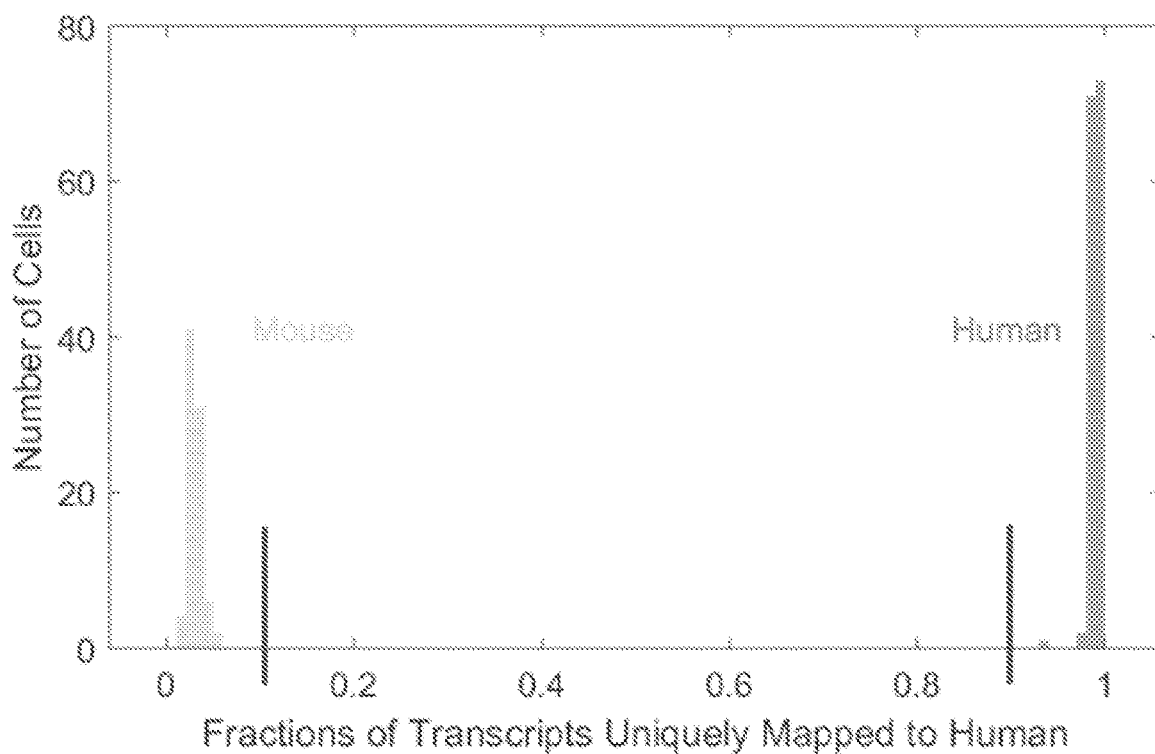

To assess the single-cell resolution, mixed species experiments were performed using a mixture of human cells (HEK) and mouse cells (3T3). After bead-cell pairing, fluorescent imaging was used to confirm that 156 human cells and 80 mouse cells successfully paired with barcoded beads without two cells from different species in the same chamber (FIG. 33a). In the design, cells captured in a chamber prevent the next cell being captured in the same chamber. Even if a cell tailgates after another cell into the chamber, the second cell is removed during washing. Using shallow sequencing (~60,000 reads for cell), the mixed species sequencing results also highlighted highly organism-specific libraries without any mixed genotype cell (FIG. 31b). Using 800 genes per cell as a threshold, 147 human and 84 mouse cells were recovered, consistent with the number of cells observed using fluorescent microscopy. The species-mixing experiment result highlights the high quality of library generated by the presented technology, and low cross-contamination rate is especially valuable in discovering rare cell subpopulations.

Figure 28:
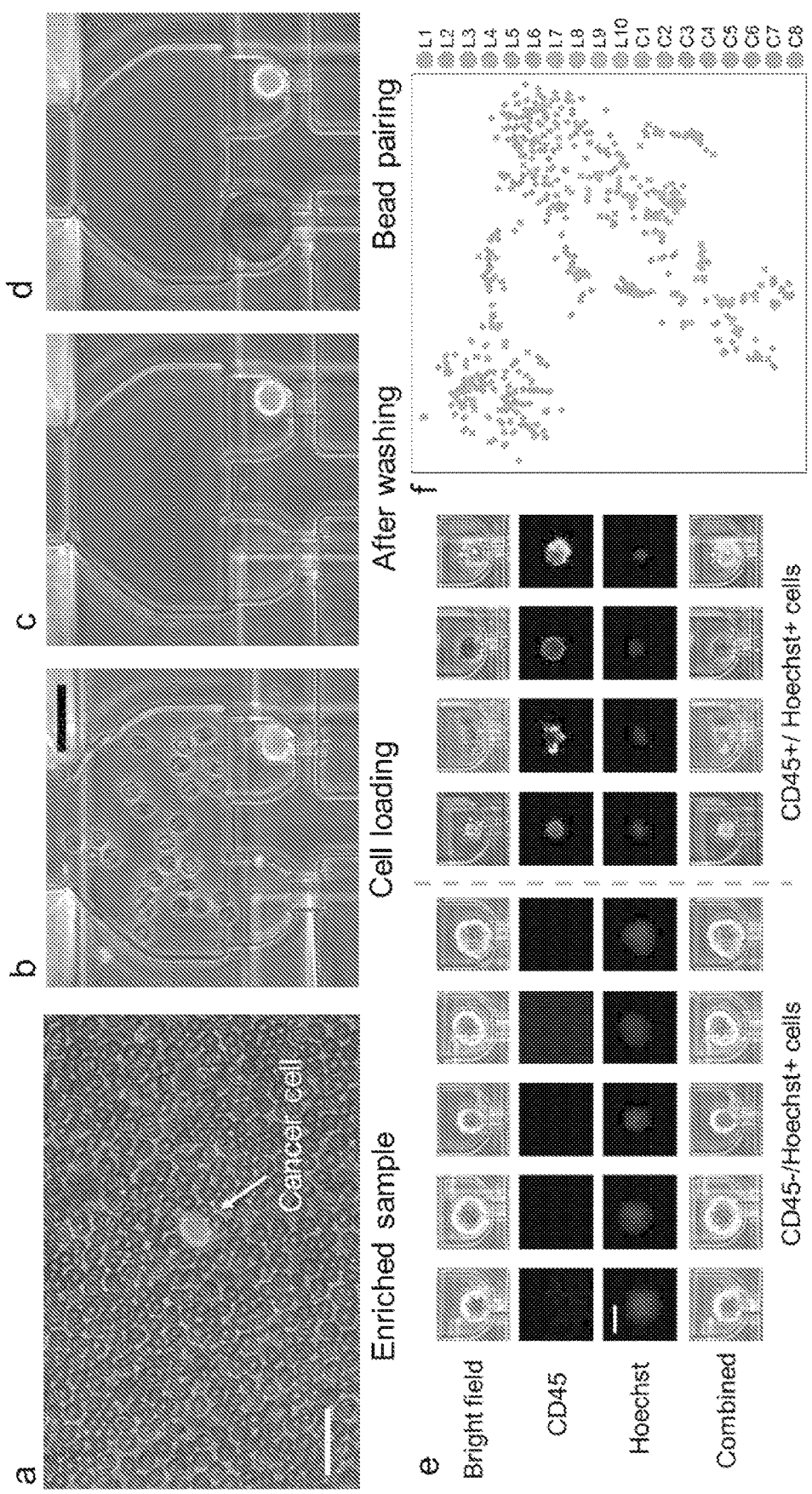
FIG. 28 shows CTC loading in Hydro-Seq. (a) After cell enrichment by Labyrinth, large scale scRNA-seq of the CTCs is challenged by the presence of background blood cells. (Scale bar: 50 μm) (b) Red cells flowing through the chamber during sample loading. (Scale bar: 50 μm) (c) By opening the bead valve, blood cells can be removed through the bead capture flow channel, achieving contamination-free single cell isolation for bead pairing. (d) Paring of the bead to a single cell for scRNA-seq. (e) With CD45 and Hoechst staining, larger CD45 negative cells were identified, showing capture of CTCs. (Scale bar: 20 μm) (f) tSNE plot of all patient samples processed by Hydro-Seq.
Figure 29:
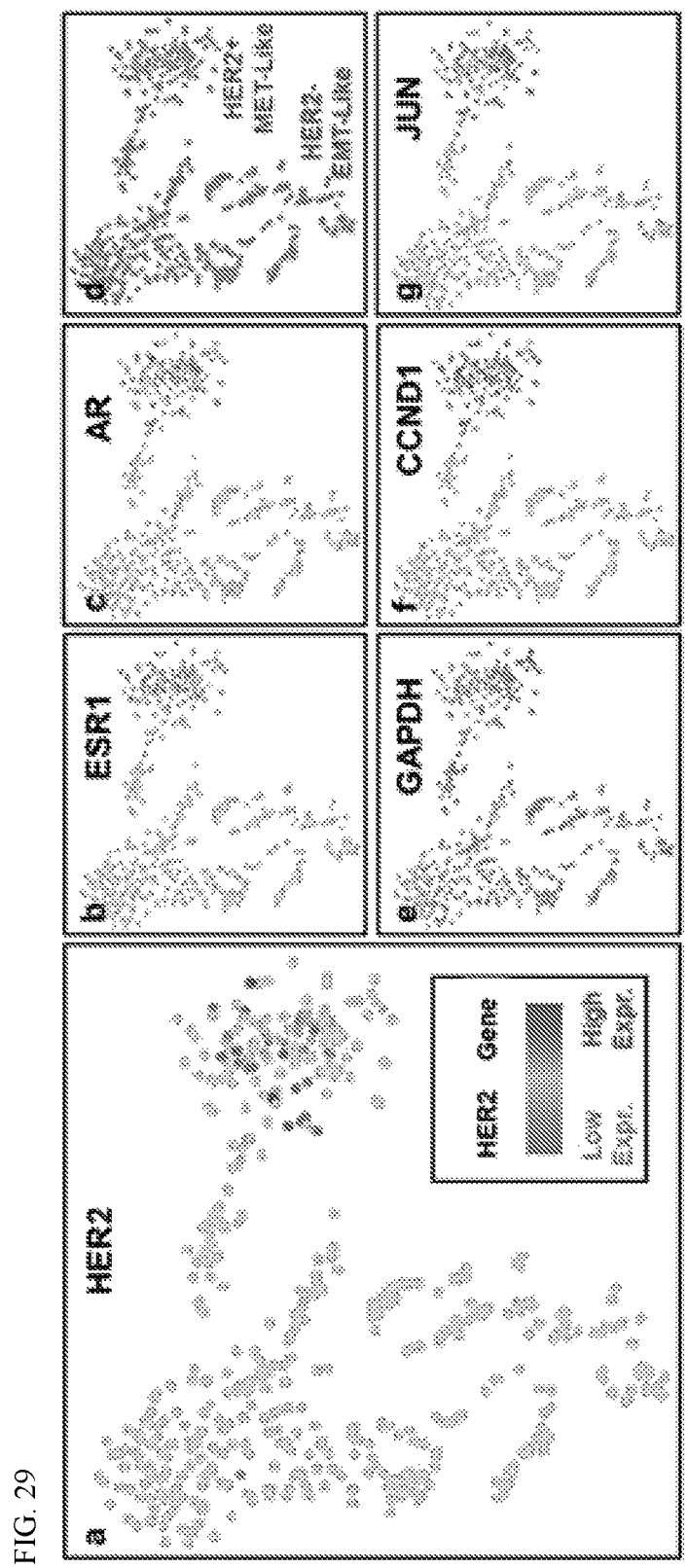
FIG. 29 shows gene expression, clustering, and pathway analysis of breast CTCs. (a-c) The expression of clinical markers: (a) human epidermal growth factor receptor 2 (HER2/Erbb2), (b) estrogen receptor (ESR1), and (c) androgen receptor (AR). (d) The clustering and separation of HER2+ MET-Like and HER2− EMT-Like CTCs. (e-l) The expression of housekeeping, EMT, MET genes: (e) housekeeping gene (GAPDH), (f) cyclin D1 (CCND1), (g) JUN, (h) Keratin-18 (KRT18), (i) Cadherin-1 (CDH1), (j) Epithelial Cell Adhesion Molecule (EPCAM), (k) EMT transcription factor (ZEB2), and (l) transforming growth factor β (TGFB1). (m) The clustering and separation of HER2+ MET-Like and HER2− EMT-Like CTCs from patient 2H. (n) Top-ranked pathways distinguishing HER2+ MET-Like and HER2− EMT-Like CTC populations.
Figure 29:
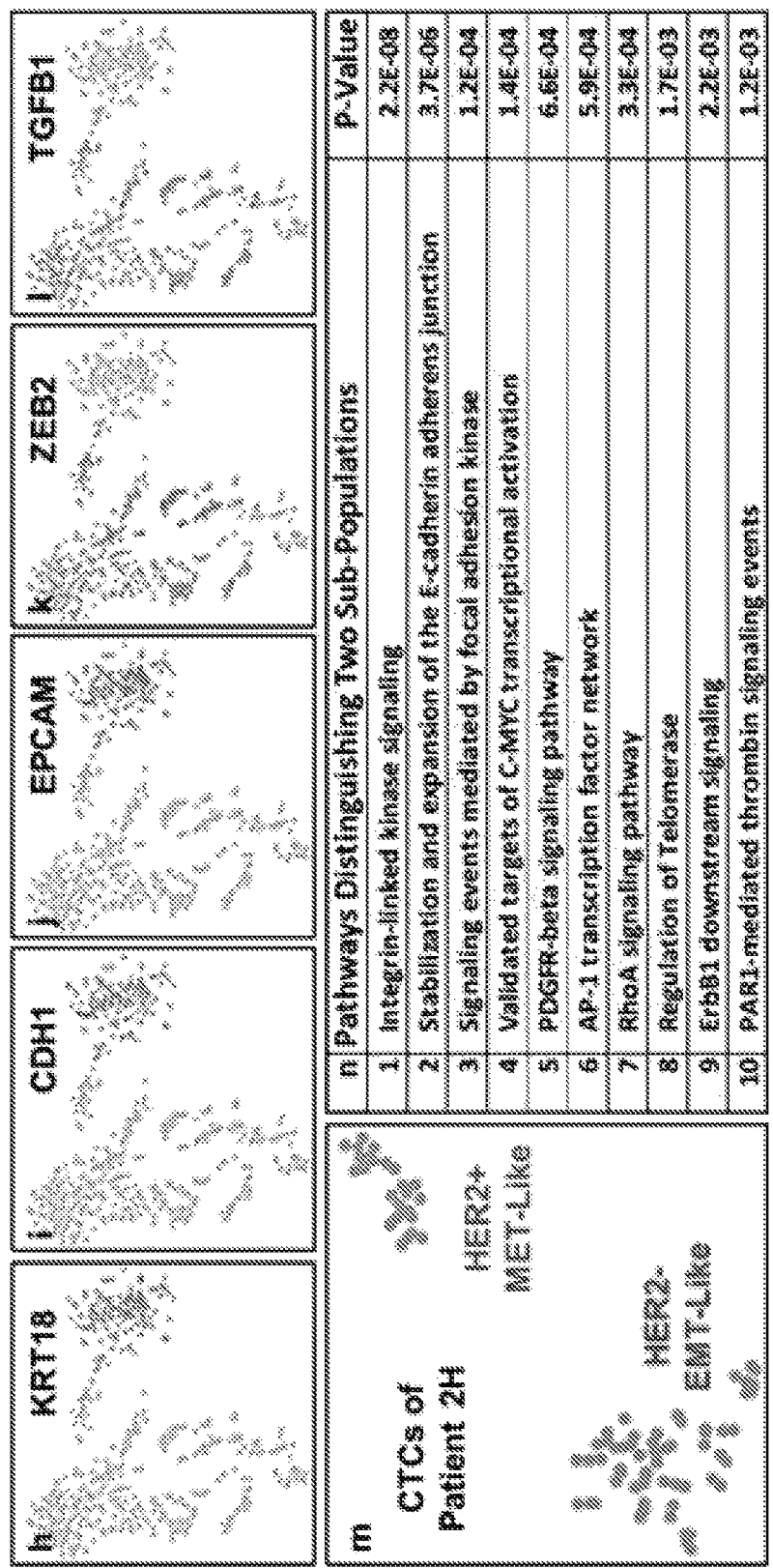
Figure 35:
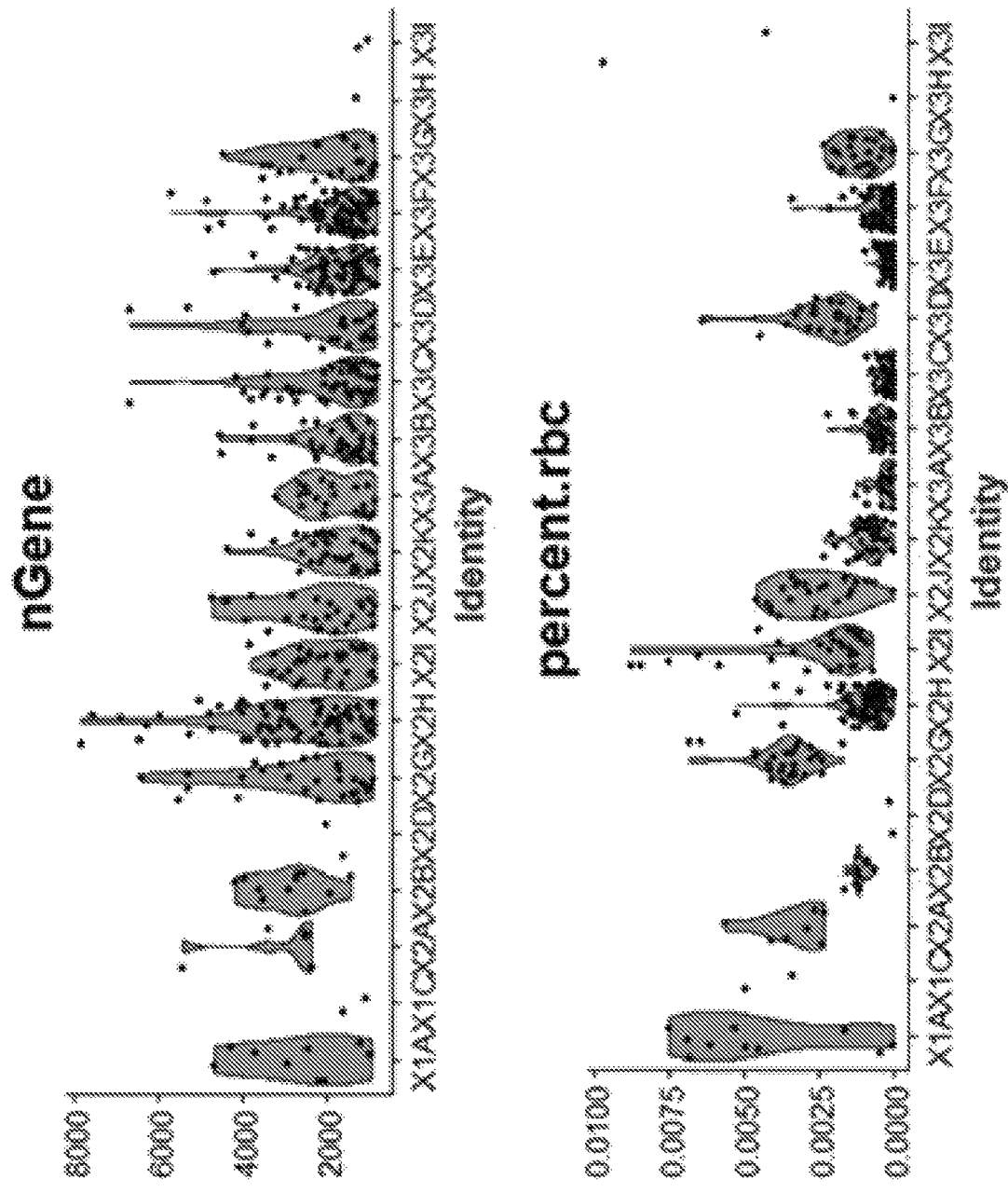
FIG. 35 shows the number of genes (nGENE), percentage of mitochondrial genes (percent.mito), percentage of RBC genes (percent.rbc), percentage of WBC genes (percent.wbc) of each patient sample.
Figure 35:
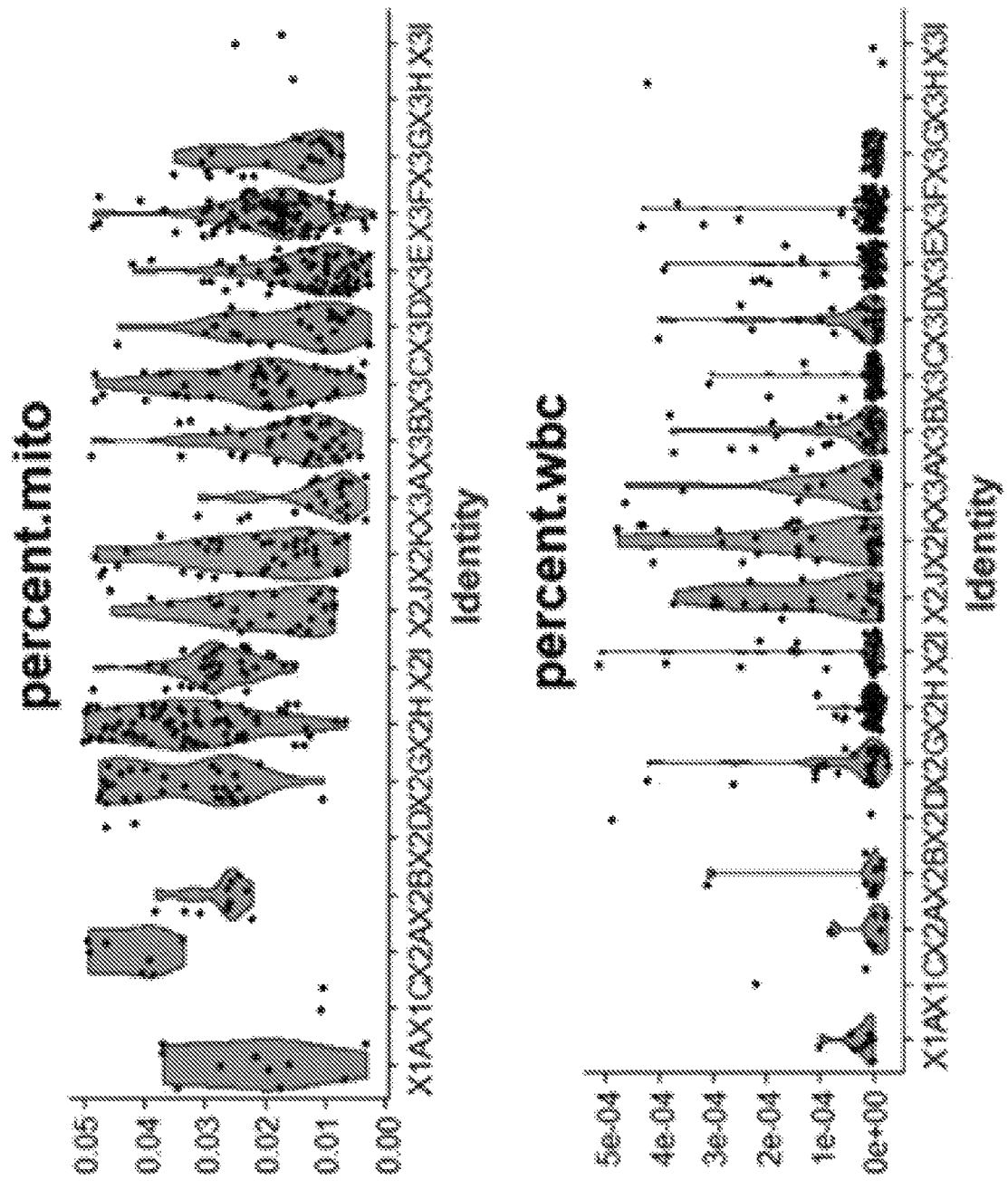
Figure 36:
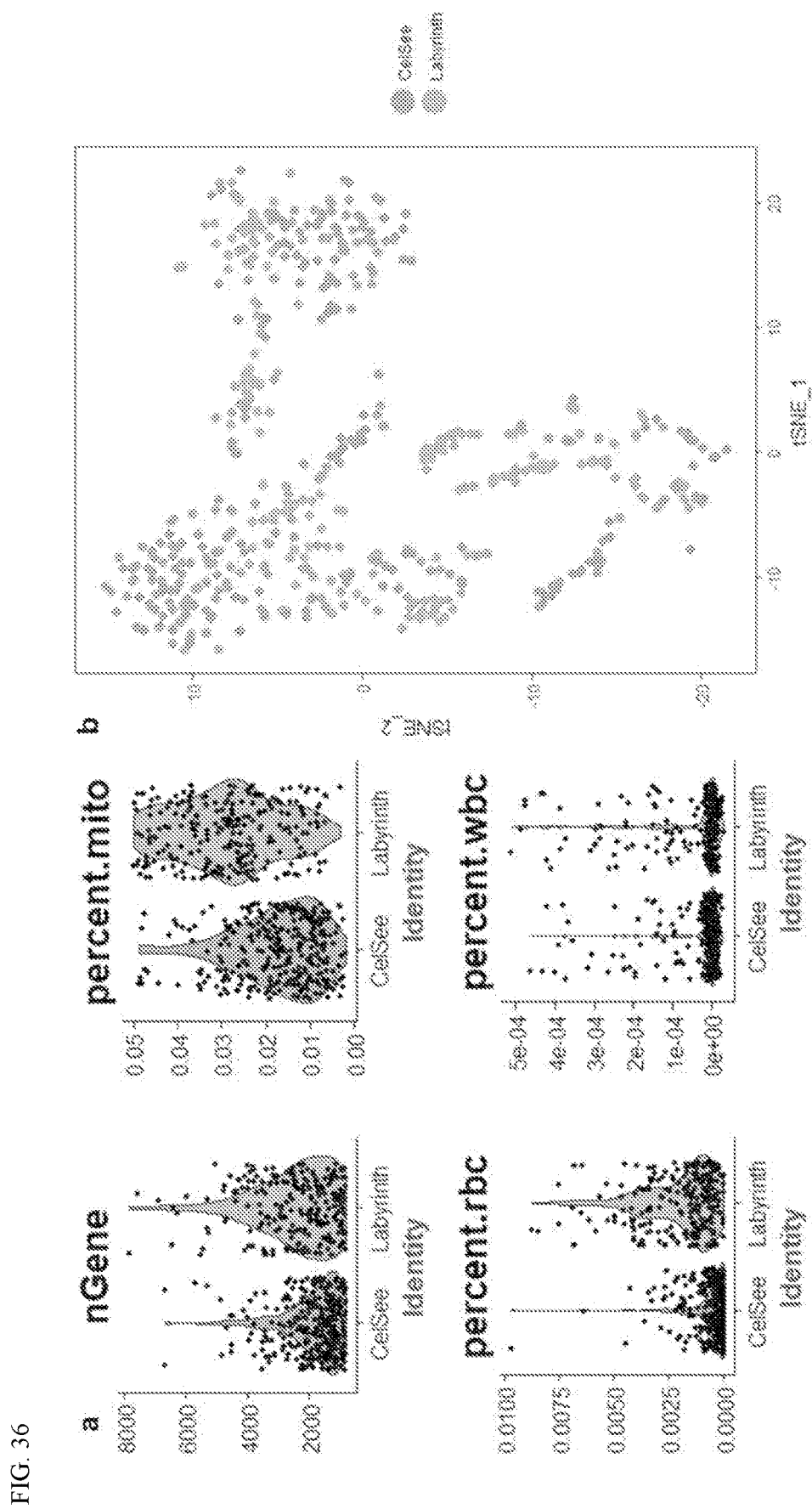
FIG. 36 shows a comparison between two upstream enrichment methods: Celsee and Labyrinth. (a) The number of genes (nGENE), percentage of mitochondrial genes (percent.mito), percentage of RBC genes (percent.rbc), percentage of WBC genes (percent.wbc) of each method. Each dot represents a CTC. (b) The tSNE plot of 550 CTCs from 19 patient samples. Red dot represents a CTC processed by CelSee, and blue dot represents a CTC processed by Labyrinth.
Figure 37:
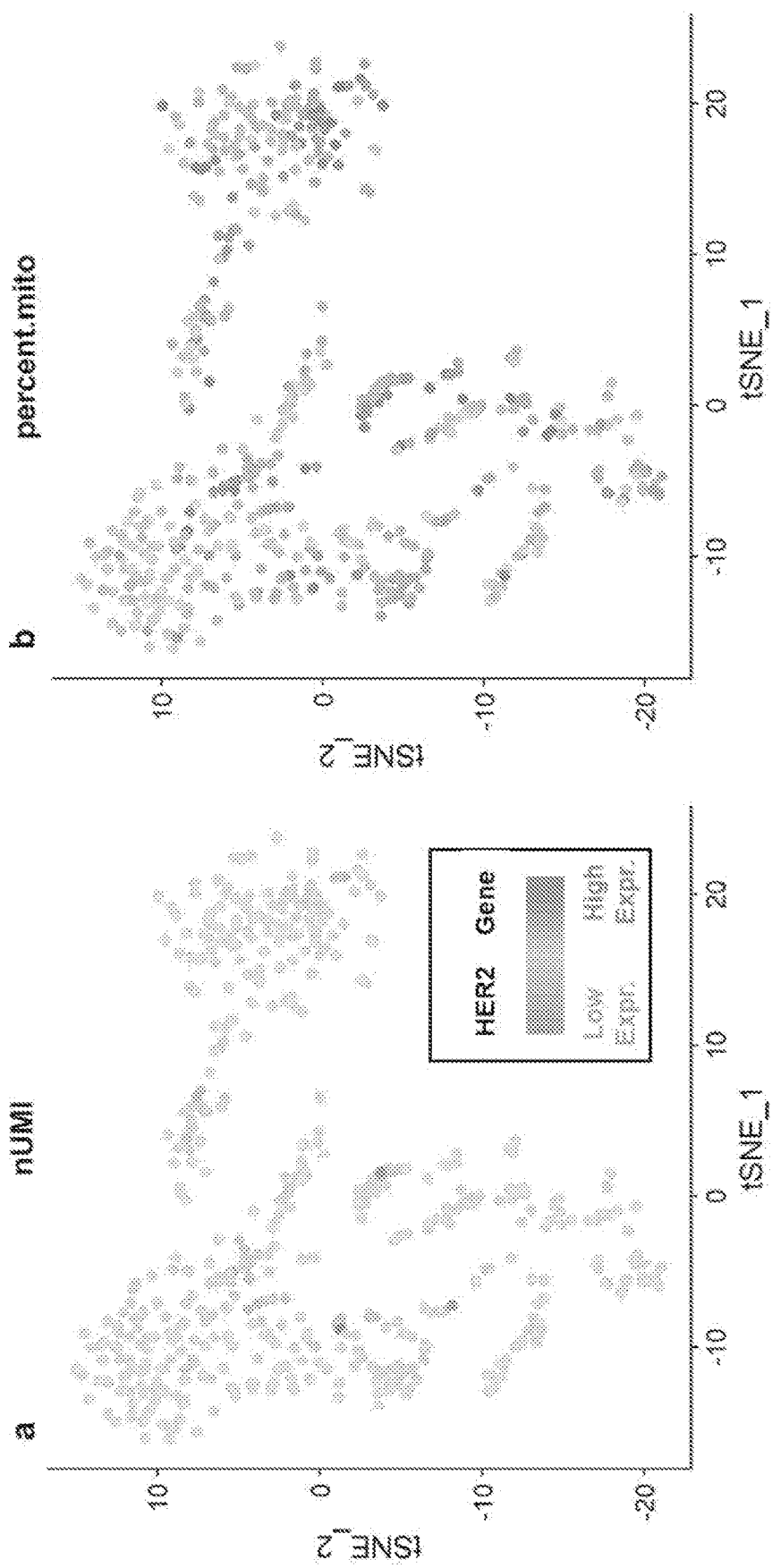
FIG. 37 shows the number of transcripts (UMI) and percentage of mitochondrial genes (percent.mito) detected per cell.
Figure 38:
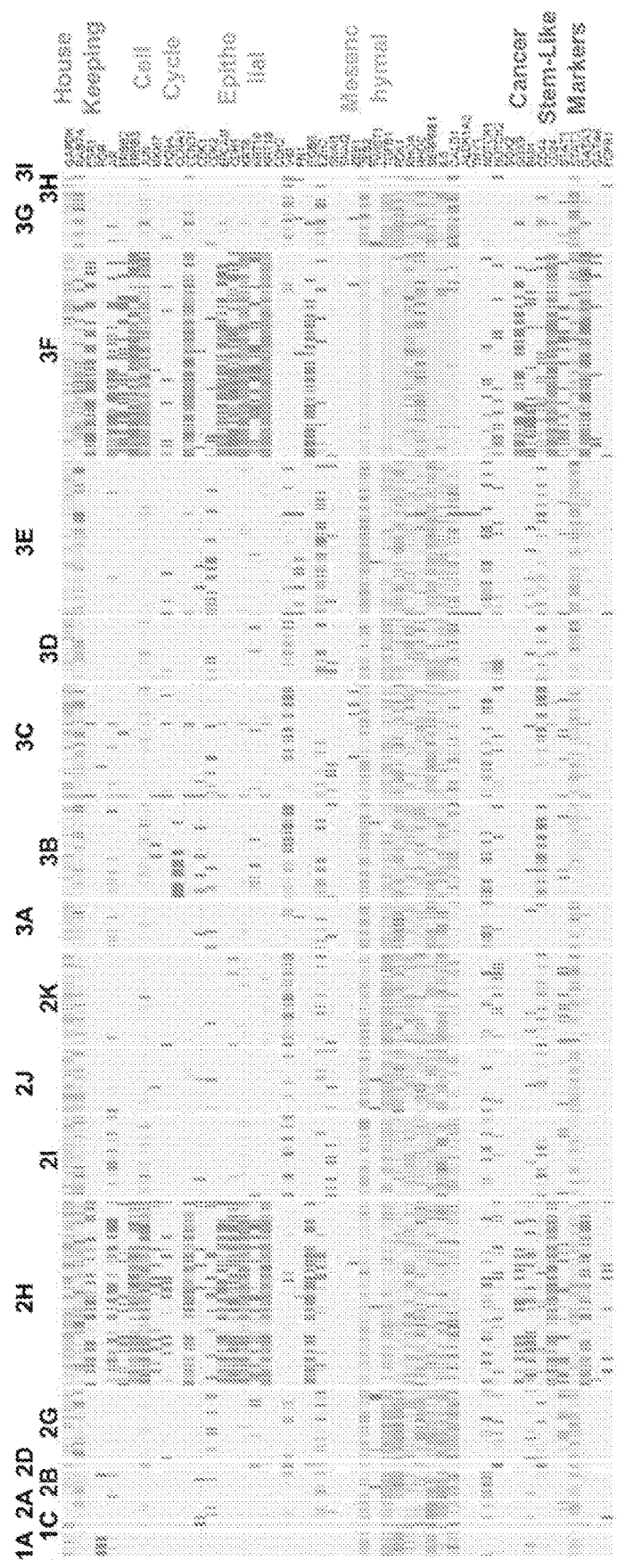
FIG. 38 shows a heatmap of critical housekeeping, cell-cycle, epithelial, mesenchymal, and cancer stem-like markers.
Figure 39:
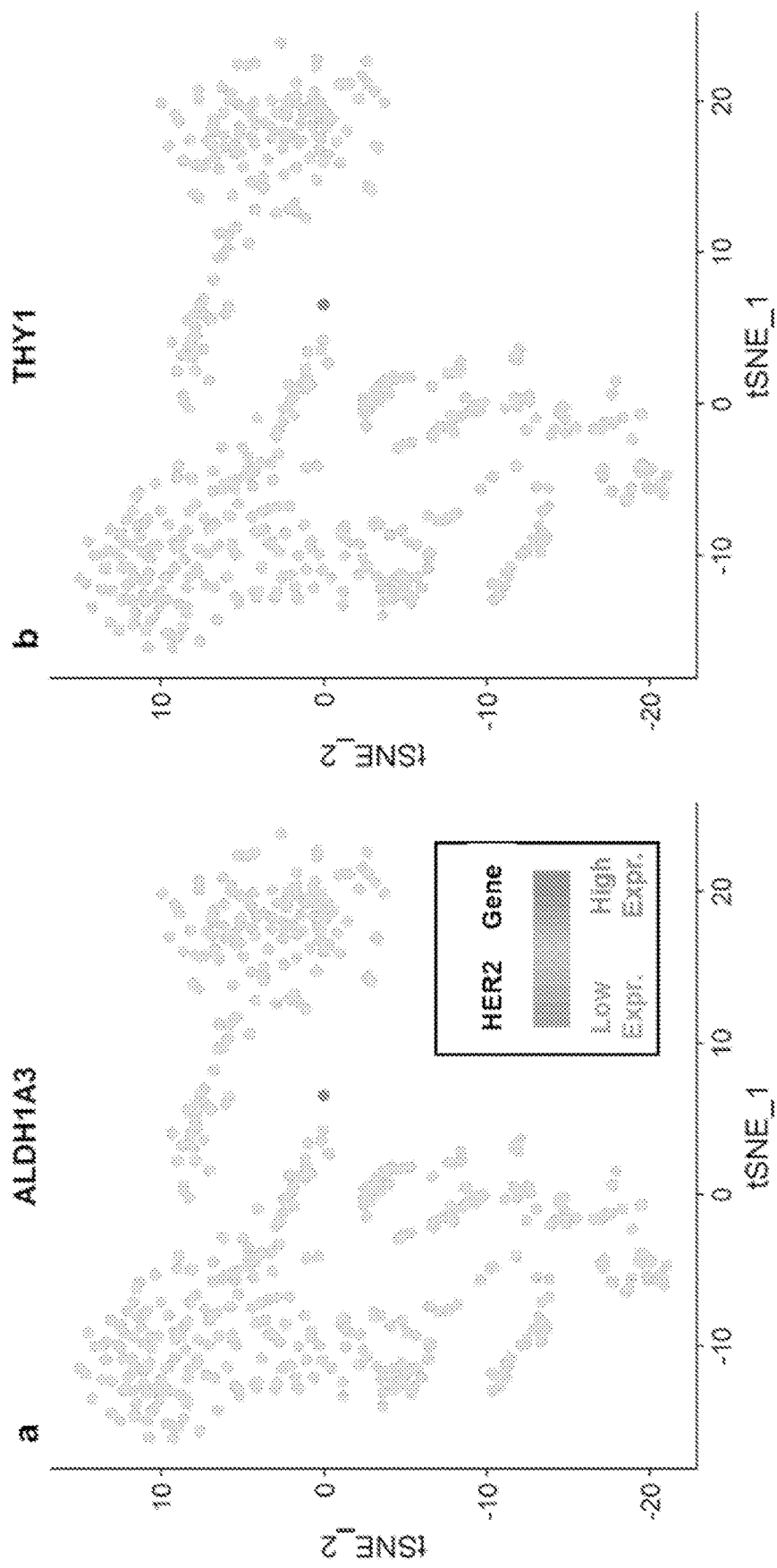
FIG. 39 shows gene expression of breast CTCs. (a-b) The expression of cancer-stem-like cell (CSC) markers: (a) Aldehyde dehydrogenase (ALDH1A3) and (b) CD90 (THY1).

After characterizing the Hydro-Seq platform, 19 patient samples were processed. 550 CTCs were detected (FIG. 28f). The captured WBCs were excluded based on the expression of CD45 (PTPRC), and RBCs by hemoglobin (FIG. 35). Though Labyrinth and CelSee have different technical features, CTCs were profiled from both platforms. The CTCs from both platforms mixed with each other in t-Distributed Stochastic Neighbor Embedding (t-SNE) plot, showing that the difference in enrichment platforms do not affect CTC characteristics significantly (FIG. 36). Using the presented method, it was possible to detect critical breast cancer bio-markers such as Human epidermal growth factor receptor 2 (HER2/Erbb2) and Estrogen receptor (ESR1), and also prognostic markers such as Androgen receptor (AR) (FIG. 29a-c) (Bozovic-Spasojevic, I. et al. Clin. Cancer Res. 23, 2702 LP-2712 (2017)), validating the value of cancer liquid biopsy using Hydro-Seq. Discordant molecular profiles were observed in CTCs and primary tumors as described in the literature (Jakabova, A. et al. Breast Cancer Res. Treat. 166, 695-700 (2017)). When further investigating the molecular characteristics of all CTCs, it was found they were easily separated by tSNE to two groups: HER2+ mesenchymal-to-epithelial transition (MET)-like and HER2-epithelial-to-mesenchymal transition (EMT)-like CTCs (FIG. 29d), which have the comparable housekeeping gene expression (GAPDH) and the number of transcripts (UMI) detected per cell (FIG. 29e and FIG. 38). HER2+ MET-like CTCs are considered proliferative due to their high expression of cyclin D1 (CCND1) and JUN (FIG. 29f-g), which are required for progression through the G1 phase of cell cycle. In addition, HER2+ MET-like CTCs express epithelial markers, including Cadherin-1 (CDH1), Epithelial Cell Adhesion Molecule (EPCAM) and Keratin-18 (KRT18) (FIG. 29h-j), while HER2− EMT-like CTCs show EMT transcription factor ZEB2 and transforming growth factor β (TGFB1) (FIG. 30k-l) (Tsai, J. H. & Yang, J. Genes Dev. 27, 2192-2206 (2013). The significant heterogeneity of CTCs highlights the limitation of marker-based CTC isolation that may lose critical CTC sub-populations (Ferreira et al., supra). In contrast, size filtration methods such as those described here can isolate and analyze a broader spectrum of CTCs. Detailed comparison between two groups are included in FIG. 39.

The experiments described herein identified a CTC expressing remarkably high Aldehyde dehydrogenase (ALDH1A3) and CD90 (THY1) (FIG. 39), which are known cancer-stem-like cell (CSC) markers. This unique cell is likely to be lost in conventional low-efficiency low-throughput CTC profiling methods. Though CTCs from one patient are generally cluster together, a patient sample containing both HER2+ MET-like and HER2− EMT-like CTCs was identified (FIG. 29m). Using whole transcriptome sequencing, the differentially expressed genes were identified a pathway analysis was performed, elucidating the big picture of bio-process regulation (FIG. 29n).

In conclusion, this example describes profiling of hundreds of CTCs from patients. The presented method is advantageous in (1) Size-based CTC isolation prevents the bias caused by marker-based isolation and enables observing heterogeneity of CTCs. (2) High-efficiency and high-throughput CTC profiling facilitates the discovery of rare CTC subtypes. (3) The whole transcriptome sequencing of CTCs provides a comprehensive understanding of regulation pathway rather than insufficient information provided by fluorescent staining. As such, the presented method represents an improvement in CTC profiling with use for other rare cell applications. The comprehensive profiling capability ultimately facilitates cancer patient diagnostics, treatment selection, and prognostics, along with other uses.

All publications and patents mentioned in the above specification are herein incorporated by reference. Various modifications and variations of the described method and system of the disclosure will be apparent to those skilled in the art without departing from the scope and spirit of the disclosure. Although the disclosure has been described in connection with specific preferred embodiments, it should be understood that the disclosure as claimed should not be unduly limited to such specific embodiments. Indeed, various modifications of the described modes for carrying out the disclosure that are obvious to those skilled in molecular biology, in vitro fertilization, development, or related fields are intended to be within the scope of the following claims.

The invention claimed is:

1. A microfluidic device, comprising:
 a plurality of branched channels comprising an entrance channel and an exit channel and a plurality of parallel single cell chambers each comprising a cell capture site and a bead capture site disposed therein, wherein said cell capture site and said bead capture site are separated by a wall comprising an isolation valve.

2. The device of claim 1, wherein said entrance channel is tapered smaller in the direction of fluid flow and said exit channel is tapered larger in the direction of fluid flow.

3. The device of claim 1, wherein said device further comprises a fluid inlet and/or a fluid outlet.

4. The device of claim 1, wherein said entrance and exit channels have a height of at least 5 times the height of said single cell chambers.

5. The device of claim 1, wherein said device comprises at least 500 single cell chambers.

6. The device of claim 1, wherein said single cell chambers further comprise an entrance valve distal to said single cell chamber.

7. The device of claim 6, wherein said single cell chambers further comprise an exit valve proximal to said single cell chamber.

8. The device of claim 1, wherein said cell capture site and said bead capture site comprise sealing valves proximal to said cell capture site and distal to said bead capture site.

9. The device of claim 1, wherein said device further comprises a plurality of wash valve controlled washing channels in fluid communication with said entrance channel and said exit channel, wherein said washing channels each comprise a wash valve.

10. The device of claim 6, wherein said entrance valve is addressable.

11. The device of claim 1, wherein said cell capture chamber and said bead capture site are configured to allow laminar flow to said bead capture chamber when buffer is introduced to said bead capture chamber.

12. The device of claim 1, wherein said bead capture site comprises a bead capture channel at the bottom of said bead capture site, wherein said bead capture channel has a rectangular shape.

13. The device of claim 12, wherein the opening of said bead capture channel is smaller than the diameter of a bead in said bead capture site.

14. The device of claim 12, wherein said bead capture channel allows fluid flow into and out of said bead capture channel while retaining a bead in said channel or capture site.

15. The device of claim 1, wherein at least a portion of the interior of said device is coated with a material that prevents adhesion of nucleic acids to said device.

16. The device of claim 7, wherein said exit valve is addressable.

17. The device of claim 8, wherein said sealing valve is addressable.

18. The device of claim 9, wherein said wash valve is addressable.

19. The device of claim 1, wherein said isolation valve is addressable.

20. The device of claim 1, wherein said wall is at least 20 μm thick and 20 μm long.

* * * * *